(12) United States Patent
Gordon et al.

(10) Patent No.: US 8,940,019 B2
(45) Date of Patent: Jan. 27, 2015

(54) BONE TISSUE FIXATION DEVICE AND METHOD

(75) Inventors: Charles Gordon, Tyler, TX (US); James E. Deaton, Georgetown, TX (US)

(73) Assignee: OsteoMed Spine, Inc., Addison, TX (US)

( * ) Notice: Subject to any disclaimer, the term of this patent is extended or adjusted under 35 U.S.C. 154(b) by 1125 days.

(21) Appl. No.: 12/342,816

(22) Filed: Dec. 23, 2008

(65) Prior Publication Data

US 2009/0198277 A1 Aug. 6, 2009

Related U.S. Application Data

(60) Provisional application No. 61/017,336, filed on Dec. 28, 2007, provisional application No. 61/023,327, filed on Jan. 24, 2008, provisional application No. 61/104,199, filed on Oct. 9, 2008, provisional application No. 61/108,368, filed on Oct. 24, 2008.

(51) Int. Cl.
*A61B 17/70* (2006.01)
*A61B 17/68* (2006.01)
*A61B 17/80* (2006.01)

(52) U.S. Cl.
CPC .......... *A61B 17/7062* (2013.01); *A61B 17/688* (2013.01); *A61B 17/7053* (2013.01); *A61B 17/8061* (2013.01); *A61B 17/8076* (2013.01); *A61B 17/8085* (2013.01)
USPC .......................................... 606/248; 606/249

(58) Field of Classification Search
CPC . A61F 2/44; A61F 2/4455; A61F 2002/4475; A61F 2/442; A61B 17/70
USPC .......................... 606/246, 248–249, 263, 279; 623/17.11–17.16
See application file for complete search history.

(56) References Cited

U.S. PATENT DOCUMENTS 3,242,922 A 3/1966 Thomas .................. 606/250
(Continued)

FOREIGN PATENT DOCUMENTS

| EP | 1477124 | 10/2007 |
| WO | WO 00/62693 | 10/2000 |

(Continued)

OTHER PUBLICATIONS

"Aspen Spinous Process System" by Lanx, available online at http://www.spineansi.com/080607_Aspen_Lab_Presentation.ppt, no date, accessed Jun. 10, 2009. "OHSU surgeons find new way to fix painful broken ribs," Oregon Health & Science University, http://www.ohsu.edu/ohsuedu/newspub/releases/062706ribs.cfm, Jun. 27, 2006.

(Continued)

*Primary Examiner* — Mary Hoffman
*Assistant Examiner* — Christina Negrellirodrigue
(74) *Attorney, Agent, or Firm* — Fulbright & Jaworski LLP

(57) ABSTRACT

Systems, methods, and kits incorporating a clamp for securing to bone tissue. The clamp includes gripping members to secure the clamp to the bone tissue without the use of screws. The clamp may be used to treat spinal conditions, and may be secured to the spinous process of vertebrae. Systems, methods and kits can incorporate a fusion member configured to fuse between adjacent spinous processes.

28 Claims, 53 Drawing Sheets

(56) References Cited

U.S. PATENT DOCUMENTS

| | | | | |
|---|---|---|---|---|
| 3,469,573 | A | 9/1969 | Florio | 606/74 |
| 3,648,691 | A | 3/1972 | Lumb et al. | 606/279 |
| 4,066,082 | A | 1/1978 | Arcan et al. | |
| 4,290,328 | A | 9/1981 | Clark | |
| D281,814 | S | 12/1985 | Pratt et al. | D24/145 |
| 4,570,623 | A | 2/1986 | Ellison et al. | 606/75 |
| 4,592,346 | A | 6/1986 | Jurgutis | 606/75 |
| 4,848,328 | A | 7/1989 | Laboureau et al. | 606/75 |
| 4,852,558 | A | 8/1989 | Outerbride | 606/75 |
| 4,913,144 | A | 4/1990 | Del Medico | 606/75 |
| 4,994,073 | A | 2/1991 | Green | 606/220 |
| 5,007,909 | A | 4/1991 | Rogozinski | 606/277 |
| 5,011,484 | A | 4/1991 | Beard | 606/249 |
| 5,053,038 | A | 10/1991 | Sheehan | 606/75 |
| 5,074,864 | A | 12/1991 | Cozad et al. | 606/54 |
| 5,108,422 | A | 4/1992 | Green et al. | 606/219 |
| 5,196,318 | A | 3/1993 | Baldwin et al. | 435/69.1 |
| 5,201,746 | A | 4/1993 | Shichman | 606/151 |
| 5,246,442 | A | 9/1993 | Ashman et al. | 606/278 |
| 5,261,909 | A | 11/1993 | Sutterlin et al. | |
| 5,290,312 | A | 3/1994 | Kojimoto et al. | |
| 5,395,370 | A | 3/1995 | Muller et al. | 606/276 |
| 5,454,814 | A | 10/1995 | Comte | 606/75 |
| 5,496,318 | A | 3/1996 | Howland et al. | 606/249 |
| 5,609,634 | A | 3/1997 | Voydeville | 623/17 |
| 5,611,800 | A | 3/1997 | Davis et al. | |
| 5,626,592 | A | 5/1997 | Phillips et al. | 606/157 |
| 5,645,599 | A | 7/1997 | Samani | 623/17 |
| 5,713,911 | A | 2/1998 | Racenet et al. | 606/157 |
| 5,722,976 | A | 3/1998 | Brown | |
| 5,836,948 | A | 11/1998 | Zucherman et al. | |
| 5,853,414 | A | 12/1998 | Groiso | 606/75 |
| 5,941,881 | A | 8/1999 | Barnes | 606/71 |
| 6,007,538 | A | 12/1999 | Levin | 606/71 |
| 6,148,696 | A | 11/2000 | Chiang | |
| 6,238,397 | B1 | 5/2001 | Zucherman et al. | |
| 6,312,431 | B1 | 11/2001 | Asfora | |
| 6,332,883 | B1 | 12/2001 | Zucherman et al. | |
| 6,336,928 | B1 | 1/2002 | Guerin et al. | 606/282 |
| 6,352,537 | B1 | 3/2002 | Strnad | 606/276 |
| 6,364,883 | B1 | 4/2002 | Santilli | 606/279 |
| 6,375,683 | B1 | 4/2002 | Crozet et al. | |
| 6,379,355 | B1 | 4/2002 | Zucherman et al. | |
| 6,440,169 | B1 | 8/2002 | Elberg et al. | 623/17.16 |
| 6,443,987 | B1 | 9/2002 | Bryan | |
| 6,451,019 | B1 | 9/2002 | Zucherman et al. | 606/61 |
| 6,485,518 | B1 | 11/2002 | Cornwall et al. | |
| 6,558,387 | B2 | 5/2003 | Errico et al. | 606/247 |
| 6,565,573 | B1 | 5/2003 | Ferrante et al. | |
| 6,582,435 | B2 | 6/2003 | Wellsiz et al. | 606/75 |
| 6,641,585 | B2 | 11/2003 | Sato et al. | 606/261 |
| 6,695,842 | B2 | 2/2004 | Zucherman et al. | |
| 6,699,247 | B2 | 3/2004 | Zucherman et al. | 606/86 A |
| 6,712,819 | B2 | 3/2004 | Zucherman et al. | |
| 6,761,720 | B1 | 7/2004 | Senegas | 606/249 |
| 6,783,531 | B2 | 8/2004 | Allen | 606/75 |
| 6,796,983 | B1 | 9/2004 | Zucherman et al. | |
| 6,923,812 | B1 | 8/2005 | Wellsz | 606/72 |
| 6,969,391 | B1 | 11/2005 | Gazzani | 606/75 |
| 7,025,787 | B2 | 4/2006 | Bryan et al. | |
| 7,048,736 | B2 | 5/2006 | Robinson et al. | 606/86 B |
| 7,060,068 | B2 | 6/2006 | Tromanhauser et al. | |
| 7,229,444 | B2 | 6/2007 | Boyd | 606/300 |
| 7,250,060 | B2 | 7/2007 | Trieu | |
| 7,255,698 | B2 | 8/2007 | Michelson | 606/247 |
| 7,294,128 | B2 | 11/2007 | Alleyne et al. | |
| 7,335,203 | B2 | 2/2008 | Winslow et al. | 606/249 |
| 7,377,921 | B2 | 5/2008 | Studer et al. | 606/248 |
| 7,393,361 | B2 | 7/2008 | Zubok et al. | |
| 7,396,360 | B2 | 7/2008 | Lieberman | |
| 7,588,592 | B2 | 9/2009 | Winslow et al. | |
| 7,666,228 | B2* | 2/2010 | Le Couedic et al. | 623/17.11 |
| 7,727,233 | B2 | 6/2010 | Blackwell et al. | |
| 7,857,857 | B2 | 12/2010 | Kim | |
| 7,862,592 | B2* | 1/2011 | Peterson et al. | 606/249 |
| 7,871,426 | B2 | 1/2011 | Chin et al. | |
| 7,935,133 | B2 | 5/2011 | Malek | |
| 7,955,392 | B2 | 6/2011 | Dewey et al. | |
| 8,043,337 | B2 | 10/2011 | Klyce et al. | |
| 8,048,120 | B1* | 11/2011 | Fallin et al. | 606/249 |
| 8,070,817 | B2 | 12/2011 | Gradl et al. | |
| 8,114,132 | B2 | 2/2012 | Lyons et al. | |
| 8,128,659 | B2 | 3/2012 | Ginsberg et al. | |
| 8,157,842 | B2 | 4/2012 | Phan et al. | |
| 2001/0020188 | A1 | 9/2001 | Sander | 623/23.57 |
| 2003/0040746 | A1 | 2/2003 | Mitchell et al. | |
| 2003/0045877 | A1 | 3/2003 | Yeh | |
| 2003/0216736 | A1 | 11/2003 | Robinson et al. | |
| 2004/0034430 | A1 | 2/2004 | Falahee | 623/17.16 |
| 2004/0106995 | A1 | 6/2004 | Le Couedic et al. | |
| 2004/0193272 | A1 | 9/2004 | Zubok et al. | |
| 2005/0043732 | A1 | 2/2005 | Dalton | 606/17 |
| 2005/0137594 | A1 | 6/2005 | Doubler et al. | 606/279 |
| 2005/0216017 | A1 | 9/2005 | Fielding et al. | 606/7 |
| 2005/0234459 | A1 | 10/2005 | Falahee et al. | |
| 2005/0256582 | A1 | 11/2005 | Ferree | 623/17.16 |
| 2006/0004367 | A1 | 1/2006 | Alamin et al. | 606/74 |
| 2006/0074425 | A1 | 4/2006 | Sutterlin et al. | |
| 2006/0142771 | A1 | 6/2006 | Beutter | 606/75 |
| 2006/0235391 | A1 | 10/2006 | Sutterlin | |
| 2006/0235518 | A1 | 10/2006 | Blain | |
| 2006/0241601 | A1 | 10/2006 | Trautwein et al. | 606/248 |
| 2006/0247623 | A1 | 11/2006 | Anderson et al. | |
| 2006/0247634 | A1 | 11/2006 | Warner et al. | |
| 2006/0247640 | A1 | 11/2006 | Blackwell et al. | |
| 2006/0287654 | A1 | 12/2006 | Posnick | 606/72 |
| 2007/0016189 | A1 | 1/2007 | Lake et al. | 606/250 |
| 2007/0093823 | A1 | 4/2007 | Booth et al. | 606/249 |
| 2007/0162001 | A1 | 7/2007 | Chin et al. | 606/276 |
| 2007/0179500 | A1 | 8/2007 | Chin et al. | 606/276 |
| 2007/0191844 | A1 | 8/2007 | Carls et al. | 606/86 A |
| 2007/0233082 | A1 | 10/2007 | Chin et al. | 606/276 |
| 2007/0250065 | A1 | 10/2007 | Efron et al. | 606/75 |
| 2007/0270812 | A1 | 11/2007 | Peckham | 606/279 |
| 2007/0270840 | A1 | 11/2007 | Chin et al. | |
| 2007/0276384 | A1 | 11/2007 | Spratt | |
| 2007/0276500 | A1* | 11/2007 | Zucherman et al. | 623/17.16 |
| 2008/0021471 | A1 | 1/2008 | Winslow et al. | 606/249 |
| 2008/0021472 | A1 | 1/2008 | Winslow et al. | 606/61 |
| 2008/0103512 | A1 | 5/2008 | Gately | |
| 2008/0140125 | A1 | 6/2008 | Mitchell et al. | |
| 2008/0147190 | A1 | 6/2008 | Dewey et al. | |
| 2008/0177330 | A1 | 7/2008 | Ralph et al. | |
| 2008/0183211 | A1* | 7/2008 | Lamborne et al. | 606/249 |
| 2008/0183218 | A1 | 7/2008 | Mueller et al. | |
| 2008/0228225 | A1 | 9/2008 | Trautwein et al. | |
| 2008/0243185 | A1 | 10/2008 | Felix et al. | |
| 2008/0243186 | A1 | 10/2008 | Abdou | |
| 2008/0281359 | A1 | 11/2008 | Abdou | |
| 2009/0018658 | A1 | 1/2009 | Garcia | 623/17.11 |
| 2009/0062918 | A1 | 3/2009 | Wang et al. | |
| 2009/0216272 | A1 | 8/2009 | Currier et al. | |
| 2009/0216273 | A1 | 8/2009 | Cox | |
| 2009/0264927 | A1 | 10/2009 | Ginsberg et al. | |
| 2009/0270918 | A1* | 10/2009 | Attia et al. | 606/248 |
| 2009/0326589 | A1 | 12/2009 | Lemoine et al. | |
| 2010/0036419 | A1 | 2/2010 | Patel et al. | |
| 2010/0087860 | A1 | 4/2010 | Chin et al. | |
| 2010/0241167 | A1 | 9/2010 | Taber et al. | |
| 2010/0318127 | A1 | 12/2010 | Phan et al. | |
| 2011/0029020 | A1 | 2/2011 | Gordon et al. | |
| 2011/0054531 | A1 | 3/2011 | Lamborne et al. | |
| 2011/0066186 | A1 | 3/2011 | Boyer, II et al. | |
| 2011/0144692 | A1 | 6/2011 | Saladin et al. | |
| 2011/0166600 | A1 | 7/2011 | Lamborne et al. | |
| 2011/0224731 | A1 | 9/2011 | Smisson, III et al. | |
| 2011/0224740 | A1 | 9/2011 | Smisson, III et al. | |
| 2011/0313458 | A1 | 12/2011 | Butler et al. | |
| 2011/0319936 | A1 | 12/2011 | Gordon et al. | |
| 2012/0010662 | A1 | 1/2012 | O'Neil et al. | |
| 2012/0016418 | A1 | 1/2012 | Chin et al. | |
| 2012/0078304 | A1 | 3/2012 | Jensen et al. | |
| 2012/0078305 | A1 | 3/2012 | Wang et al. | |
| 2012/0083844 | A1 | 4/2012 | Linares | |

(56) References Cited

U.S. PATENT DOCUMENTS

| | | | |
|---|---|---|---|
| 2012/0083846 A1 | 4/2012 | Wallenstein et al. |
| 2012/0089184 A1 | 4/2012 | Yeh |
| 2012/0095512 A1 | 4/2012 | Nihalani |
| 2012/0101528 A1 | 4/2012 | Souza et al. |
| 2012/0109198 A1 | 5/2012 | Dryer et al. |
| 2012/0109203 A1 | 5/2012 | Dryer et al. |
| 2012/0109205 A1 | 5/2012 | Mitchell et al. |
| 2012/0123475 A1 | 5/2012 | Ahn et al. |
| 2012/0136390 A1 | 5/2012 | Butler et al. |
| 2012/0143252 A1 | 6/2012 | Robinson |
| 2012/0150228 A1 | 6/2012 | Zappacosta et al. |
| 2012/0158061 A1 | 6/2012 | Koch et al. |
| 2012/0158063 A1 | 6/2012 | Altarac et al. |
| 2012/0310292 A1 | 12/2012 | Smisson, III et al. |

FOREIGN PATENT DOCUMENTS

| | | |
|---|---|---|
| WO | WO-2007/109402 A2 | 9/2007 |
| WO | WO-2009/086397 A2 | 7/2009 |
| WO | WO-03/007829 A1 | 1/2013 |

OTHER PUBLICATIONS

International Search Report and Written Opinion issued in International Application No. PCT/US08/88204, mailed Feb. 12, 2009.

Sénégas, "Minimally invasive dynamic stabilisation of the lumbar motion segment with an interspinous implant," *Minimally Invasive Spine Surgery*, 459-465, 2006.

United States Provisional Patent Application No. 60/74,632, entitled "Inter-spinous orthopedic device placement and method of use," filed Oct. 7, 2005.

International Search Report and Written Opinion issued in International Application No. PCT/2008/088196, mailed Apr. 23, 2009.

Bostman et al., "Posterior spinal fusion using internal fixation with the Daab plate," *Acta. Orthop. Scand.*, 55:310-314, 1984.

Globus Medical: "SP-Fix Spinous Process Fixation Plate: Surgical Technique," pp. 1-32 Jan. 2011.

LANX, "Aspen Spinous Process System Product Brochure," www.lanx.com, Dec. 16, 2008.

Saint John's Health Center, "Saint John's Spine Surgeion Uses ILIF Procedure to Treat Lumbar Spinal Stenosis," www.medicalnewstoday.com/articles/155013.php.

\* cited by examiner

BONE TISSUE FIXATION DEVICE AND METHOD

RELATED APPLICATIONS

This application claims priority to, and incorporates by reference, each of the following applications: U.S. Provisional Patent Application 61/017,336 filed Dec. 28, 2007; U.S. Provisional Patent Application 61/023,327 filed Jan. 24, 2008; U.S. Provisional Patent Application 61/104,199 filed Oct. 9, 2008; and U.S. Provisional Patent Application 61/108,368 filed Oct. 24, 2008.

BACKGROUND INFORMATION

1. Field of the Invention

Exemplary embodiments of the present disclosure comprise a devices that can be secured to bone tissue and methods of securing the devices. In specific exemplary embodiments, a device may be secured to a spinous process of a vertebra. In other exemplary embodiments, a device may be secured to a calvarial flap or other bone tissue.

2. Description of Related Art

The pedicle screw is a common medical device currently used to attach components to a patient's vertebrae. While providing a stable platform to attach components to vertebrae, the pedicle screw has inherent drawbacks in its use. Such drawbacks include the difficulty in accessing the portion of the vertebrae needed to insert the pedicle screw. In addition, there are risks of serious injuries to the patient when using a pedicle screw to penetrate a vertebra in a region close to the nerves of the spinal cord.

Systems and methods for treatment for various spinal conditions have been disclosed in U.S. Pat. Nos. 5,645,599 and 6,440,169, incorporated herein by reference. Additional systems and methods of treatment have been disclosed in "Interspinous Process Decompression for Neurogenic Intermittent Claudication Secondary to Degenerative Lumbar Spinal Stenosis", Global Surgery—Future Directions 2005 by Patrick Simons, also incorporated herein by reference.

SUMMARY

Exemplary embodiments of the present disclosure provide novel systems, kits, and methods for securing medical devices to bones for use in treatment of spinal conditions and other medical conditions where securement to bone tissue is needed.

Certain exemplary embodiments comprise a system having a first clamp comprising: a first side; a second side; a coupling portion coupling the first side to the second side; an open space between the first and second side; and a plurality of gripping members disposed on at least one of the first and second side. Other embodiments include a second clamp comprising: a first side; a second side; a coupling portion coupling the first side to the second side; an open space between the first and second side; and a plurality of gripping members disposed on at least one of the first and second side. In certain embodiments, the first clamp and the second clamp may further comprise a receiving member and/or a coupling member disposed between a receiving member of the first clamp and a receiving member of the second clamp.

In certain embodiments, a clamp may comprise gripping members that comprise projections directed toward the open space. The clamp may be configured to allow a foreign object to be inserted into the open space. The clamp may be configured to exert a compressive force on the foreign object in certain embodiments, and a cross-section of the first clamp may be generally U-shaped. The first side and the second side of a clamp may be comprised of a unitary piece. In particular embodiments, the first side comprises a first end portion distal from the coupling portion; the second side comprises a second end portion distal from the coupling portion; and the first side and the second side are angled towards each other so that the first end portion is proximal to the second end portion.

In specific exemplary embodiments, the plurality of gripping members may be comprised of indentations in the first side and the second side. Certain embodiments may comprise a first clamp configured for affixation to a spinous process of a first vertebra and a second clamp configured for affixation to a spinous process of a second vertebra. In specific embodiments, the first clamp may be configured for affixation to a first face of the spinous process of the first vertebra and the second clamp may be configured for affixation to a second face of the spinous process of the second vertebra, and the first face may be opposing the second face. Certain exemplary embodiments may further comprise a coupling member disposed between a receiving member of the first clamp and a receiving member of the second clamp, thereby providing segmental fixation of the first vertebrae and the second vertebrae. In certain embodiments, the coupling member and/or the receiving member may comprise a threaded portion or a socket.

In specific embodiments, a system includes a clamp configured for affixation to a spinous process of a first vertebra and for affixation to a spinous process of a second vertebra. In other specific embodiments, the clamp may be configured for securement to a calvarial flap, soft tissue, across a joint such as a metatarsophalangeal articulation, across a long bone such as a humeral fracture, or across a small bone in a hand or foot. In specific embodiments, a clamp may comprise an extension configured to couple to a securement device secured to a cranium. In still more specific embodiments, the securement device may be a screw.

In certain embodiments, the first and second side of the clamp are part of first and second side portions that each have a U-shaped cross section. In specific embodiments, the first and second side portions have an aperture, and in certain embodiments the aperture is multi-faceted. In exemplary embodiments, the coupling portion of the clamp is coupled to a top portion that extends into a space between the sides. In certain embodiments, the coupling portion is coupled to a pair of end portions that extend into a space between the sides.

Exemplary embodiments can also include a kit comprising a plurality of clamps and a plurality of coupling members configured to couple a first clamp to a second clamp. In certain embodiments, a first coupling member comprises an elongate rigid rod and a second coupling member comprises a first end, a second end, and a biasing member. Specific embodiments may also a third coupling member that comprises a dampener. In certain embodiments, the biasing member can be configured to bias the first end of the second coupling member towards the second end of the second coupling member when a tensile force is placed on the second coupling member. In specific embodiments, the biasing member is configured to bias the first end of the second coupling member away from the second end of the second coupling member when a compressive force is placed on the second coupling member.

Certain exemplary embodiments may also comprise a method of treating a spinal condition. The method may comprise securing a first clamp to a first spinous process of a first vertebra, and securing a securement device to a second vertebra. The method may also comprise coupling the first clamp to the securement device via a coupling member. In certain embodiments, the securement device is a second clamp and/or the coupling member comprises a rigid rod. In exemplary embodiments, the coupling member comprises a biasing member and/or a dampener. Specific embodiments comprise securing a first clamp to a first spinous process of a first vertebra comprises the use of cement, epoxy, banding, or small screws.

Exemplary embodiments may also include a system comprising: a first anchor structure; a second anchor structure; a fusion member disposed between the first anchor structure and the second anchor structure; and a tension member configured to apply tension between the first anchor structure and the second anchor structure. In certain embodiments, the fusion member is configured to be compressed between a first spinous process and a second spinous process during use. In specific embodiments, the fusion member comprises a bone allograft. In particular embodiments, the fusion member comprises a cage defining a volume, and in specific embodiment the fusion member further comprises a bone fragment disposed on the interior of the volume. In exemplary embodiments, the first anchor structure and the second anchor structure further comprise a cap configured to engage a bone structure.

In certain embodiments, the first anchor structure and the second anchor structure further each comprise an gripping member configured to attach the first anchor structure and the second anchor structure to a bone structure. In specific embodiments, the tension member further comprises a cable having a first end and a second end, the first end coupled to the first anchor structure and the second end coupled to the second anchor structure. Certain embodiments also comprise an alignment member coupled to the fusion member, where the alignment member is configured to align the fusion member between the first anchor member and the second anchor member. Particular embodiments also comprise a fastener configured to fasten the tension member to the first anchor structure and to the second anchor structure.

Other embodiments include a method comprising: positioning a fusion member in an interspinous space between a first spinous process and a second spinous process; and fusing the fusion member to the first spinous process and the second spinous process. Certain embodiments further comprise compressing the fusion member between the first spinous process and the second spinous process. Specific embodiments also comprise affixing a first anchor structure to a first spinous process; affixing a second anchor structure to a second spinous process; and applying tension between the first anchor and the second anchor structure prior to positioning the fusion member in the interspinous space between the first spinous process and the second spinous process.

Certain embodiments further comprise positioning the first and second anchor structures in proximity of the first and second spinous processes; aligning the first and second anchor structures; and clamping the first and second anchor structures to the first and second spinous processes respectively. In specific embodiments, applying tension further comprises coupling the first anchor structure to the second anchor structure by a tension member and applying a tension load between the first anchor structure and the second anchor structure with the tension member. In specific embodiments, applying tension further comprises threading a cable through one or more alignment guides and securing the cable at a predetermined tension load. One or more alignment guides can be integrated with at least one of the first anchor structure, the second anchor structure, and the fusion member. Certain embodiments further comprise disposing a fragment of bone within an interior portion of a volume defined by the fusion member. Specific embodiments further comprise distracting the interspinous space between the first spinous process and the second spinous process.

In certain embodiments, distracting the interspinous space comprises: coupling a first leverage member to the first spinous process; coupling a second leverage member to the second spinous process; and applying a first force to the first leverage member and a second force to the second leverage member. In specific embodiments, the first force and the second force are applied via a ratcheting member placed between the first leverage member and the second leverage member. In particular embodiments, the first force is applied in a direction such that the first spinous member is moved farther away from the second spinous member. In certain embodiments, the second force is applied in direction such that the second spinous member is moved farther away from the first spinous member. In specific embodiments, the fusion member comprises a tapered surface. In particular embodiments, distracting the interspinous space comprises inserting the fusion member between the first and second spinous process such that the tapered surface acts on at least one of the first and second spinous processes.

In certain embodiments, the fusion member comprises a first concave portion configured to engage a first spinous process and wherein the fusion member comprises a second concave portion configured to engage a second spinous process. In specific embodiments, the fusion member is "H"-shaped when viewed from above in an installed position. In particular embodiments, the body of the fusion member comprises a plurality of apertures. In specific embodiments, the plurality of apertures are in the first concave portion and in the second concave portion.

Certain embodiments further comprise coupling a stabilizing member to the first spinous process and the second spinous process. In specific embodiments, the stabilizing member is a plate and coupling the stabilizing member to the first spinous process and the second spinous process comprises inserting threaded coupling members into the first and second spinous processes.

Specific embodiments include a system comprising: a fusion member configured for insertion between a first spinous process and a second spinous process; and a securement device configured to secure the fusion member between the first spinous process and the second spinous process. In certain embodiments, the securement device is selected from the group consisting of: a band, a plate, a pedicle screw, a pedicle screw system, a clamp, a bracket, a wire, a cable, and a prong. In specific embodiments, the fusion member comprises a cage. The fusion member may also comprise bone tissue.

In particular embodiments, the securement device comprises a band. The band can be configured to form a loop around a first spinous process and a second spinous process; and an adjustment member configured to adjust the circumference of the loop. In certain embodiments, the band comprises: a first end; a second end; and a plurality of engagement members proximal to the first end. Specific embodiments further comprise a plurality of openings, where an engagement member is located between a pair of openings. In specific embodiments, the plurality of openings and the plurality of engagement members are arranged such that the openings and engagement members form a series of alternating openings and engagement members. In certain embodiments, the band comprises a retention member configured to retain the adjustment member. In specific embodiments, the adjustment member is configured to engage the plurality of engagement members proximal to the end of the band. In certain embodiments, the adjustment member comprises a plurality of projections configured to engage the plurality of engagement members proximal to the end of the band.

In certain embodiments, the adjustment member is configured to rotate within the retention member and adjust the circumference of the loop. Specific embodiments comprise a biasing member configured to bias the adjustment member to a locked position. Particular embodiments comprise a ratchet mechanism, wherein the ratchet mechanism is configured to allow the adjustment member to reduce the circumference of the loop when the adjustment member is in the locked position.

In certain embodiments, the adjustment member can be moved from the locked position to an unlocked position by overcoming a force exerted on the adjustment member by the biasing member. The adjustment member can be manipulated to increase the circumference of the loop when the adjustment member is in the unlocked position in certain embodiments. In particular embodiments, the fusion member is configured to be compressed between a first spinous process and a second spinous process during use. In specific embodiments, the fusion member comprises a cage defining a volume. In certain embodiments, the cage comprises a plurality of cage apertures proximal to a spinous process during use. The fusion member further comprises a bone fragment disposed in the interior of the volume in certain embodiments. In particular embodiments, the band comprises a molded polymer. In specific embodiments, the band comprises an alignment member configured to engage a slot in the fusion member. The alignment member and the slot are engaged in a sliding fixation in particular embodiments. In particular embodiments, the alignment member and the slot form a dovetail joint.

In certain embodiments, the band comprises a plurality of openings configured to increase the flexibility of the band. In particular embodiments, the plurality of openings comprises parallel slots configured to extend partially around the circumference of the loop. The plurality of openings are located where the band is configured to engage a spinous process during use, in particular embodiments. In specific embodiments, the band comprises a narrowed portion configured to increase the flexibility of the band. In certain embodiments, the band comprises: a first plurality of openings; a second plurality of openings; and a first narrowed portion, a second narrowed portion, a third narrowed portion and a fourth narrowed portion, wherein the first plurality of openings are located between the first and second narrowed portions and wherein the second plurality of openings are located between the third and fourth narrowed portions.

Certain embodiments comprise a system comprising: a first fusion member configured for insertion between a first spinous process and a second spinous process; a second fusion member configured for insertion between the second spinous process and a third spinous process; a first band comprising a first end and a second end; a second band comprising a first end and a second end; and a first adjustment member. In particular embodiments, the first band and the second band are configured to be coupled together to form a loop around the first and third spinous processes, and the first adjustment member is configured to adjust the circumference of the loop. In certain embodiments, the first end of the second band is coupled to the second end of the first band via the first adjustment member and wherein the second end of the second band is coupled to the first end of the first band via the second adjustment member.

Certain embodiments comprise a method for reducing scoliosis of a spine, where the method comprises providing a system described above and manipulating an adjustment member to adjust the circumference of a loop formed by a band in the system in order to provide compression on a convex side of the spine. The method may further comprise manipulating an adjustment member to adjust the circumference of a loop formed by a band in the system in order to accommodate skeletal growth, where adjusting the band is performed over the course of multiple surgical procedures.

Specific embodiments include a method for treating spinal disorders, where the method comprises: coupling a first leverage member to a first spinous process; coupling a second leverage member to a second spinous process; distracting or compressing the leverage members to provide spinal manipulation interoperatively and to provide a modified spinal alignment; placing a fusion member between the first spinous process and the second spinous process; and securing the fusion member in place between the first spinous process and the second spinous process.

Certain embodiments comprise a fusion member comprising: a body comprising a first end and a second end; a first concave portion proximal to the first end, wherein the first concave portion is configured to engage a first spinous process; and a second concave portion proximal to the second end, wherein the second concave portion is configured to engage a second spinous process. In specific embodiments, the fusion member body may comprise an "H" shape when viewed from above in an installed position; the body of the fusion member comprises a plurality of apertures. In certain embodiments a plurality of apertures are in the first concave portion and in the second concave portion.

Certain embodiments comprise an interspinous member where the interspinous member is configured to engage adjacent spinous processes. In specific embodiments, the interspinous member comprises a first concave portion configured to engage a first spinous process and a second concave portion configured to engage a second spinous process. Particular embodiments comprise a system comprising: a fusion member configured for insertion between a first spinous process and a second spinous process; a stabilizing member configured for coupling to the first spinous process and to the second spinous process; and one or more coupling members configured to couple the stabilizing member to the first spinous process and the second spinous process. In specific embodiments, the stabilizing member comprises a plate and/or the fusion member comprises a tapered surface. Particular embodiments comprise a first leverage member configured to couple to the first spinous process and a second leverage member configured to couple to the second spinous process.

In a further embodiment, a system includes a first anchor structure, a second anchor structure a fusion member disposed between the first anchor structure and the second anchor structure, wherein the fusion member comprises a cage defining a volume, and a tension member configured to apply tension between the first anchor structure and the second anchor structure, and the first anchor structure and the second anchor structure compressing the fusion member. In a further embodiment, the fusion member is configured to be compressed between a first spinous process and a second spinous process during use. Additional embodiments of the fusion member may include a bone fragment disposed on the interior of the volume.

In exemplary embodiments, the fusion member is configured to promote fusion of adjacent spinous processes. In specific embodiments, the fusion member comprises a porous or cage-like structure that contains bone tissue or bone substitute to promote bone growth between the fusion member and the spinous process.

Fusion of the spinous processes can be accomplished with procedures and systems that are less invasive than those typically used to fuse adjacent vertebral bodies. For example, it is not required to disturb the nerve tissue between adjacent vertebrae in order to insert a fusion member between the spinous processes. In addition, the area between the spinous process can be accessed from the dorsal side of the spine.

In contrast, fusion of vertebral bodies requires access to the intervertebral space through either an anterior approach or a posterior approach. An anterior approach involves risks of the great blood vessels, the ureter, and the intestinal contents, while a posterior approach involves significant removal of bone, ligament, and joint tissue as well as significant distraction on the nerves. By comparison, the intraspinous space is an easier and safer space to access, does not require mobilization of the nerves, and is located dorsally so is not approached from an anterior or ventral access route, thereby avoids jeopardizing the anterior abdominal contents.

Other advantages may also be realized by incorporating a porous structure with bone or bone substitutes in the fusion member. For example, solid members placed between the vertebrae can cause high loads to be placed on the bone tissue and can result in changes in the internal structure and external form of the bone, according to the principles of Wolff's law. In certain instances, such a response can cause the bone tissue to pull away from the solid member placed between the vertebrae. The use of fusion members with porous, bone-containing structures can decrease the likelihood that such a response will occur.

In a specific embodiment, the first anchor structure and the second anchor structure further comprise a cap configured to engage a bone structure. The first anchor structure and the second anchor structure may include an gripping member configured to attach the first anchor structure and the second anchor structure to a bone structure.

In further embodiments, the tension member further comprises a cable having a first end and a second end, the first end coupled to the first anchor structure and the second end coupled to the second anchor structure. The system may also include an alignment member coupled to the fusion member configured to align the fusion member between the first anchor member and the second anchor member. Further, the system may include a fastener configured to fasten the tension member to the first anchor structure and to the second anchor structure.

Other embodiments include a kit comprising: a plurality of clamps; a plurality of coupling members configured to couple a first clamp to a second clamp, wherein: a first coupling member comprises an elongate rigid rod; a second coupling member comprises a first end, a second end, and a biasing member; and a third coupling member comprises a dampener. In specific embodiments, the biasing member is configured to bias the first end of the second coupling member towards the second end of the second coupling member when a tensile force is placed on the second coupling member. In other exemplary embodiments, the biasing member is configured to bias the first end of the second coupling member away from the second end of the second coupling member when a compressive force is placed on the second coupling member.

Still other embodiments include a method of treating a spinal condition, the method comprising: securing a first clamp to a first spinous process of a first vertebra; securing a securement device to a second vertebra; and coupling the first clamp to the securement device via a coupling member. In specific embodiments, the securement device may be a second clamp. In specific embodiments, the coupling member may comprise a rigid rod, a biasing member, or a dampener.

In certain embodiments, securing a first clamp to a first spinous process of a first vertebra comprises the use of cement, epoxy, banding, or small screws.

Another embodiment includes a method which includes positioning a fusion member in a space between the first spinous process and the second spinous process, and compressing the fusion member between the first spinous process and the second spinous process. The method may also include disposing a fragment of bone within an interior portion of a volume defined by the fusion member. In a further embodiment, the method may include affixing a first anchor structure to a first spinous process, affixing a second anchor structure to a second spinous process, and applying tension between the first anchor and the second anchor structure.

Further embodiments of the method may include positioning the first and second anchor structures in proximity of the first and second spinous processes, aligning the first and second anchor structures, and clamping the first and second anchor structures to the first and second spinous processes respectively. In still further embodiments, the method includes coupling the first anchor structure to the second anchor structure by a tension member, and applying a tension load between the first anchor structure and the second anchor structure with the tension member.

Applying tension may further include threading a cable through one or more alignment guides, and securing the cable at a predetermined tension load. In such an embodiment, the one or more alignment guides may be integrated with at least one of the first anchor structure, the second anchor structure, and the fusion member.

BRIEF DESCRIPTION OF THE FIGURES

While exemplary embodiments of the present invention have been shown and described in detail below, it will be clear to the person skilled in the art that changes and modifications may be made without departing from the scope of the invention. As such, that which is set forth in the following description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, different materials of construction may be used for the clamps or coupling members employed in the kit or system. Furthermore, the shape of individual clamps or coupling members may also be altered.

Figure 1A:
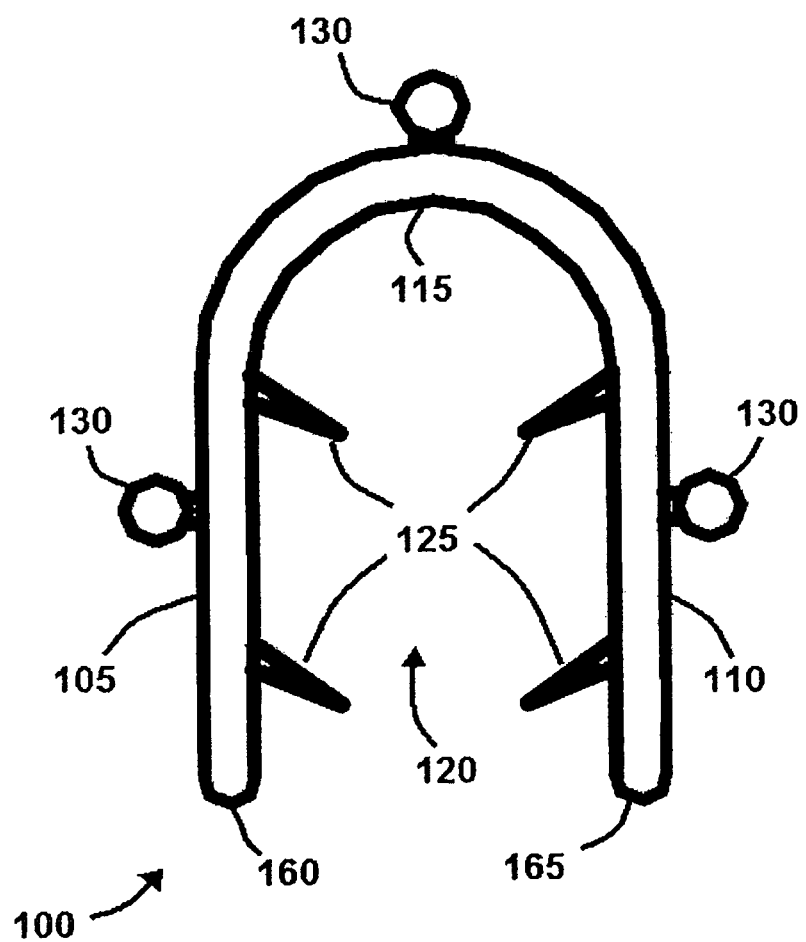

In the following Detailed Description of Disclosed Embodiments, various features are grouped together in several embodiments for the purpose of streamlining the disclosure. This method of disclosure is not to be interpreted as reflecting an intention that exemplary embodiments of the invention require more features than are expressly recited in each claim. Rather, as the following claims reflect, inventive subject matter lies in less than all features of a single disclosed embodiment. Thus, the following claims are hereby incorporated into the Detailed Description of Exemplary Embodiments, with each claim standing on its own as a separate embodiment.

Identical reference numerals do not necessarily indicate an identical structure. Rather, the same reference numeral may be used to indicate a similar feature or a feature with similar functionality. Not every feature of each embodiment is labeled in every figure in which that embodiment appears, in order to keep the figures clear. Similar reference numbers (e.g., those that are identical except for the first numeral) are used to indicate similar features in different embodiments.

FIG. 1A is an end view of a clamp according to a first exemplary embodiment of the present disclosure.

Figure 1B:
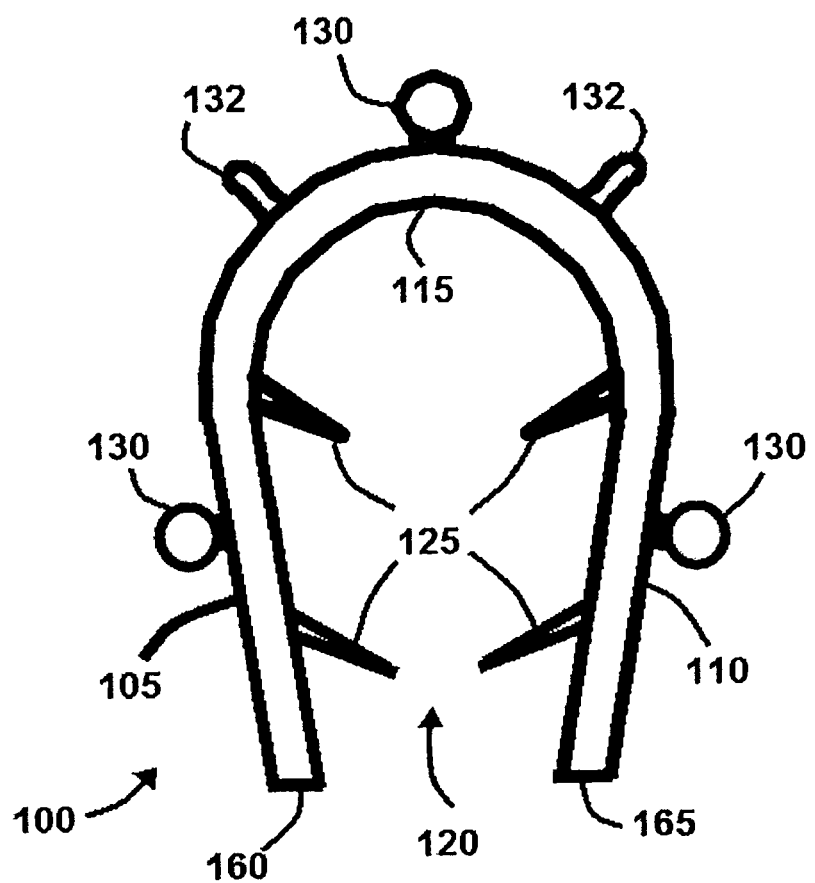

FIG. 1B is an end view of a clamp according to a second exemplary embodiment of the present disclosure.

Figure 1C:
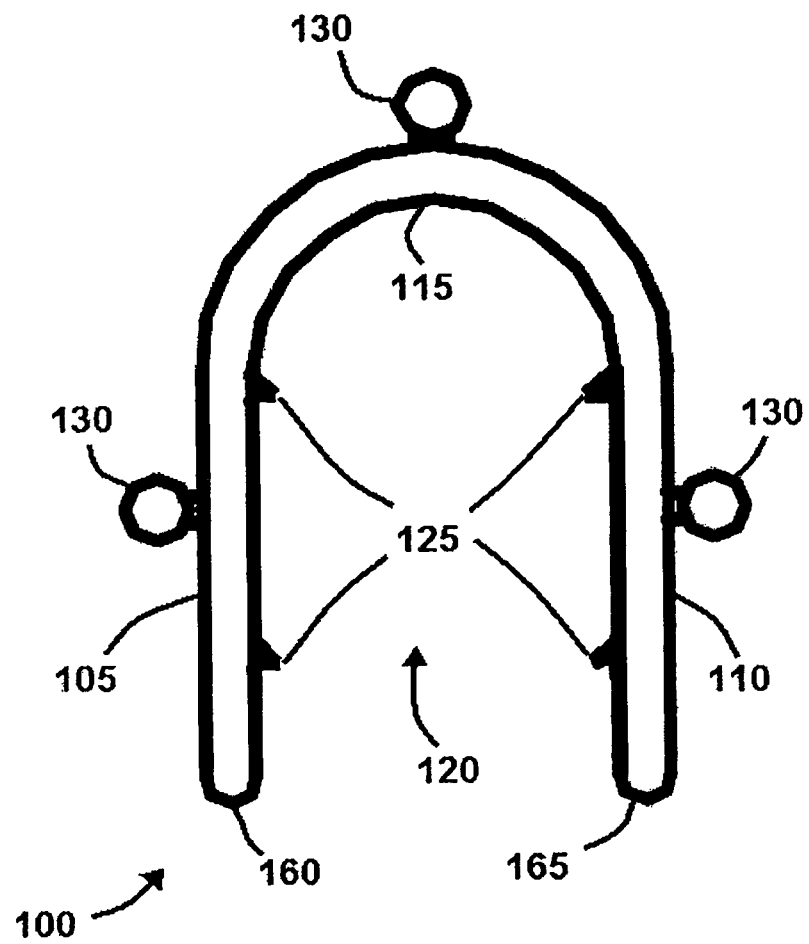

FIG. 1C is an end view of a clamp according to a third exemplary embodiment of the present disclosure.

Figure 2:
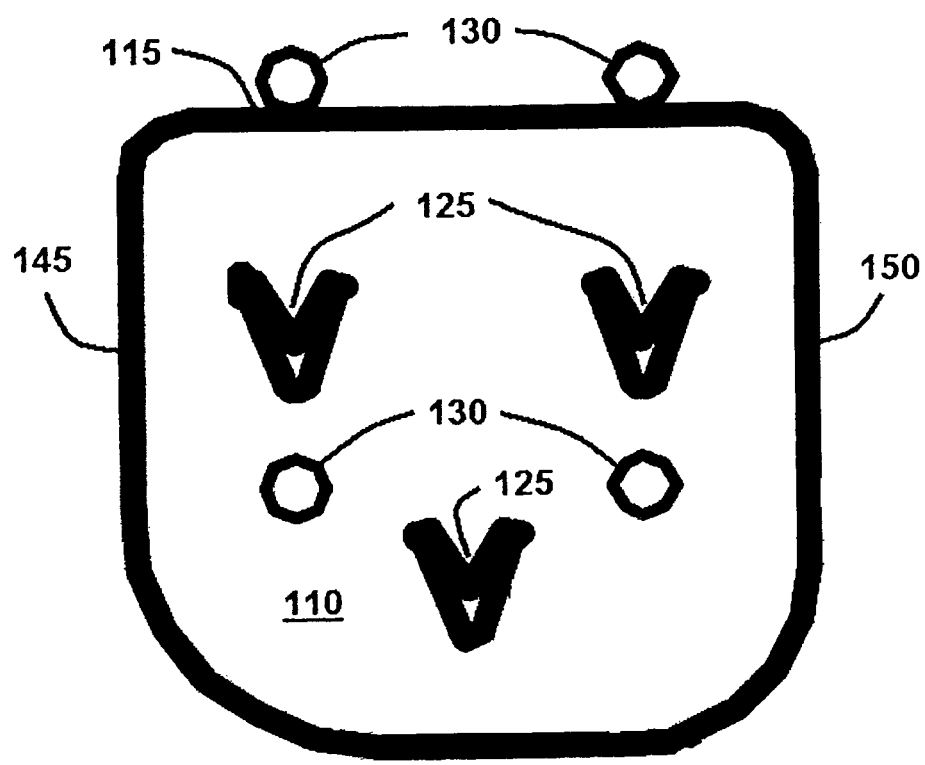

FIG. 2 is a side view of a clamp according to an exemplary embodiment of the present disclosure.

Figure 3:
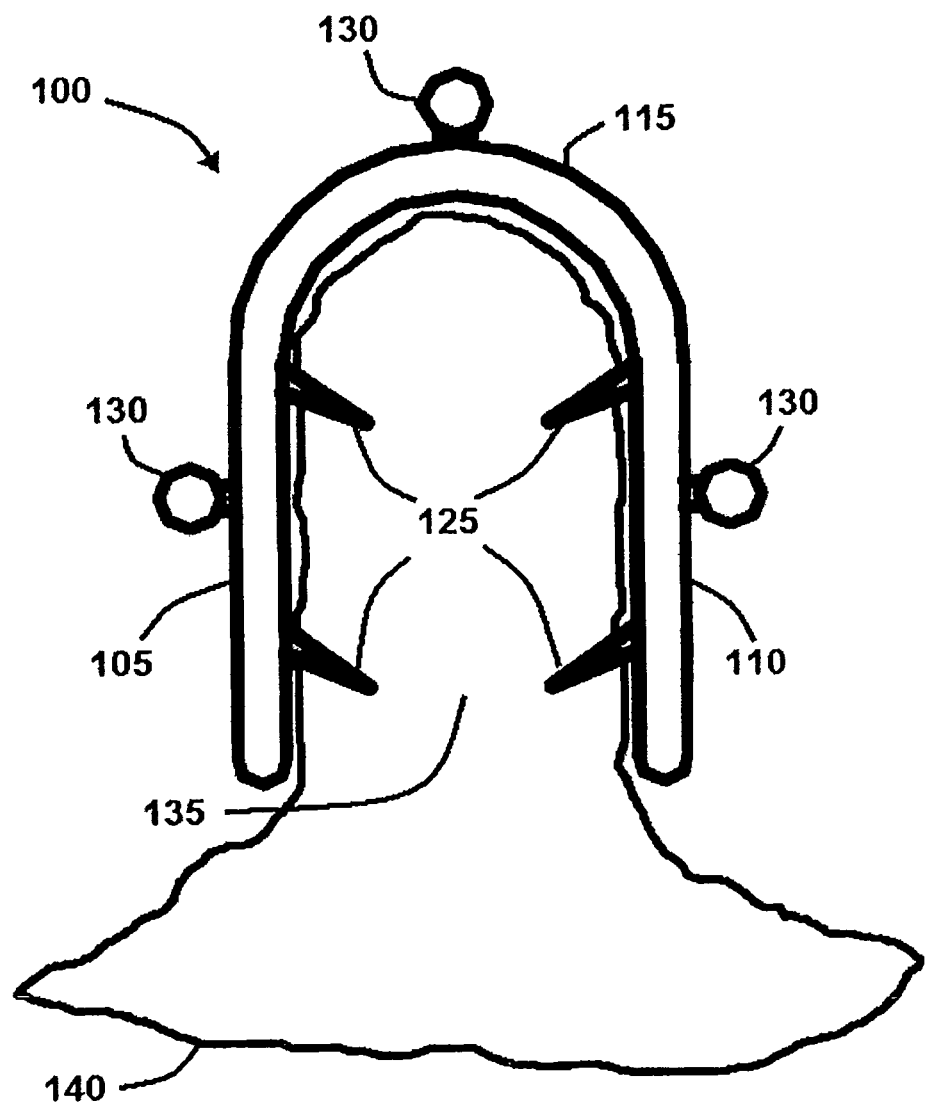

FIG. 3 is an end view of a clamp installed on a spinous process according to an exemplary embodiment of the present disclosure.

Figure 4A:
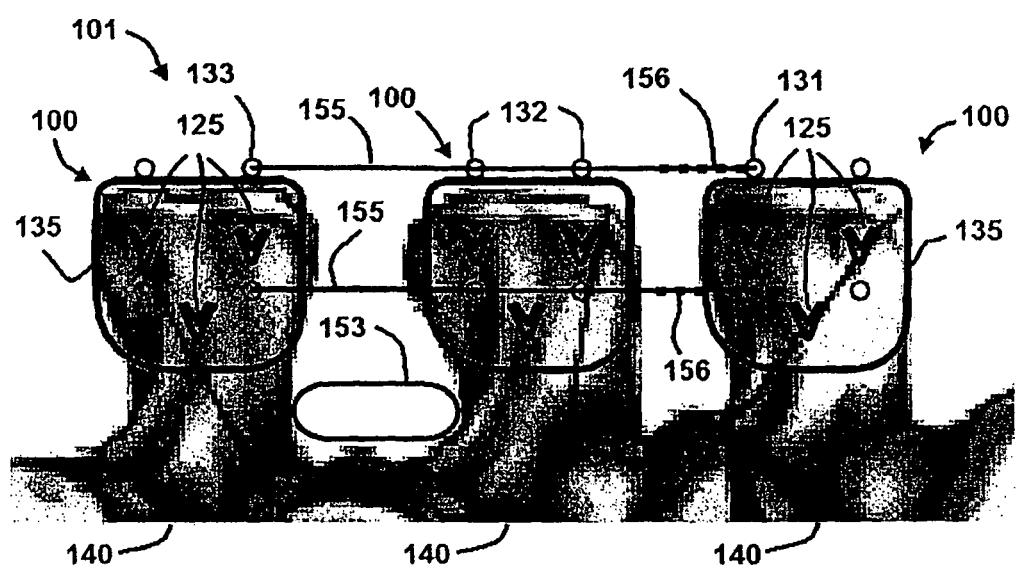

FIG. 4A is side view of a system of clamps installed on a series of spinous processes according to an exemplary embodiment of the present disclosure.

Figure 4B:
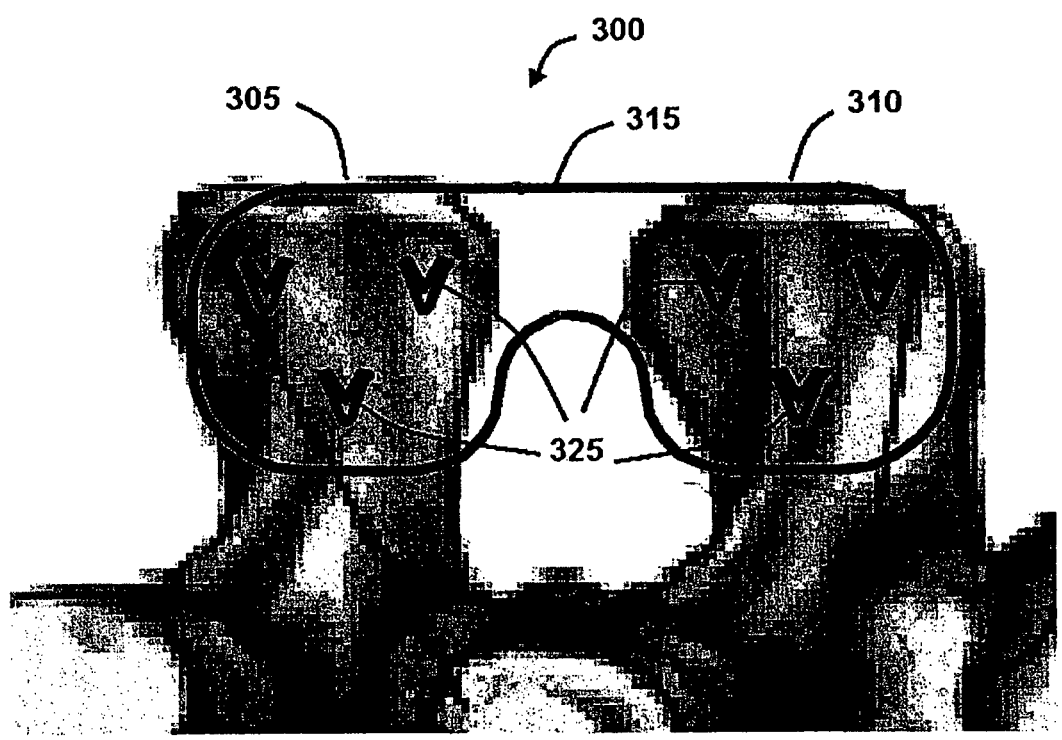

FIG. 4B is side view of a clamp installed on a pair of spinous processes according to an exemplary embodiment of the present disclosure.

Figure 5:
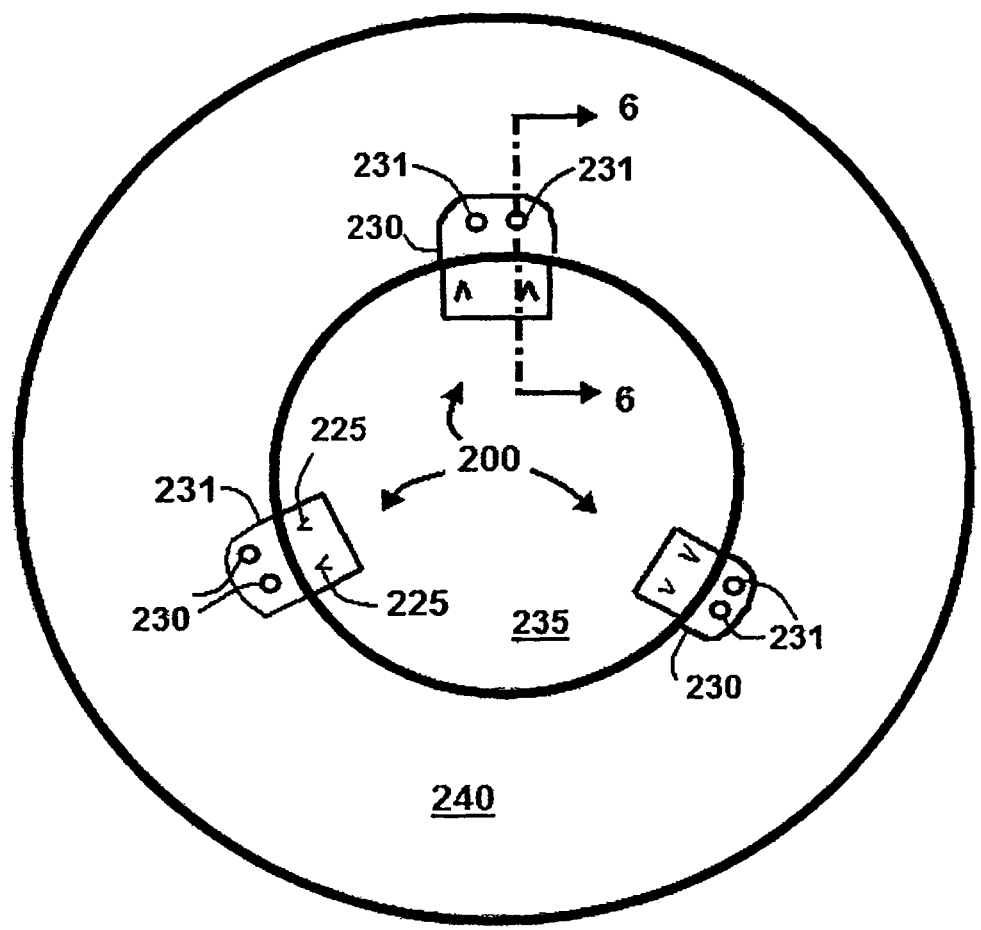

FIG. 5 is a top view of a system of clamps installed on a calvarial flap according to an exemplary embodiment of the present disclosure.

Figure 6:
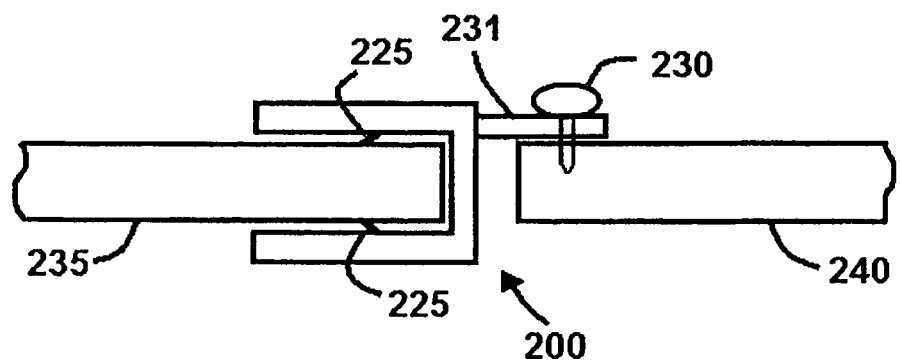

FIG. 6 is a section view of the exemplary embodiment of FIG. 5.

Figure 7:
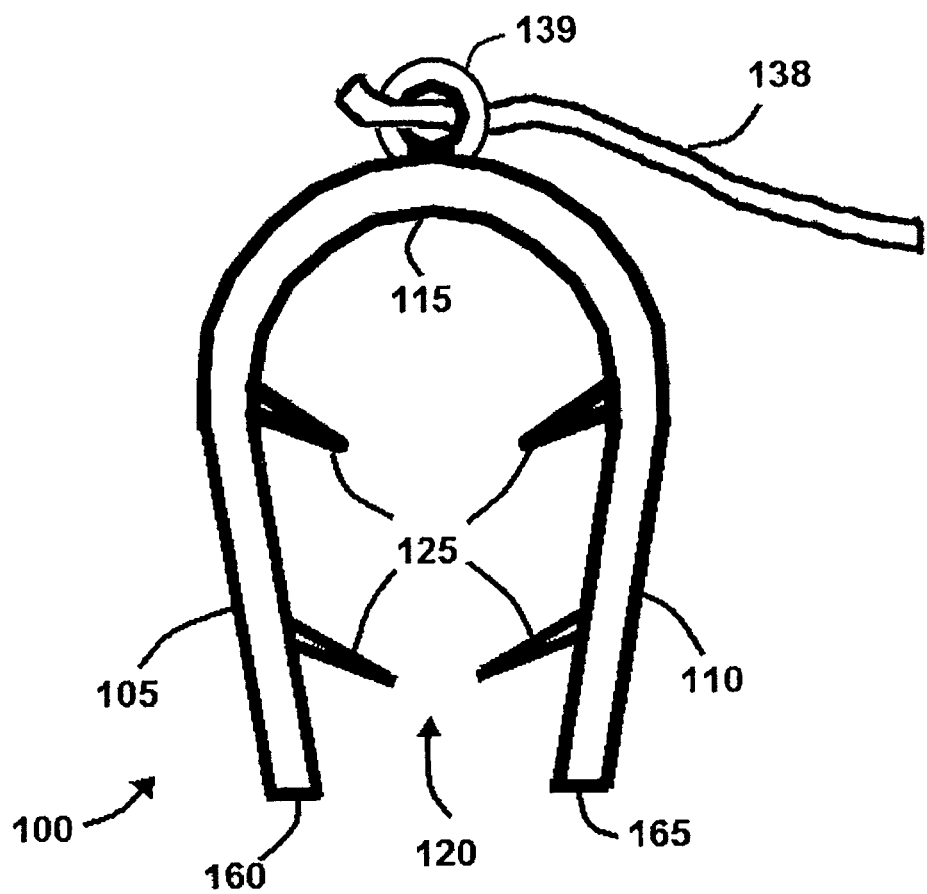

FIG. 7 is an end view of a clamp according to an exemplary embodiment of the present disclosure.

Figure 8:
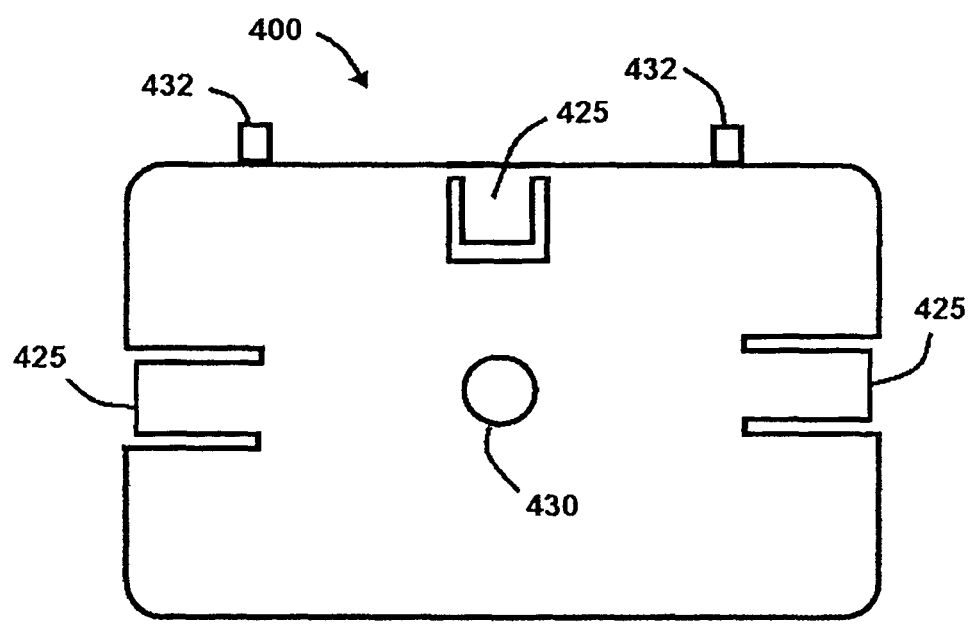

FIG. 8 is a side view of a clamp according to an exemplary embodiment of the present disclosure.

Figure 9:
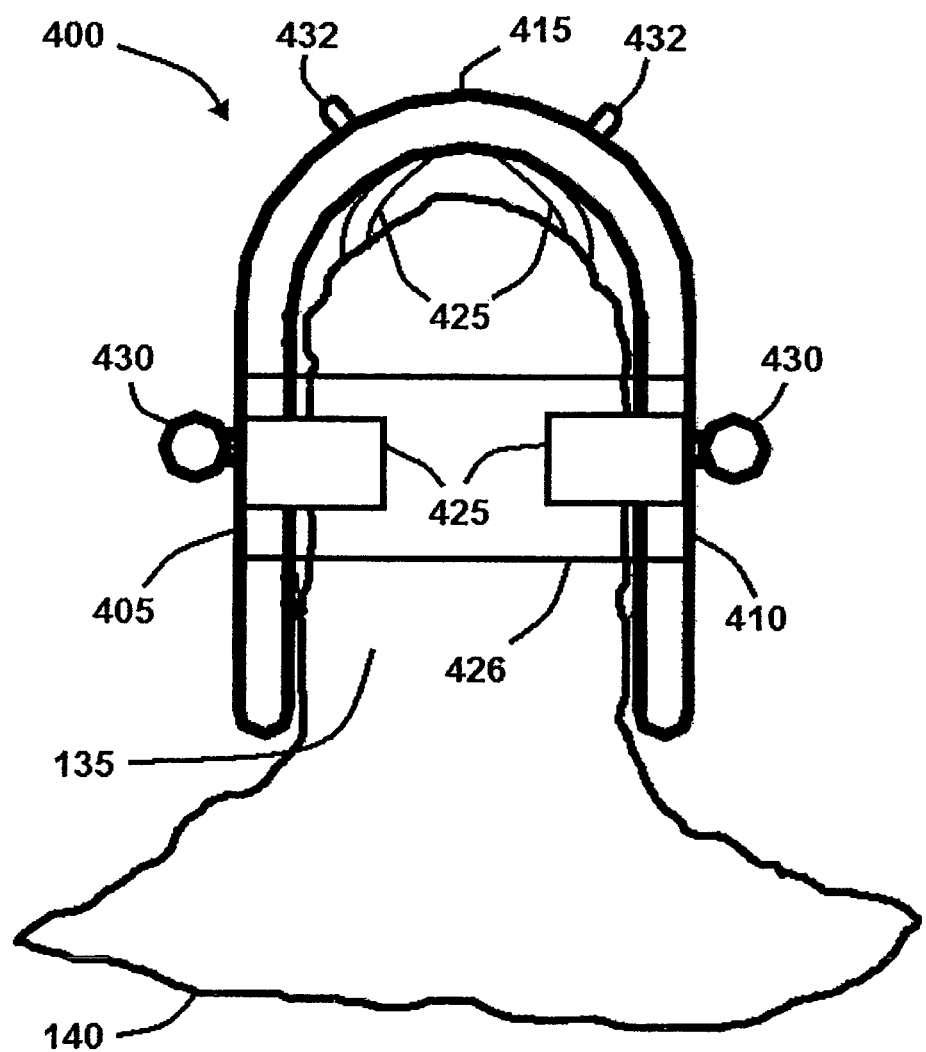

FIG. 9 is an end view of a clamp installed on a spinous process according to an exemplary embodiment of the present disclosure.

Figure 10:
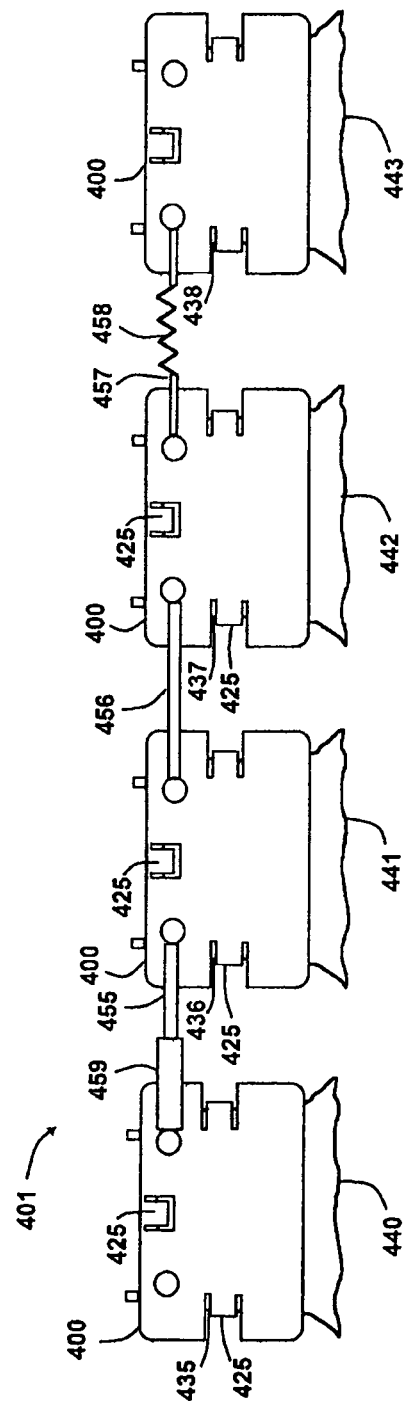

FIG. 10 is a side view of a system of clamps installed on a series of spinous processes according to an exemplary embodiment of the present disclosure.

Figure 11:
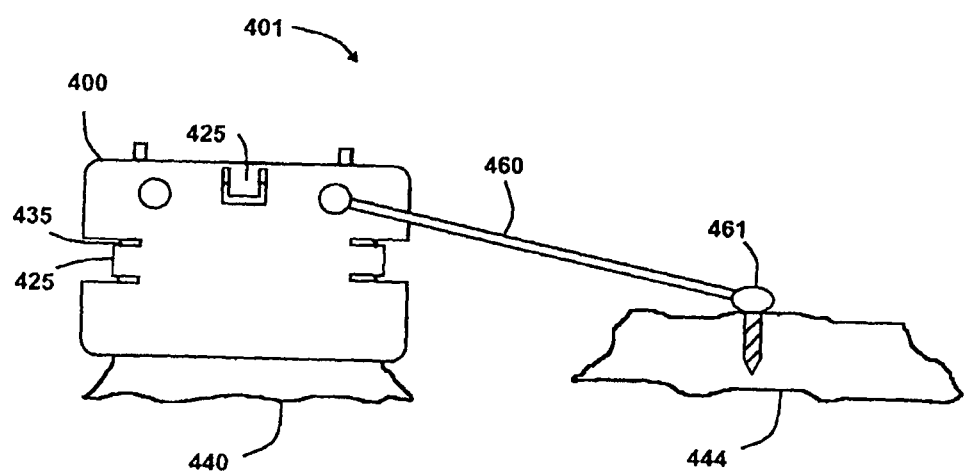

FIG. 11 is a side view of a clamp installed on a spinous process according to an exemplary embodiment of the present disclosure.

Figure 12:
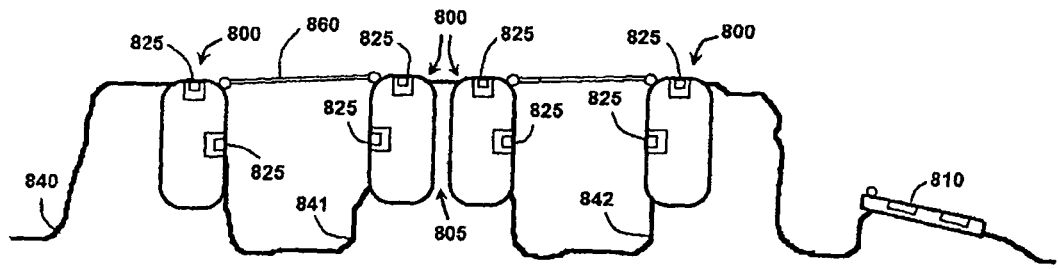

FIG. 12 is a side view of a system of clamps installed on a series of spinous processes according to an exemplary embodiment of the present disclosure.

Figure 13:
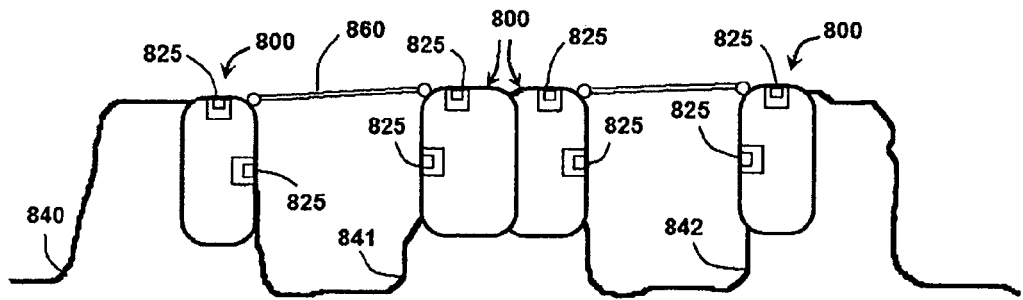
Figure 14:
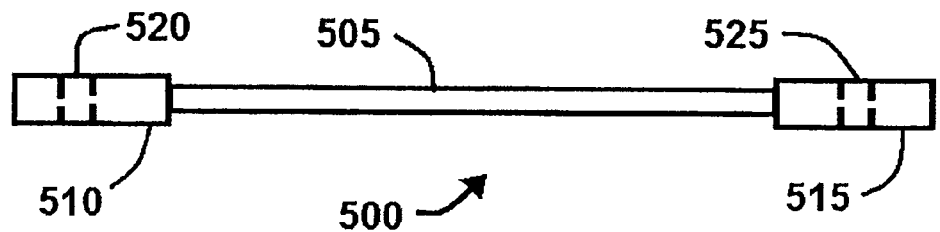

FIG. 13 is a side view of a system of clamps installed on a series of spinous processes according to an exemplary embodiment of the present disclosure FIG. 14 is a side view of a coupling member according to an exemplary embodiment of the present disclosure.

Figure 15:
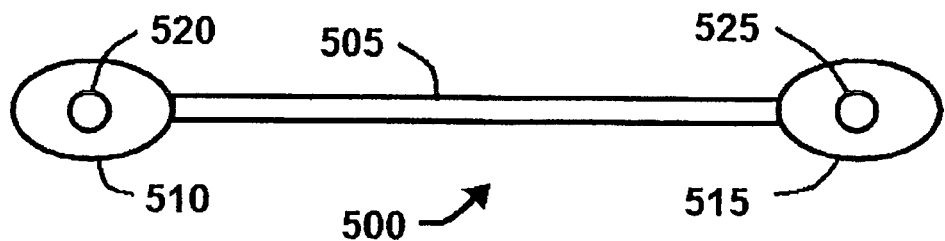

FIG. 15 is a top view of a coupling member according to an exemplary embodiment of the present disclosure.

Figure 16:
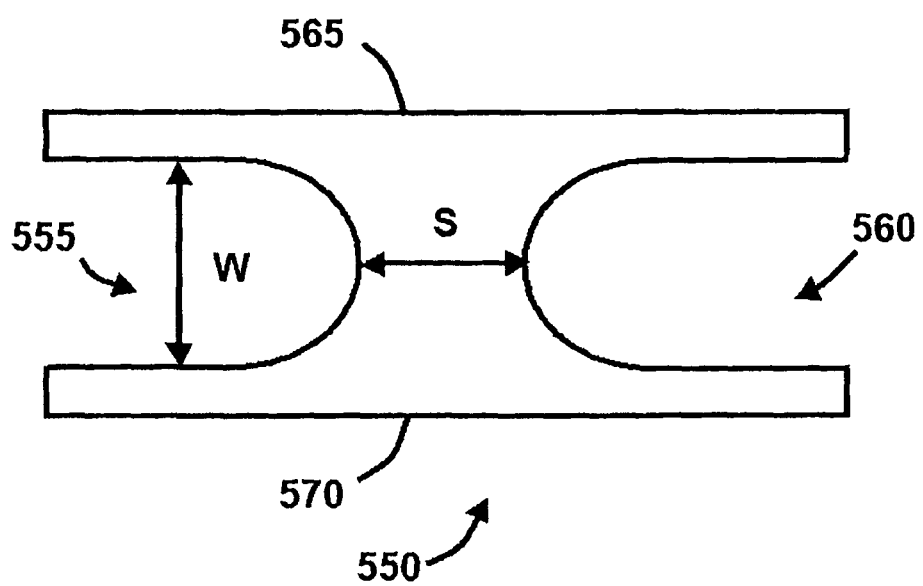

FIG. 16 is a top view of a coupling member according to an exemplary embodiment of the present disclosure.

Figure 17:
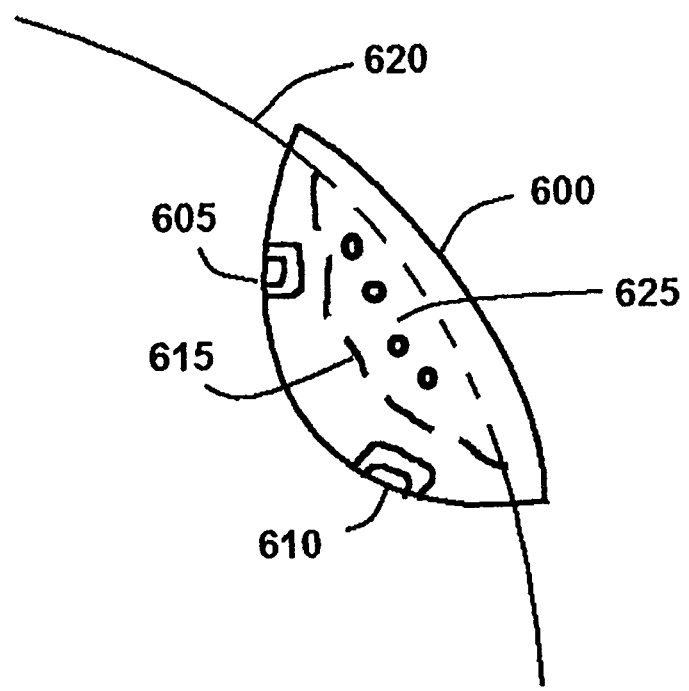

FIG. 17 is a side view of a clamp installed on a sacral iliac crest according to an exemplary embodiment of the present disclosure.

Figure 18:
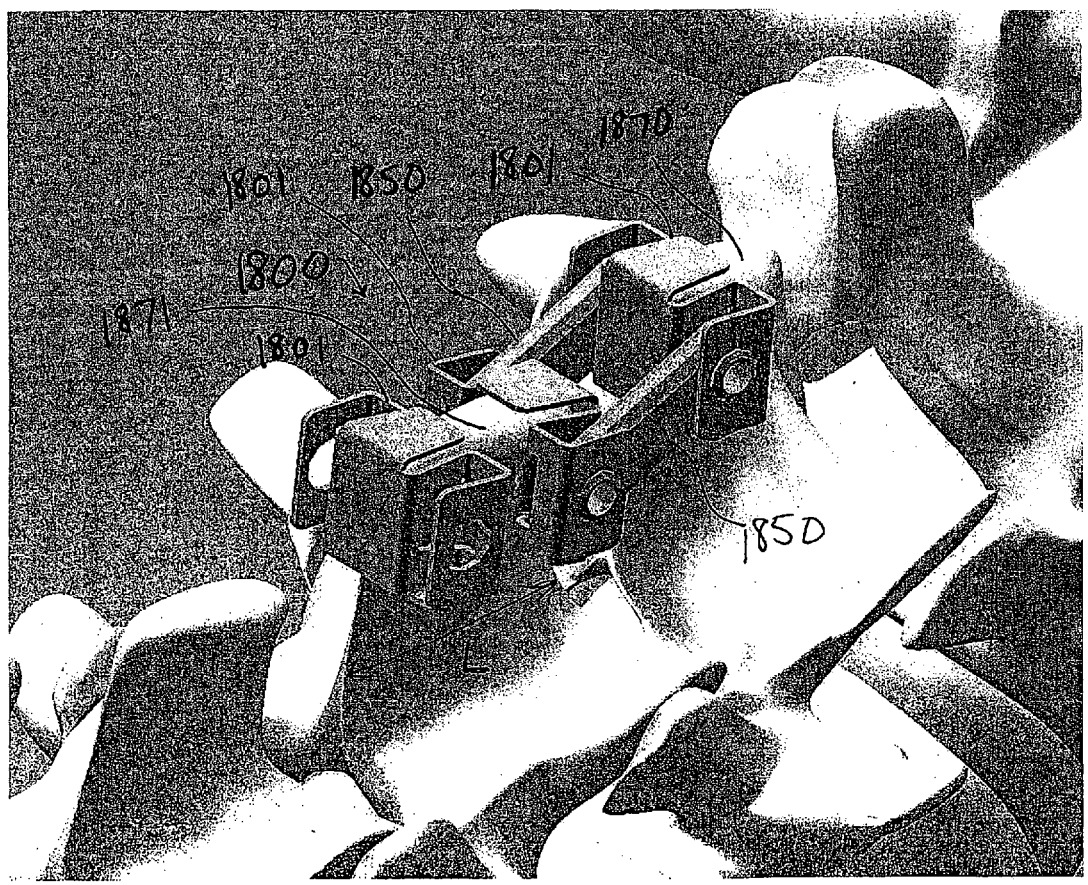
Figure 19:
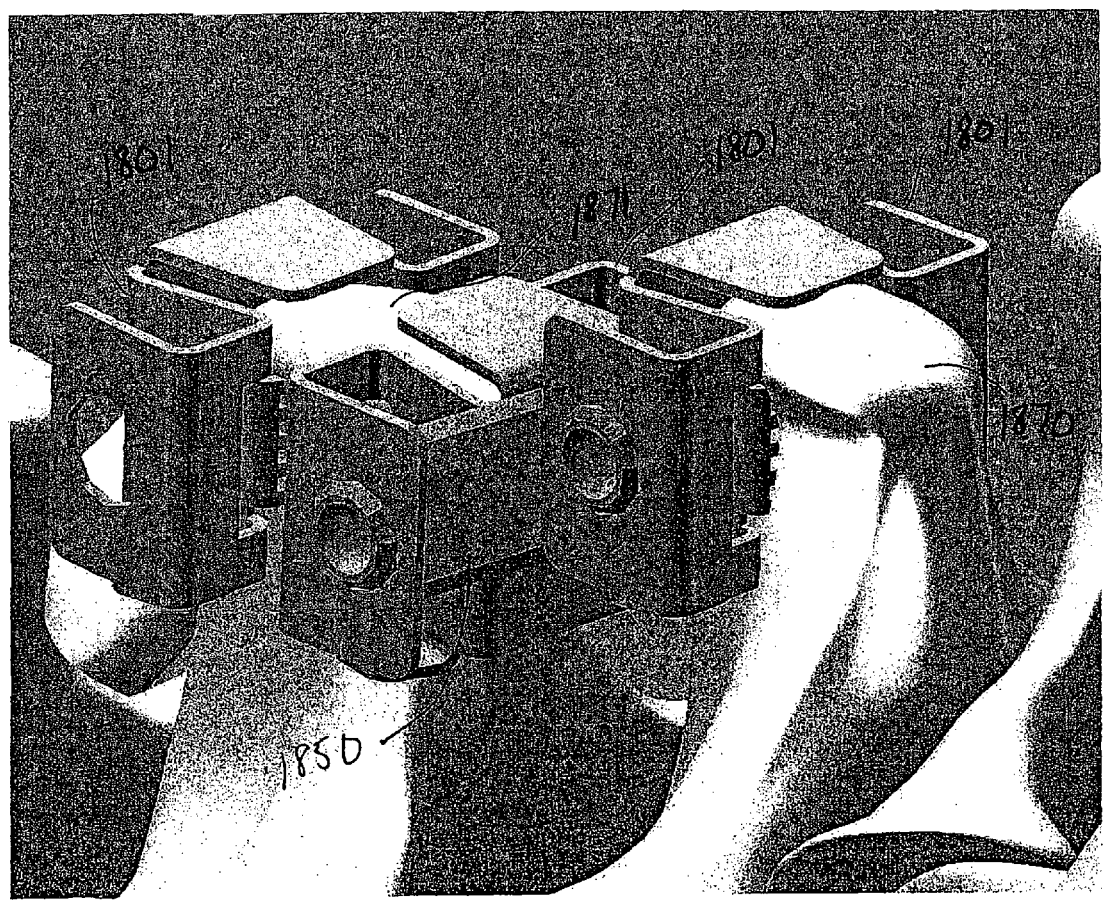

FIGS. 18-19 are perspective views of a clamp assembly according to an exemplary embodiment of the present disclosure.

Figure 20:
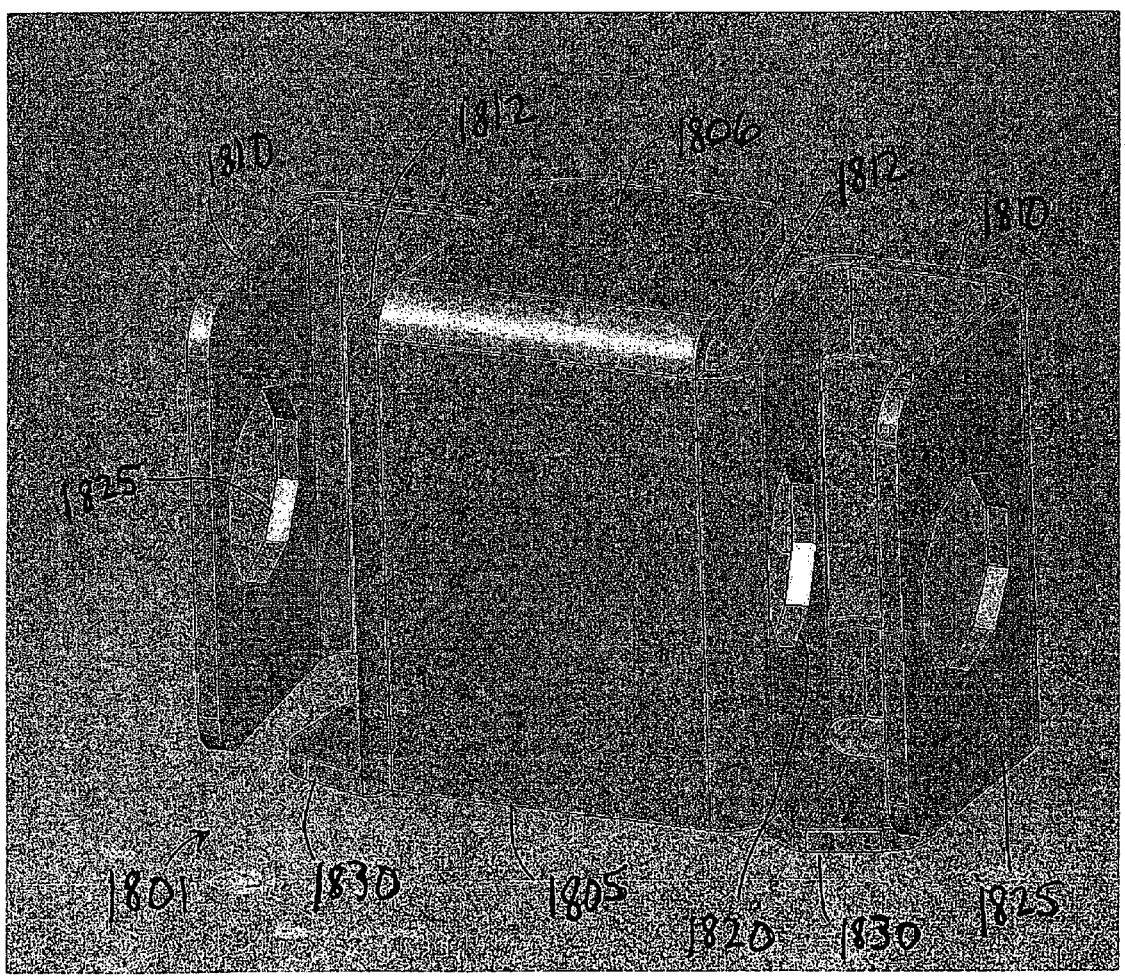
Figure 21:
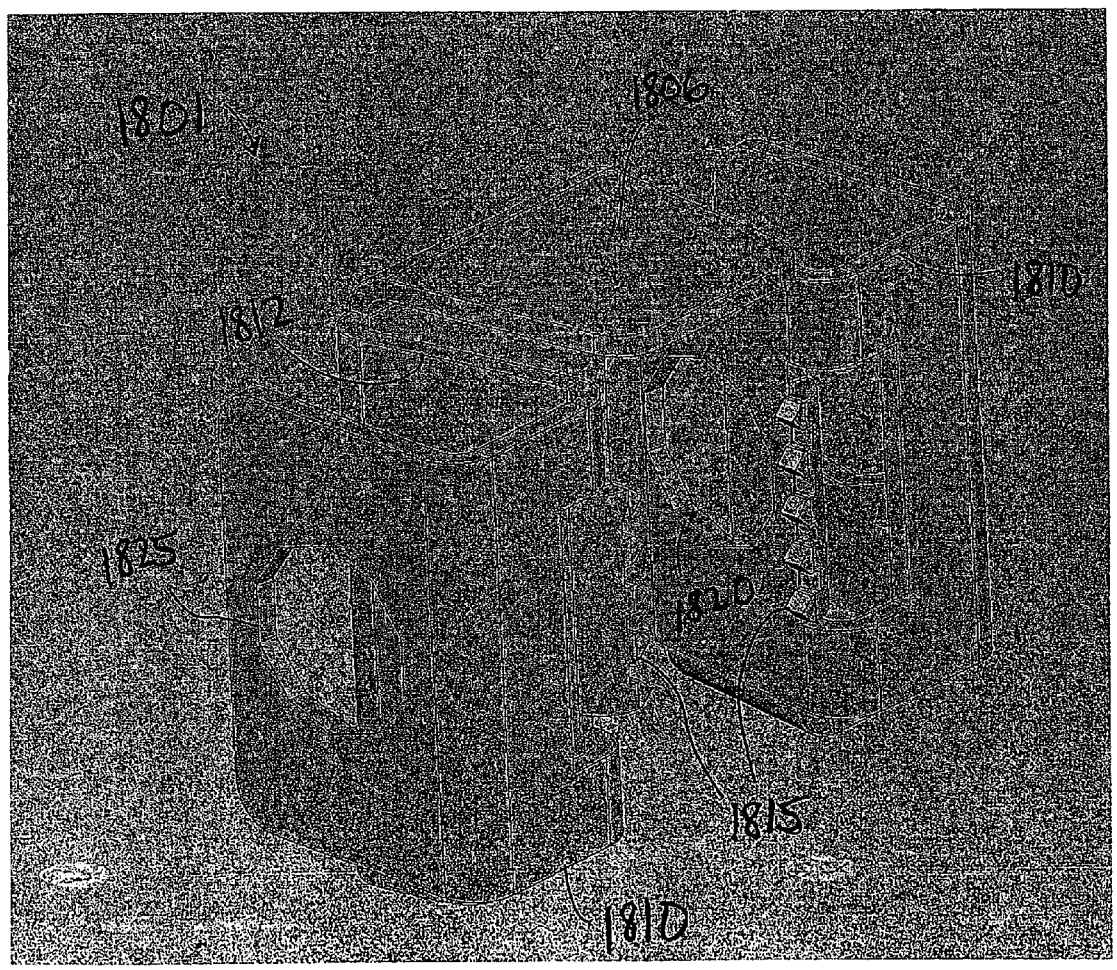

FIGS. 20-21 are perspective views of a clamp according to an exemplary embodiment of the present disclosure.

Figure 22:
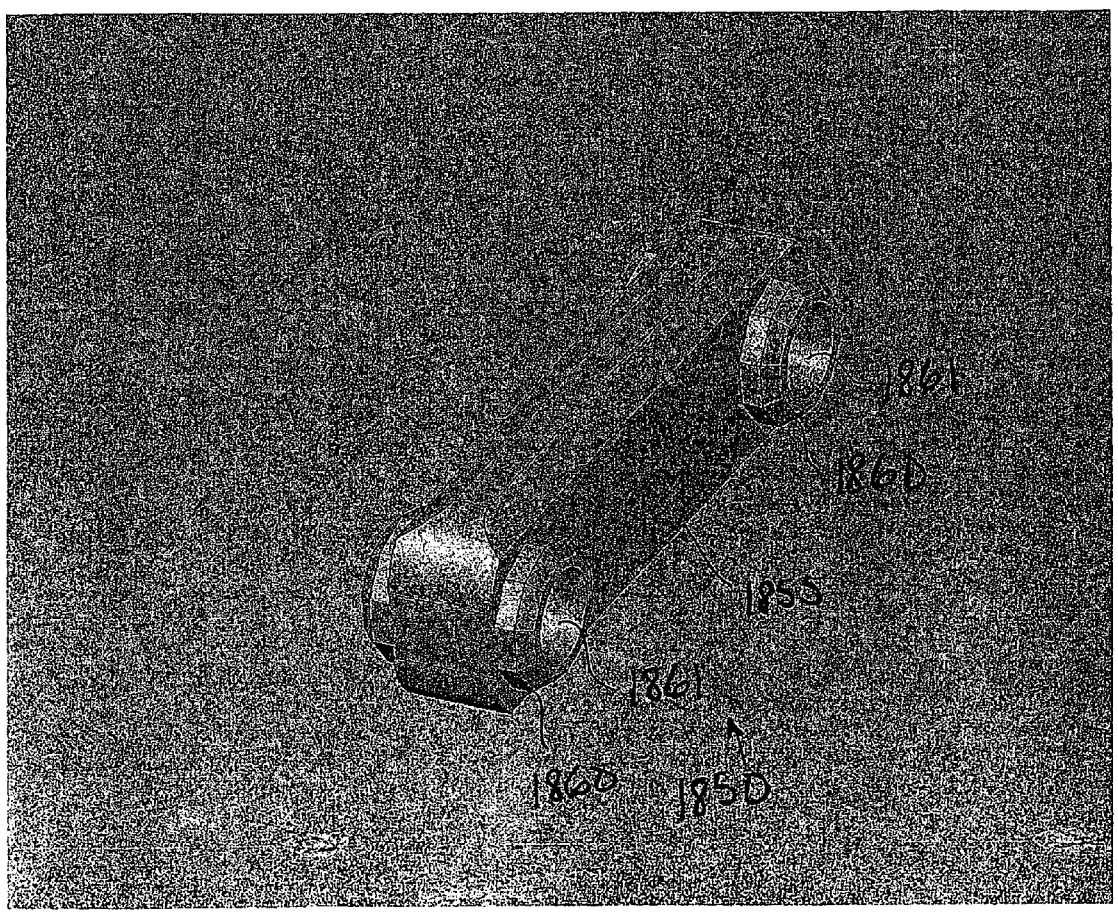
Figure 23:
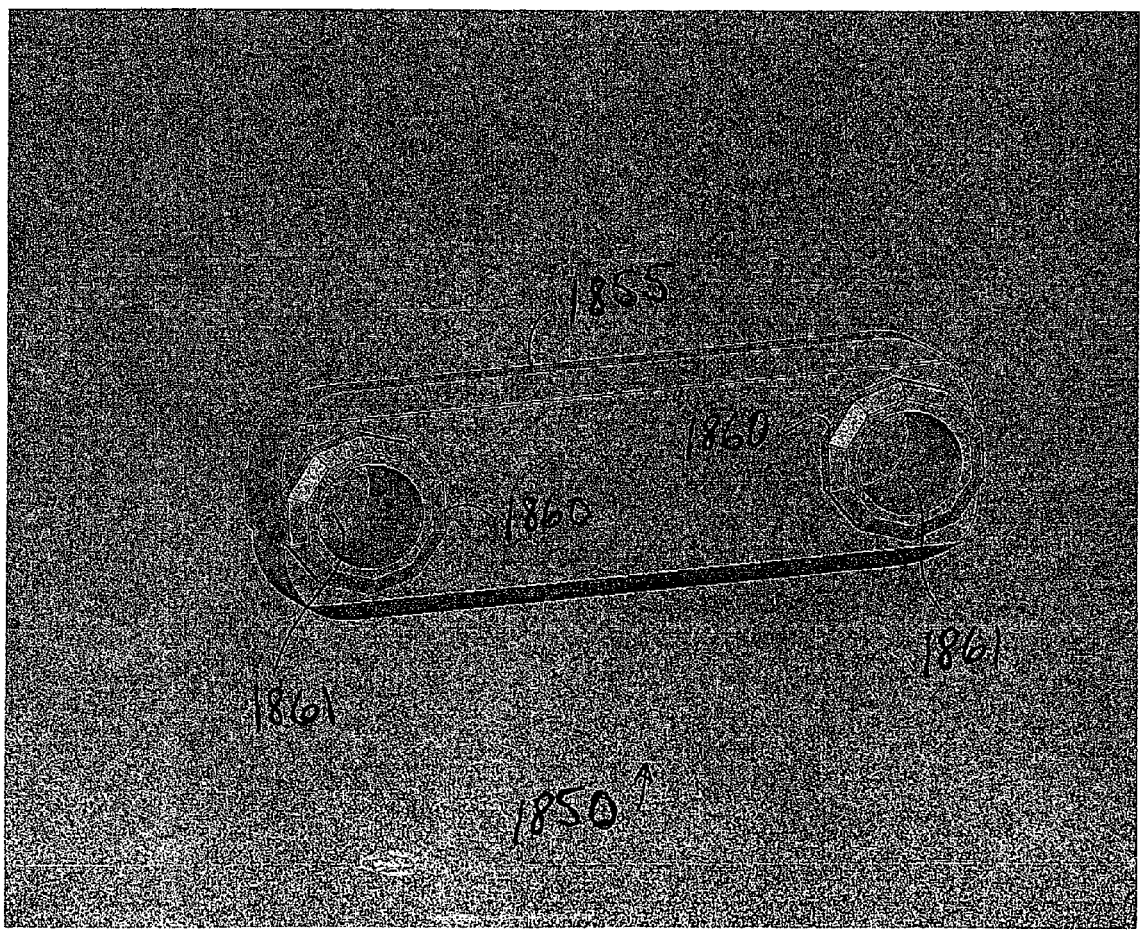

FIGS. 22-23 are perspective views of a coupling member according to an exemplary embodiment of the present disclosure.

Figure 24:
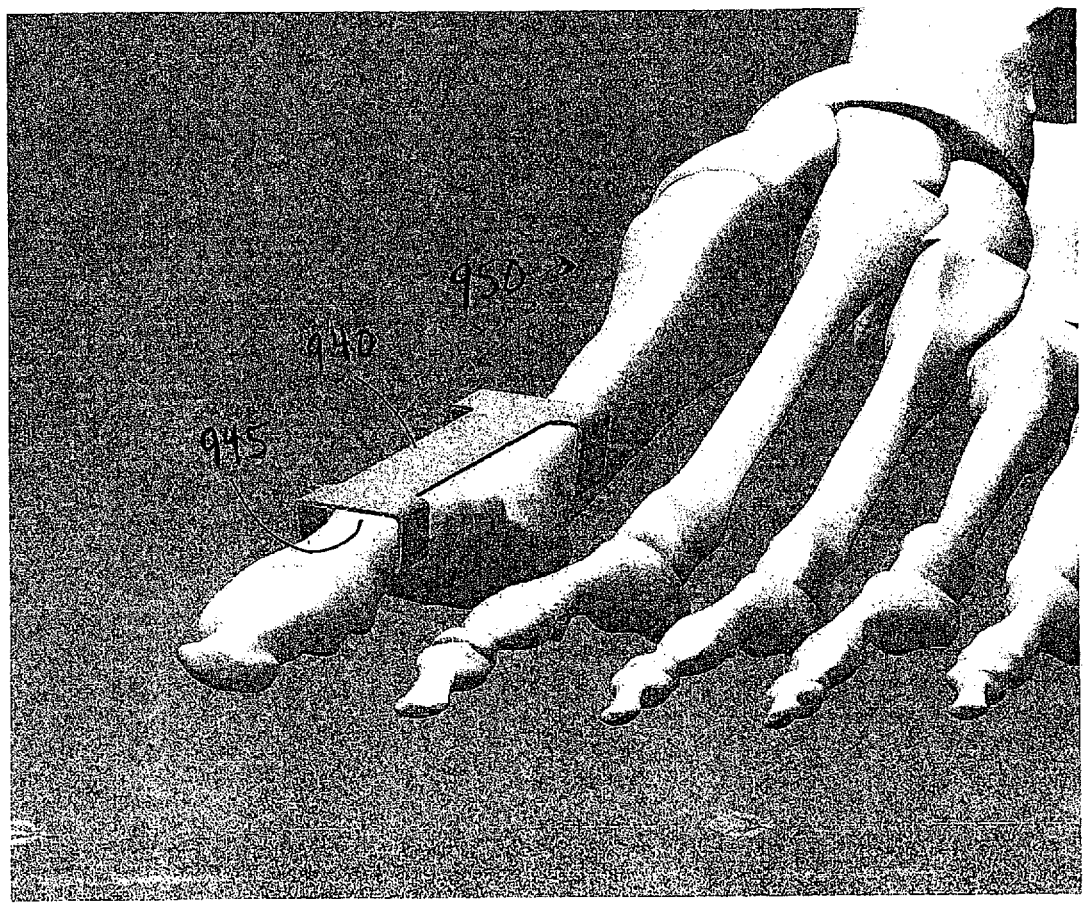

FIG. 24 is a perspective view of a clamp on a foot bone according to an exemplary embodiment of the present disclosure.

Figure 25:
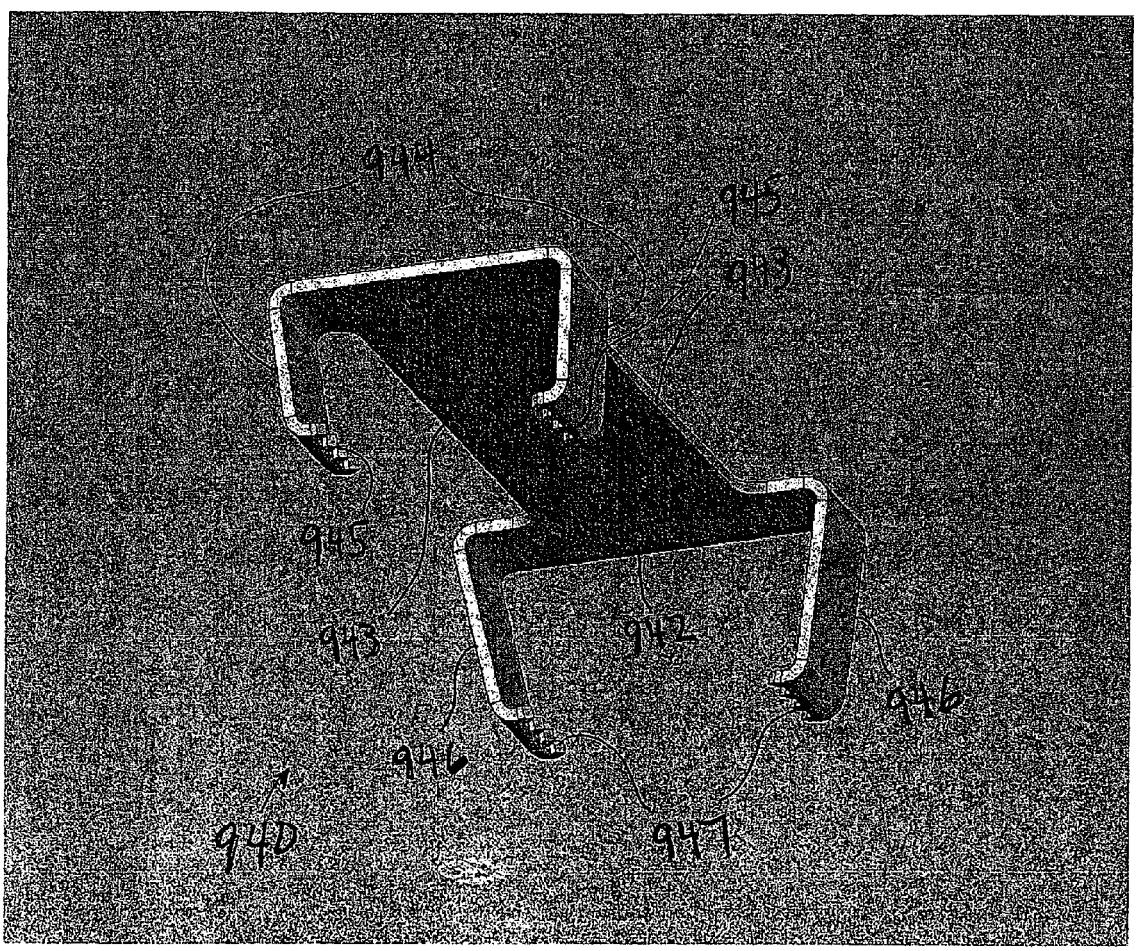

FIG. 25 is a perspective view of the clamp of FIG. 24.

Figure 26:
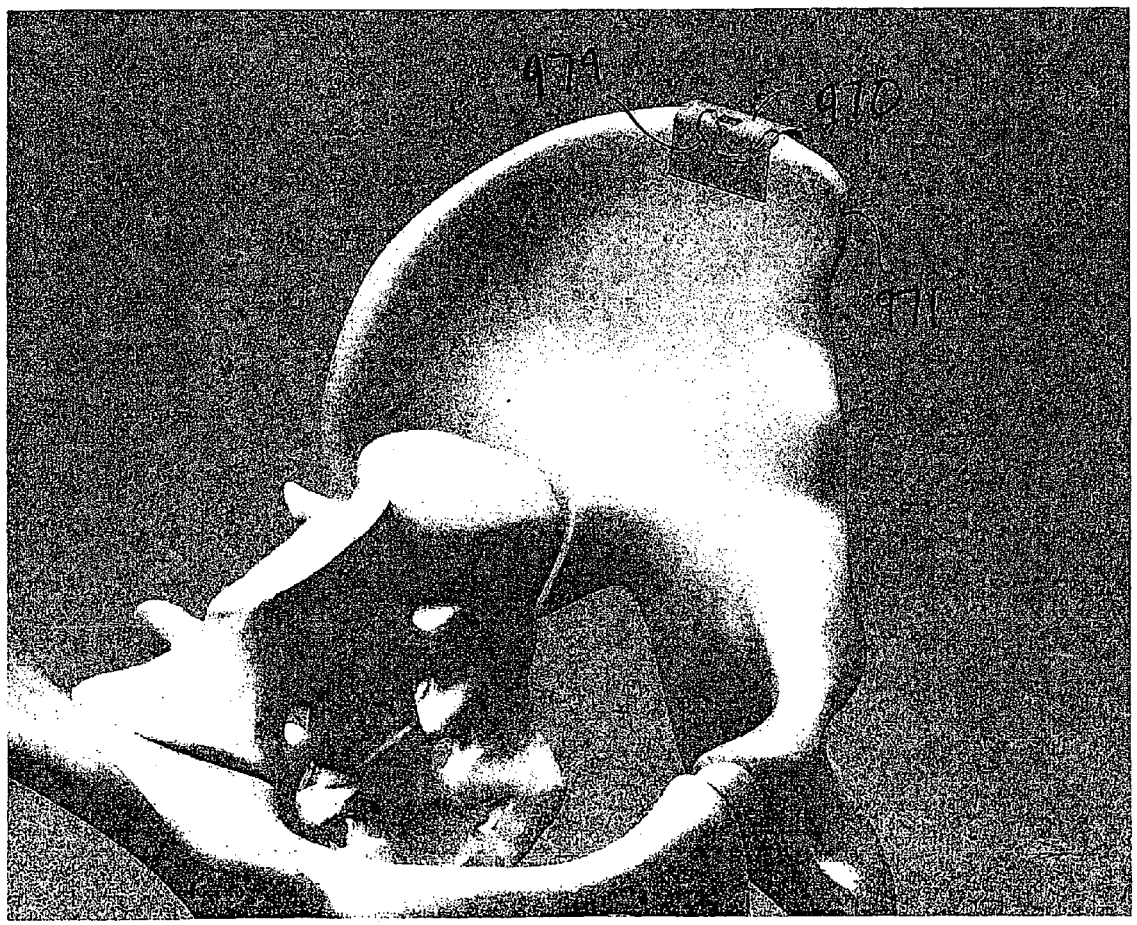

FIG. 26 is a perspective view of a clamp on a hip bone according to an exemplary embodiment of the present disclosure.

Figure 27:
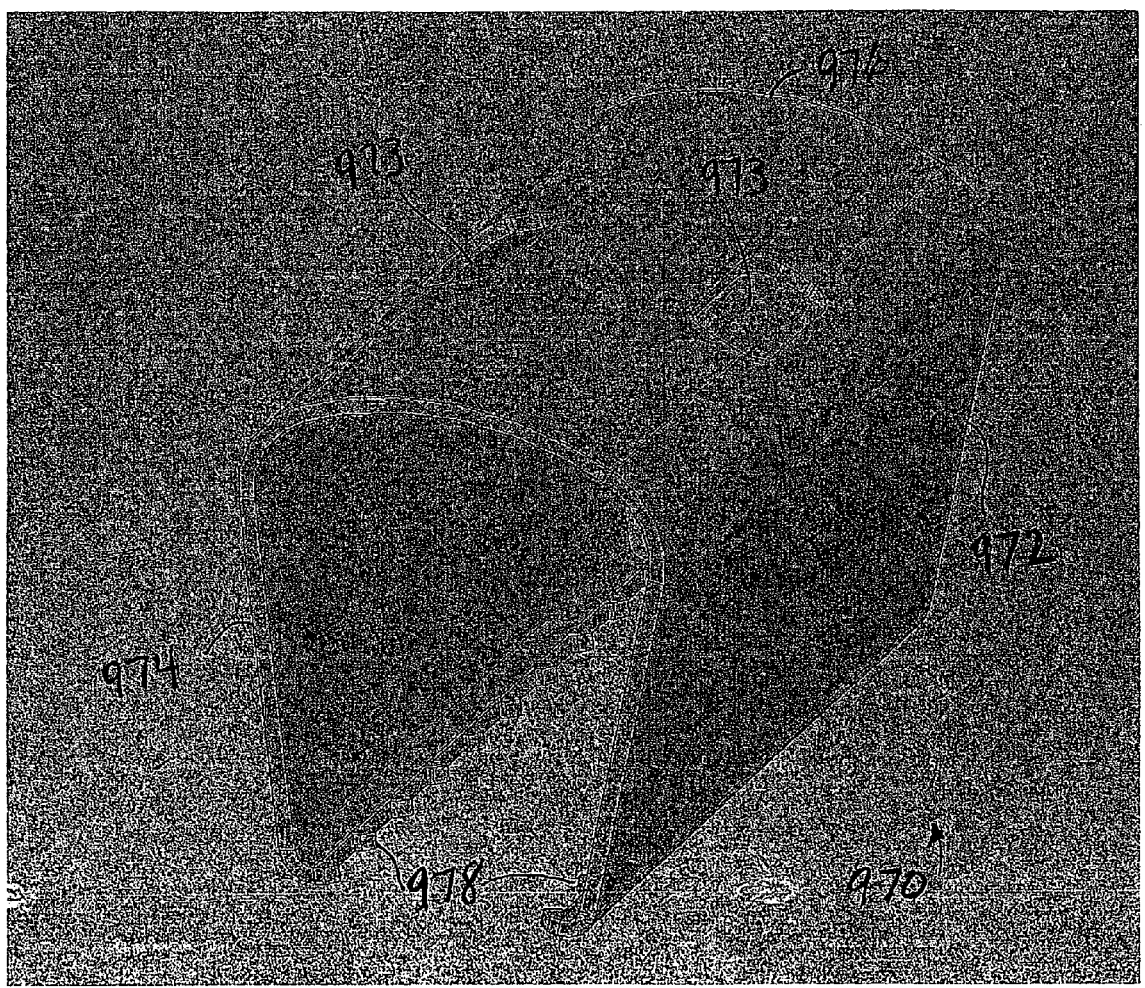

FIG. 27 is a perspective view of the clamp of FIG. 26.

Figure 28:

FIG. 28 is a perspective view of a clamp on a cranial flap according to an exemplary embodiment of the present disclosure.

Figure 29:
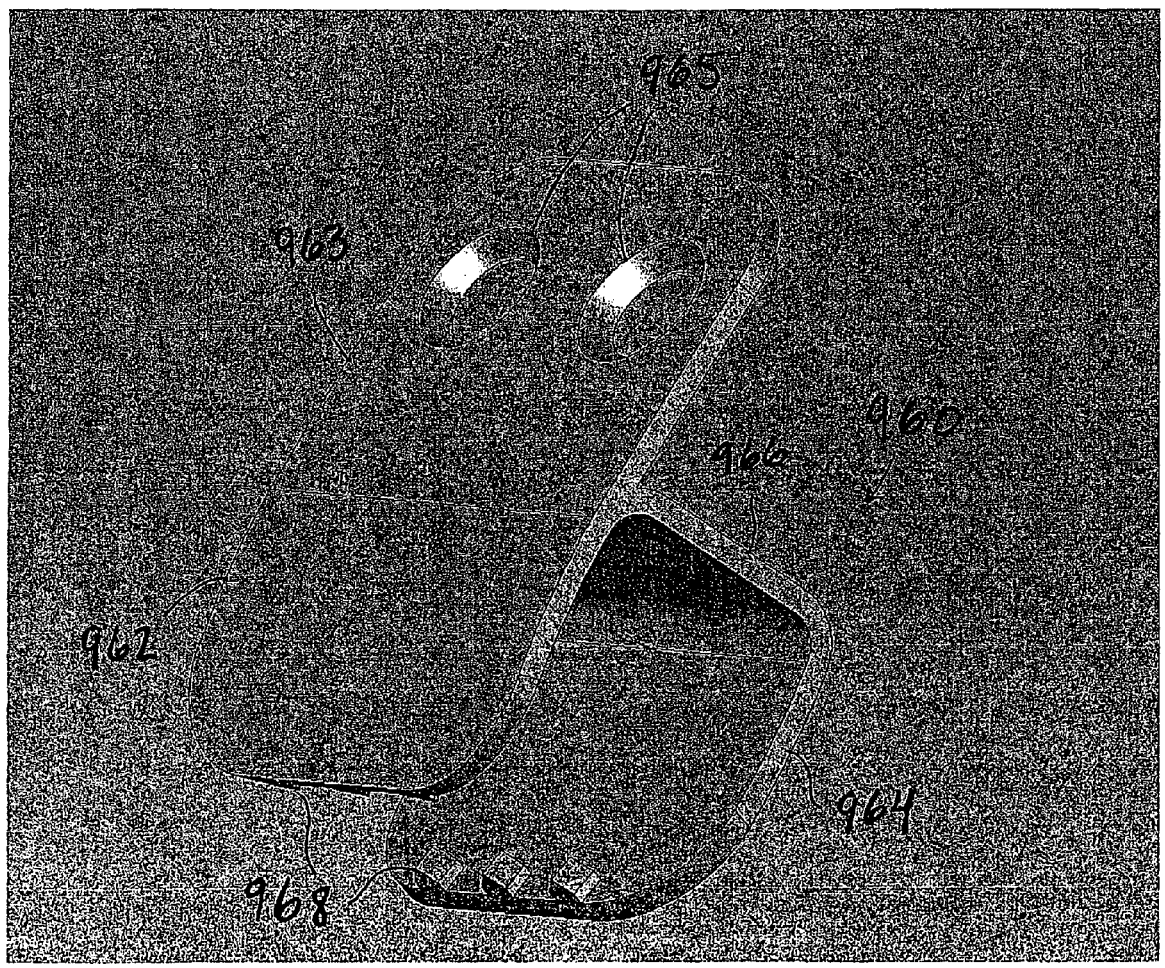

FIG. 29 is a perspective view of the clamp of FIG. 28.

Figure 30:
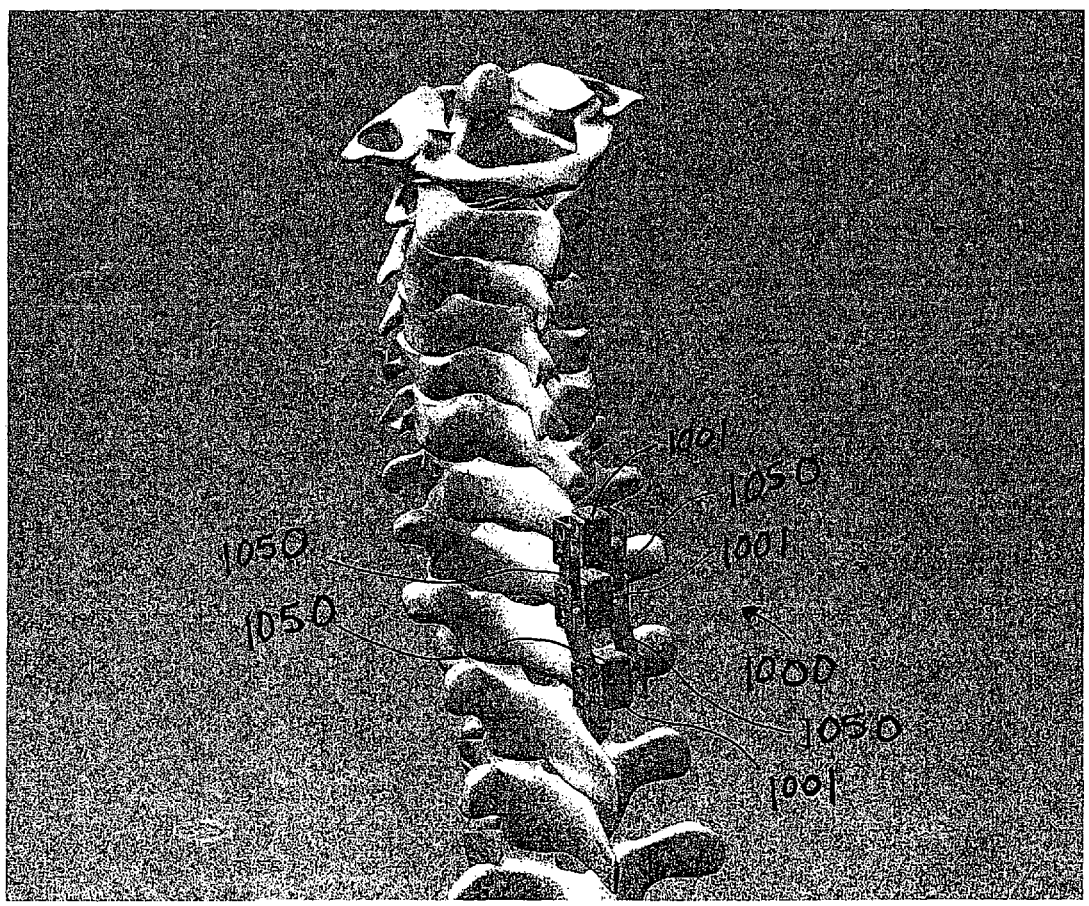
Figure 31:
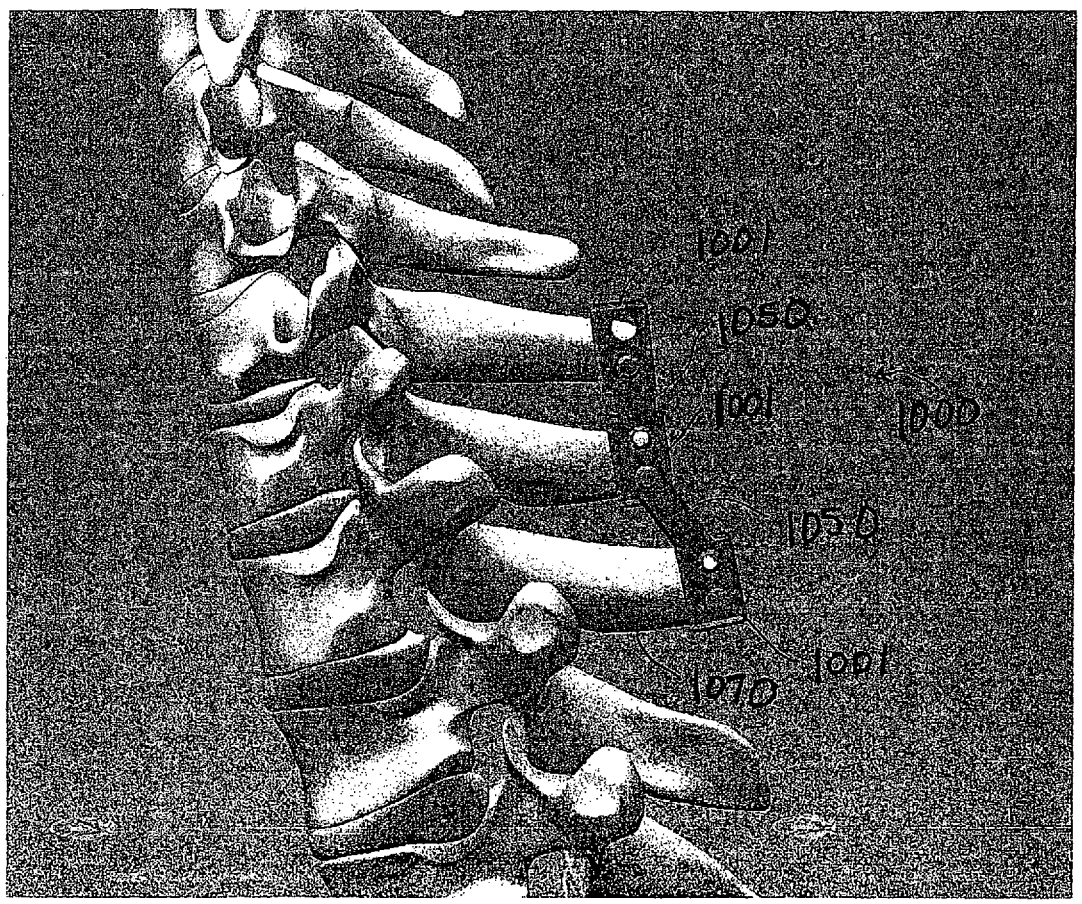

FIGS. 30-31 are perspective views of a clamp assembly according to an exemplary embodiment of the present disclosure.

Figure 32:
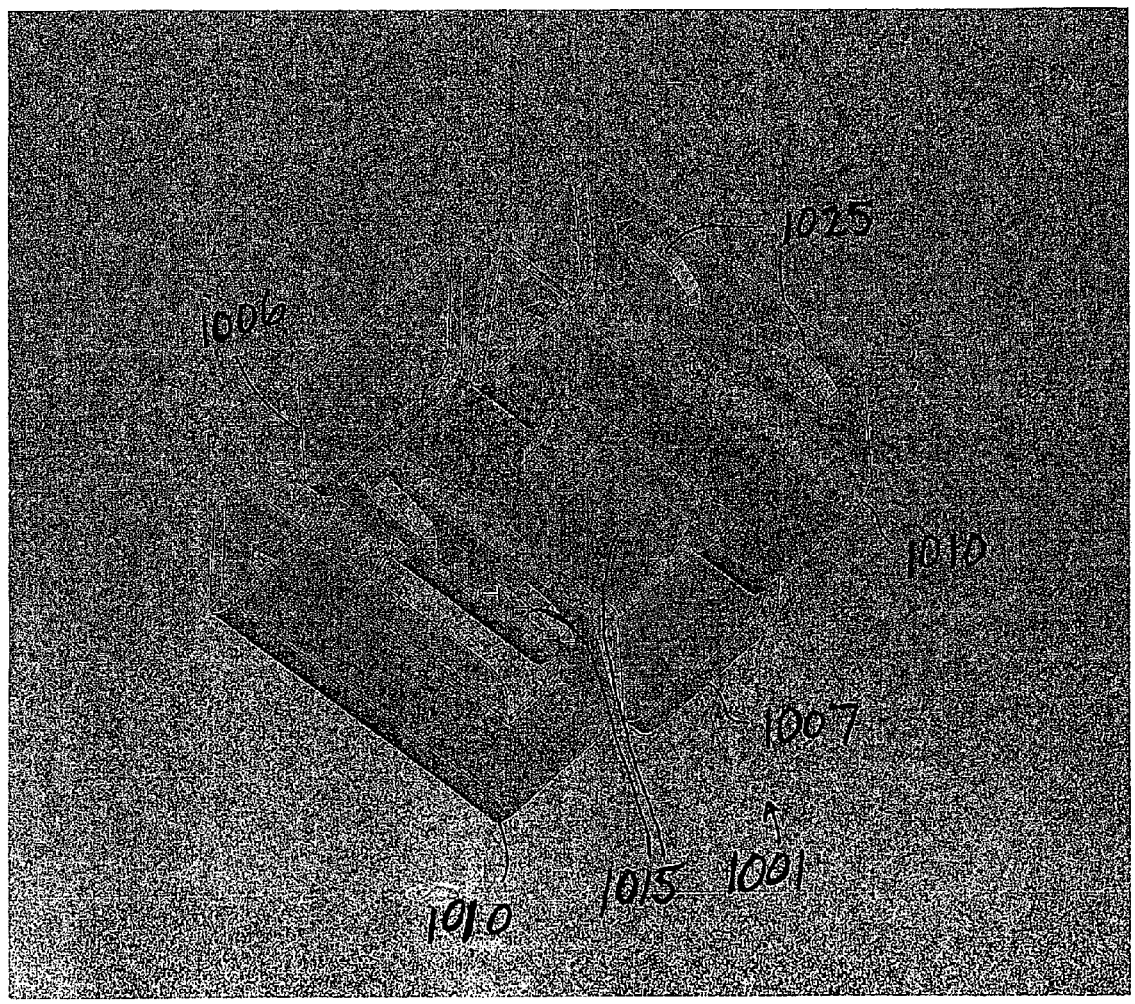
Figure 33:
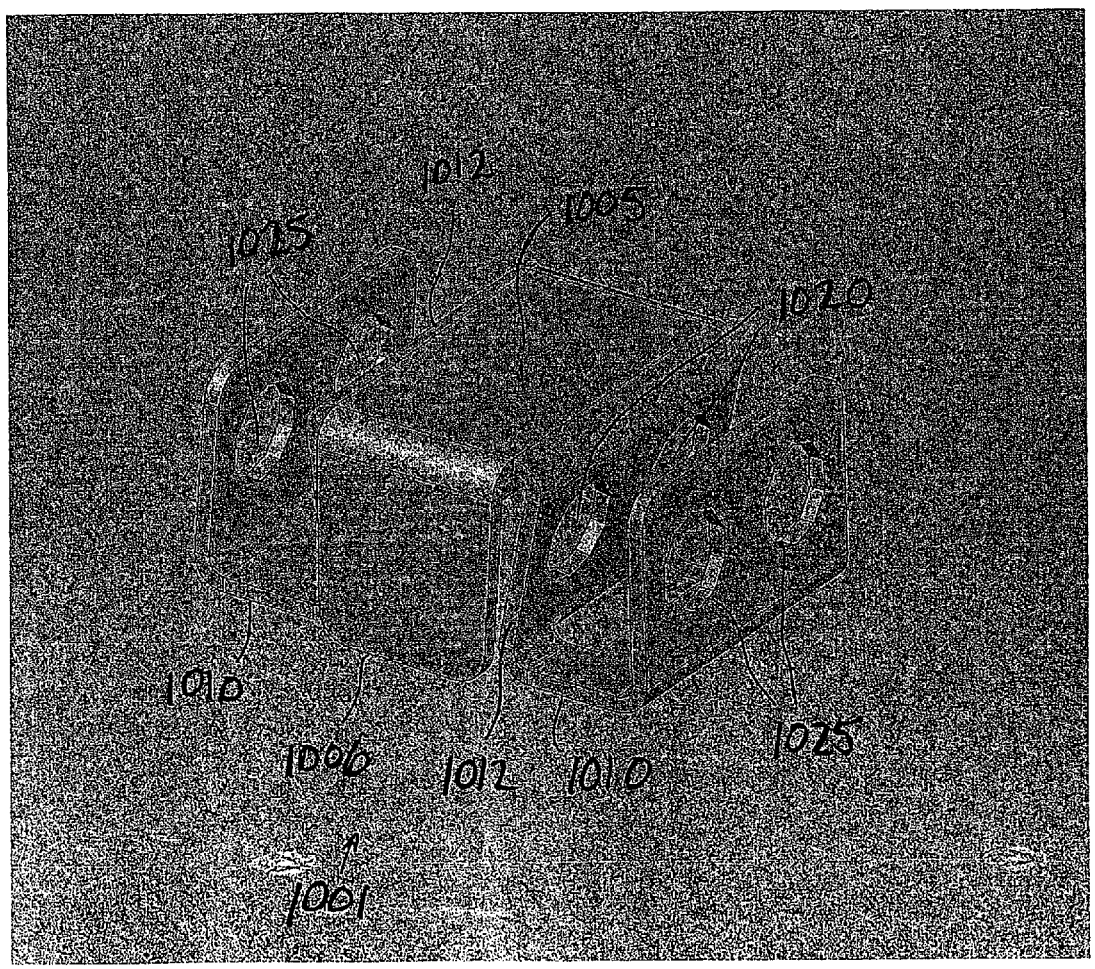

FIGS. 32-33 are a perspective views of the clamp of FIG. 28.

Figure 34:
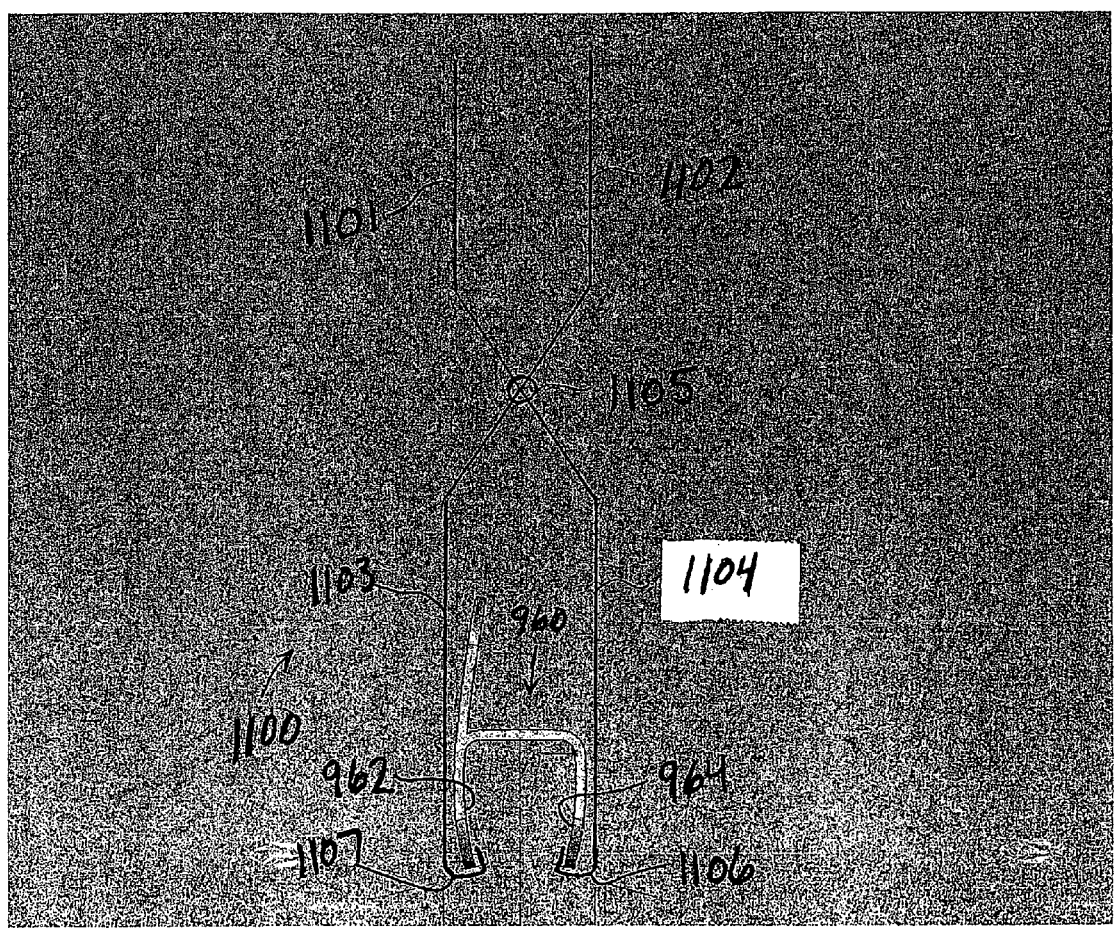

FIG. 34 is an end view of a tool used to spread open a clamp according to an exemplary embodiment of the present disclosure.

Figure 35:
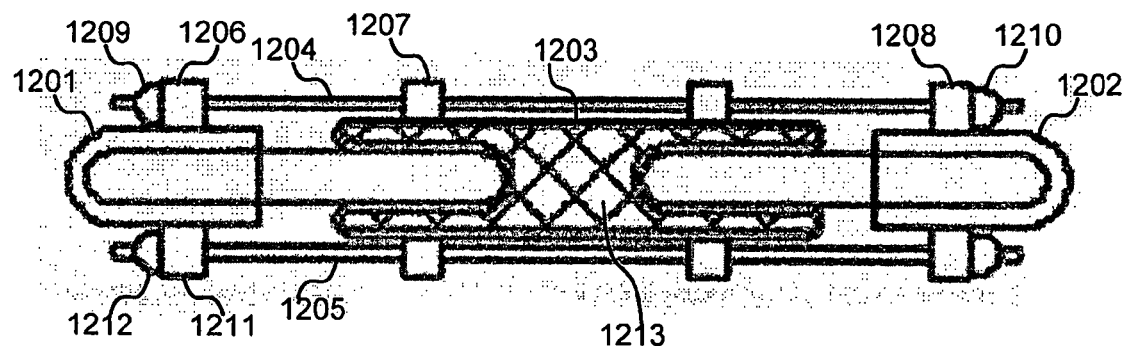

FIG. 35 is a posterior view of one embodiment of a system for fixation of spinous processes.

Figure 36:
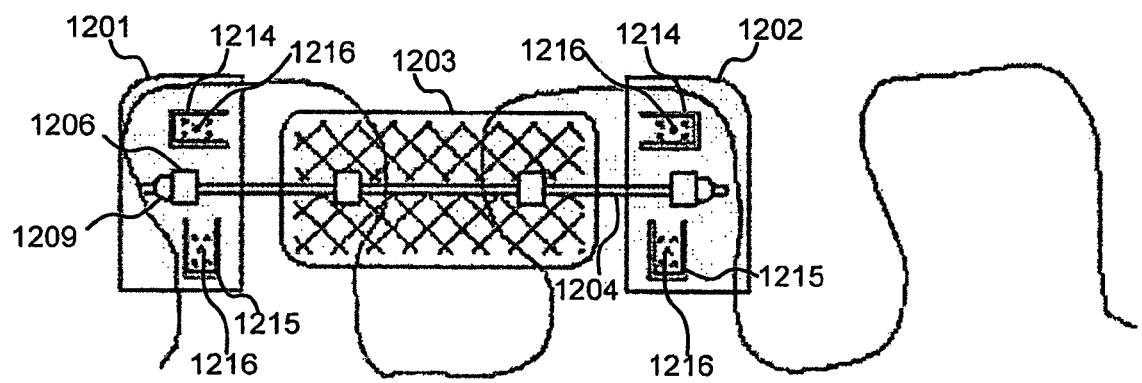

FIG. 36 is a side view of one embodiment of a system for fixation of spinous processes.

Figure 37:
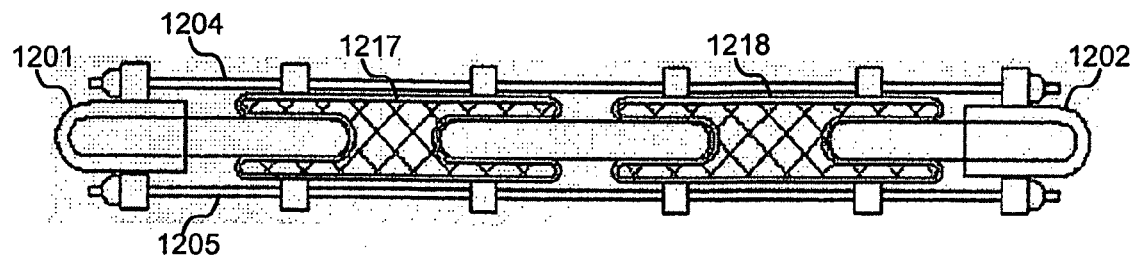

FIG. 37 is a posterior view of an expanded system for fixation of spinous processes.

Figure 38:
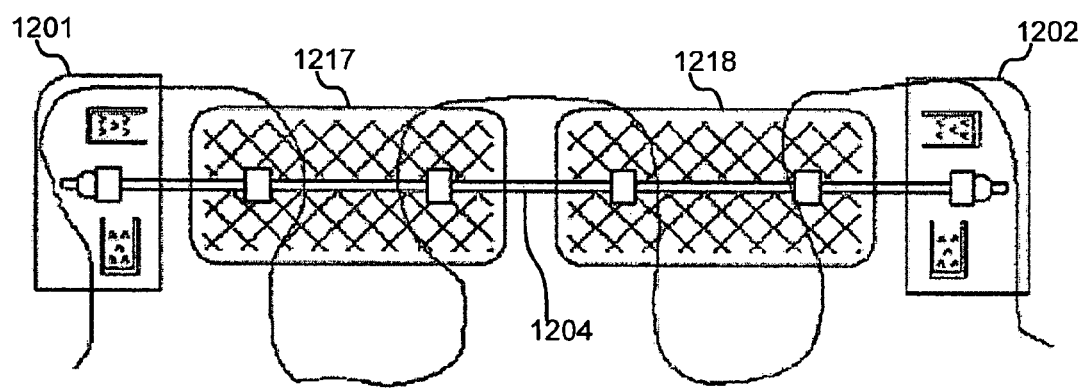

FIG. 38 is a side view of an expanded system for fixation of spinous processes.

Figure 39:
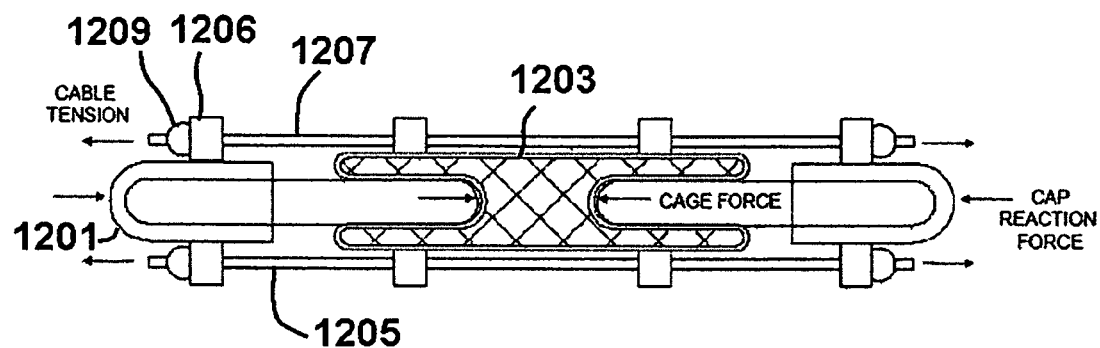

FIG. 39 is a posterior view of a force diagram illustrating force balancing in a system for fixation of spinous processes.

Figure 40:
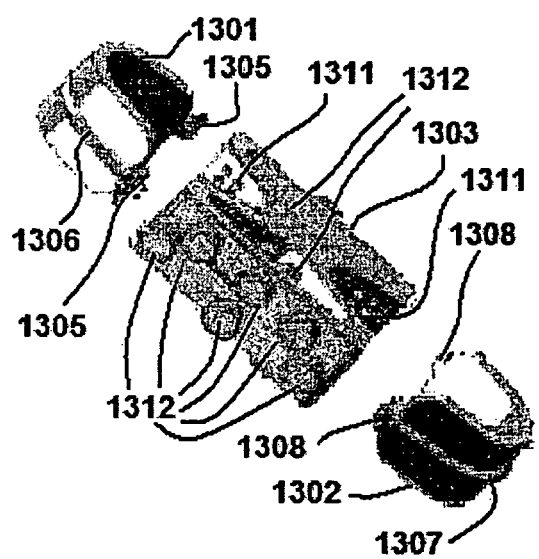

FIG. 40 is a perspective view of one embodiment of a system for fixation of spinous processes.

Figure 41:
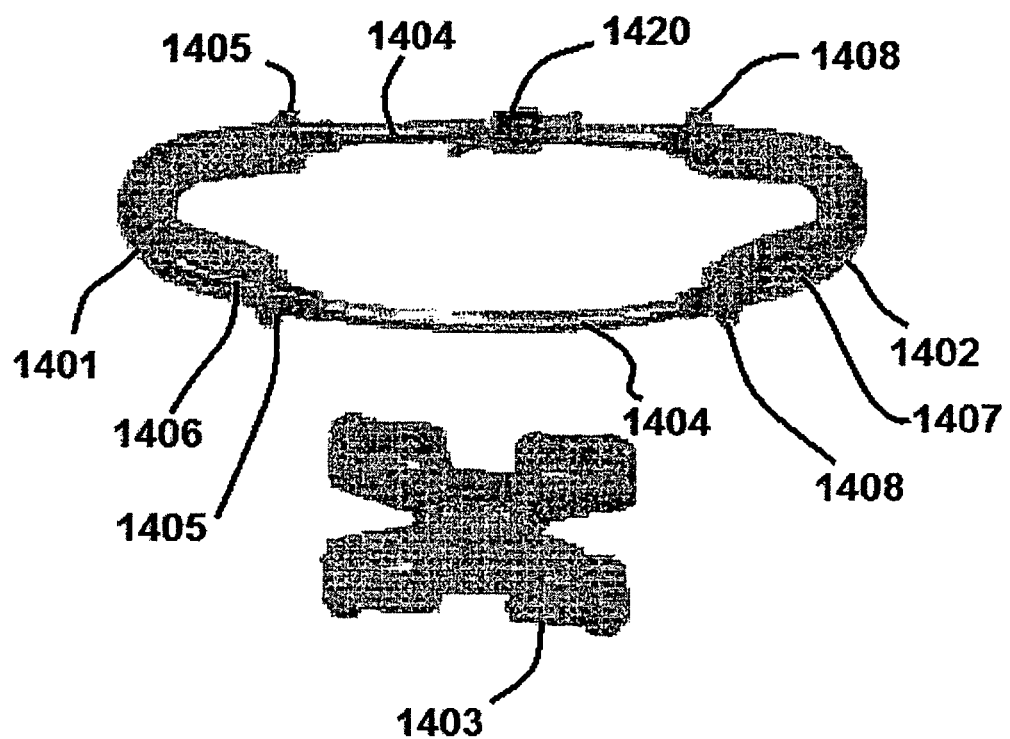

FIG. 41 is a perspective view of one embodiment of a system for fixation of spinous processes.

Figure 42:
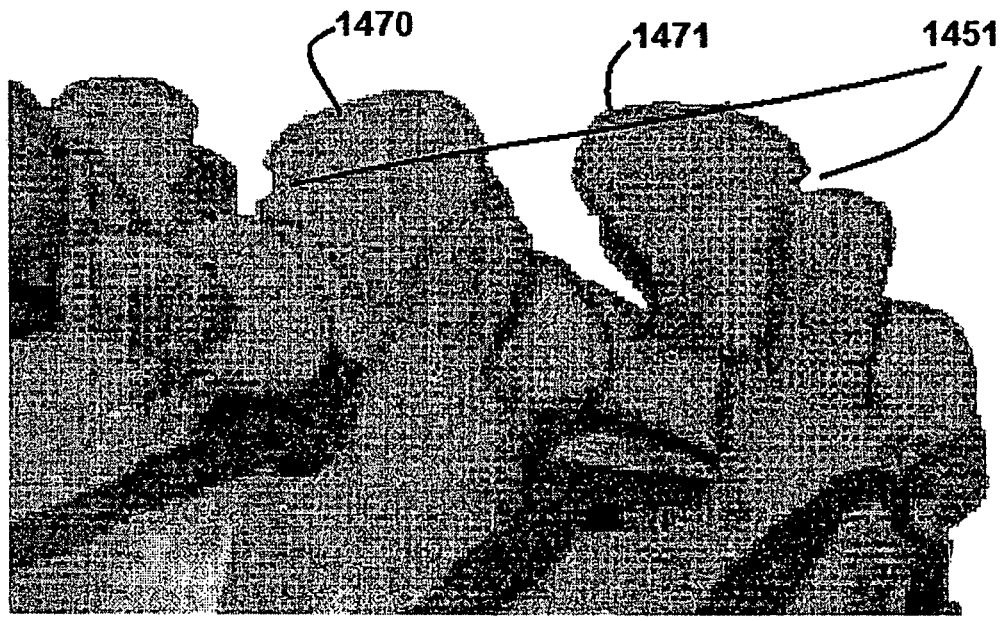

FIG. 42 is a perspective view of a pair of adjacent spinous processes prepared for installation of the system of FIG. 41.

Figure 43:
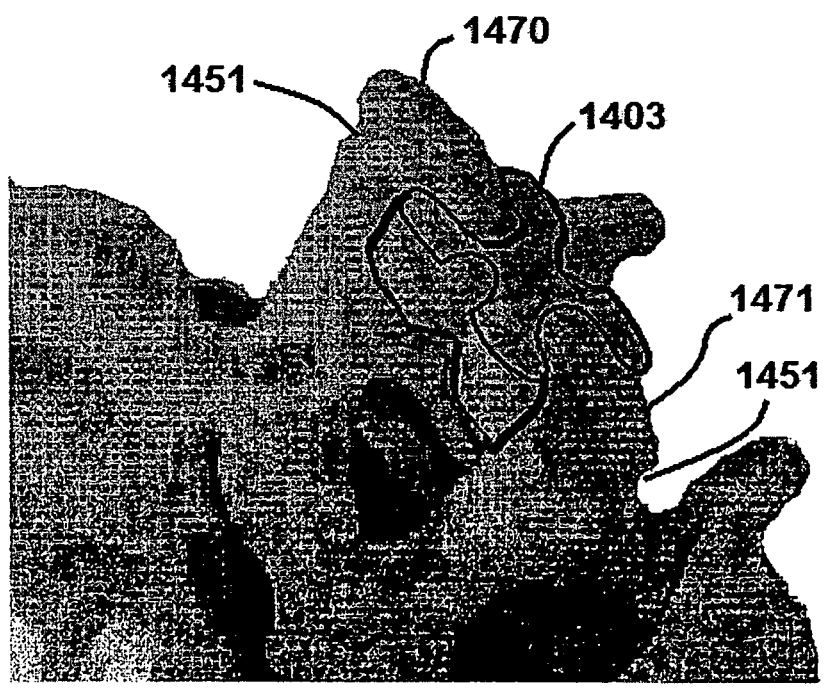

FIG. 43 is a perspective view of a component of the system of FIG. 41 installed between two spinous processes.

Figure 44:
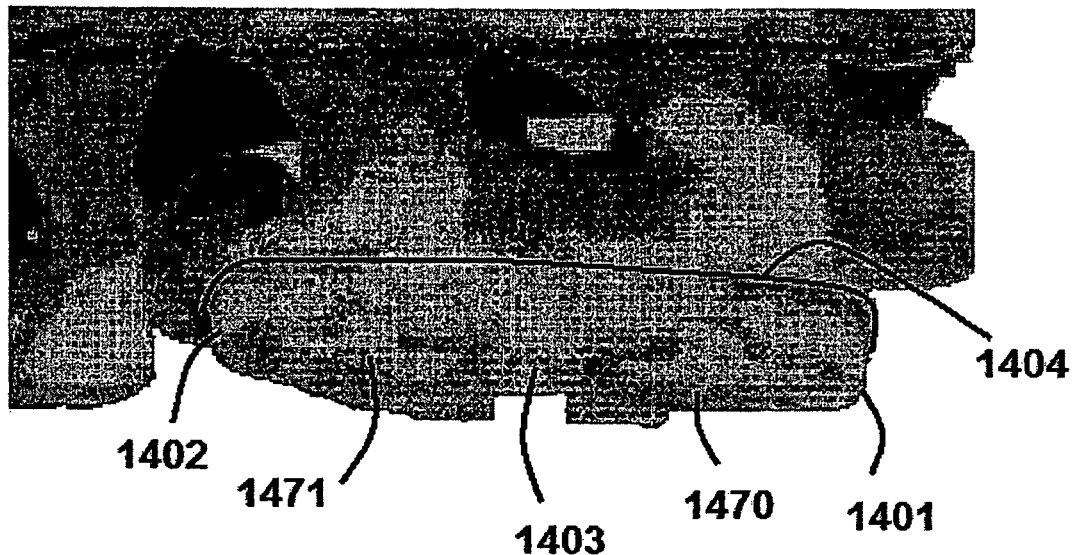

FIG. 44 is a perspective view of the system of FIG. 41 installed between two spinous processes.

Figure 45:
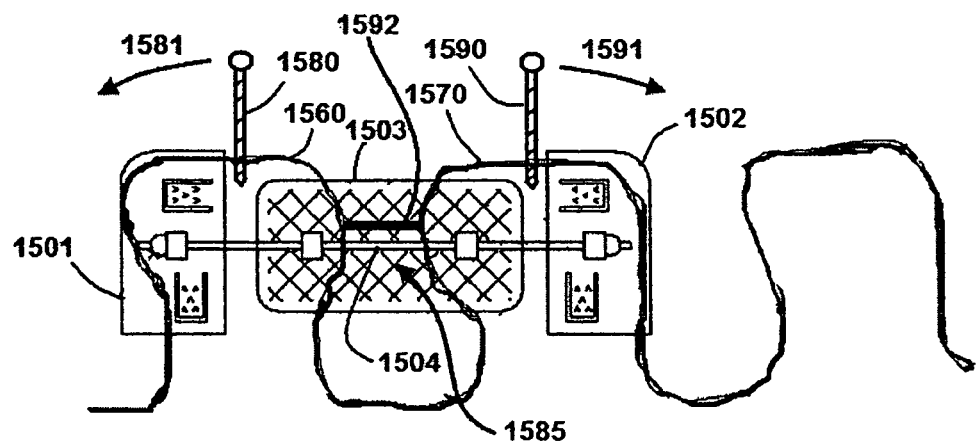

FIG. 45 is a side view of one embodiment of a system for distraction and fixation of spinous processes.

Figure 46:
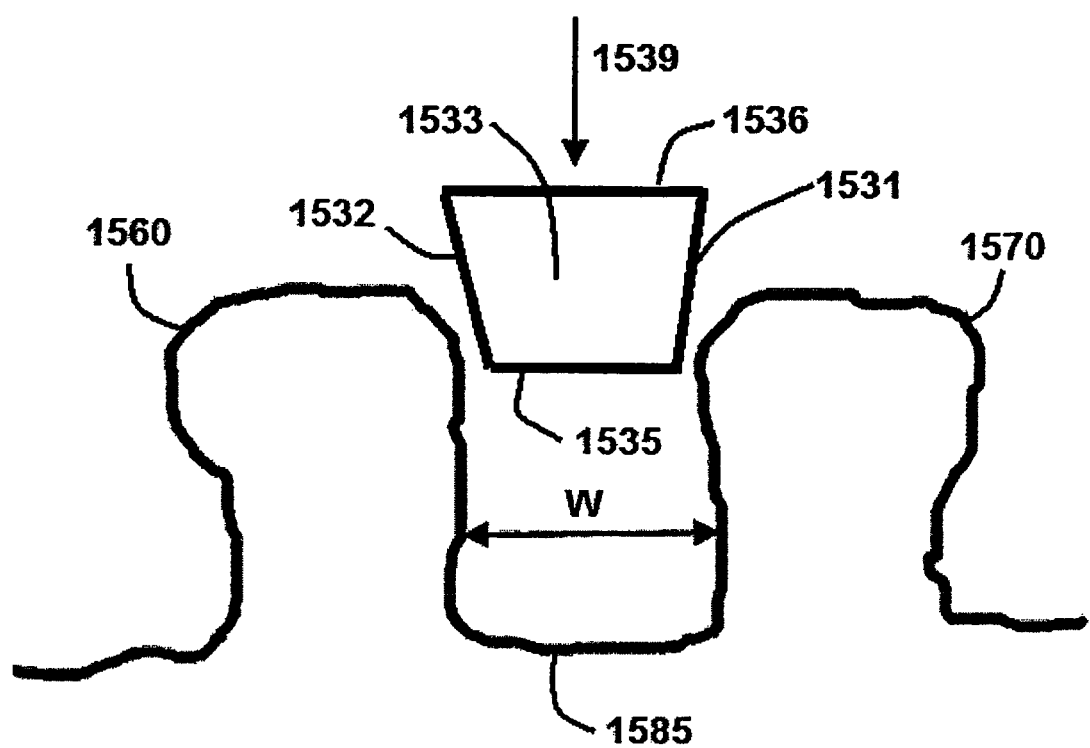

FIG. 46 is a side view of one embodiment of a system for distraction of spinous processes.

Figure 47:
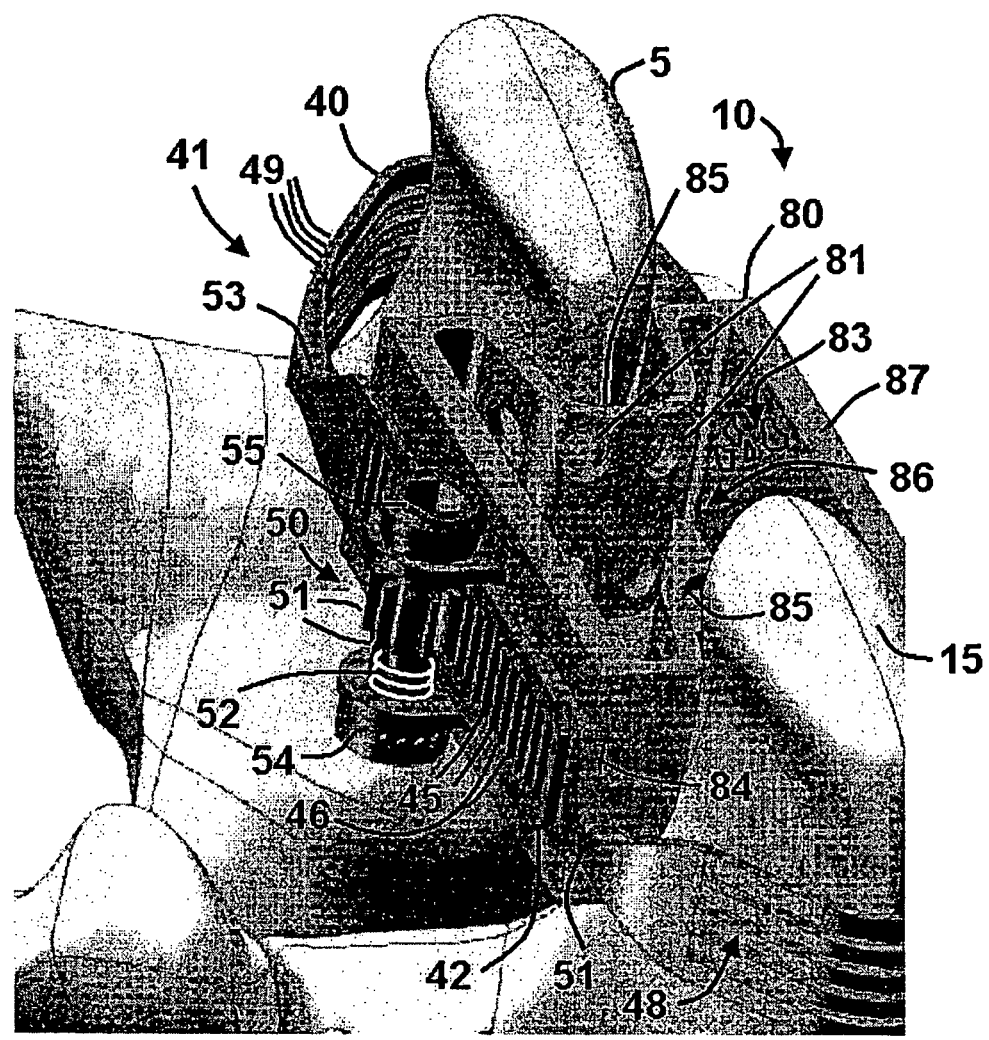

FIG. 47 is a perspective view of one embodiment of a system for fixation of spinous processes.

Figure 48:
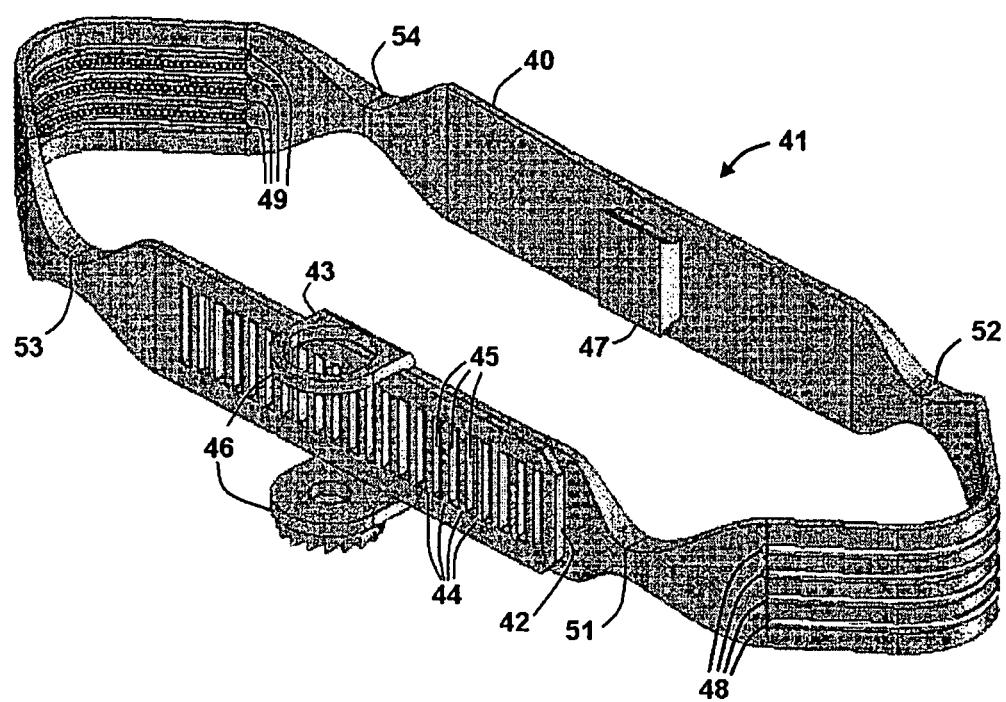

FIG. 48 is a perspective view of one component of the embodiment of FIG. 47.

Figure 49:
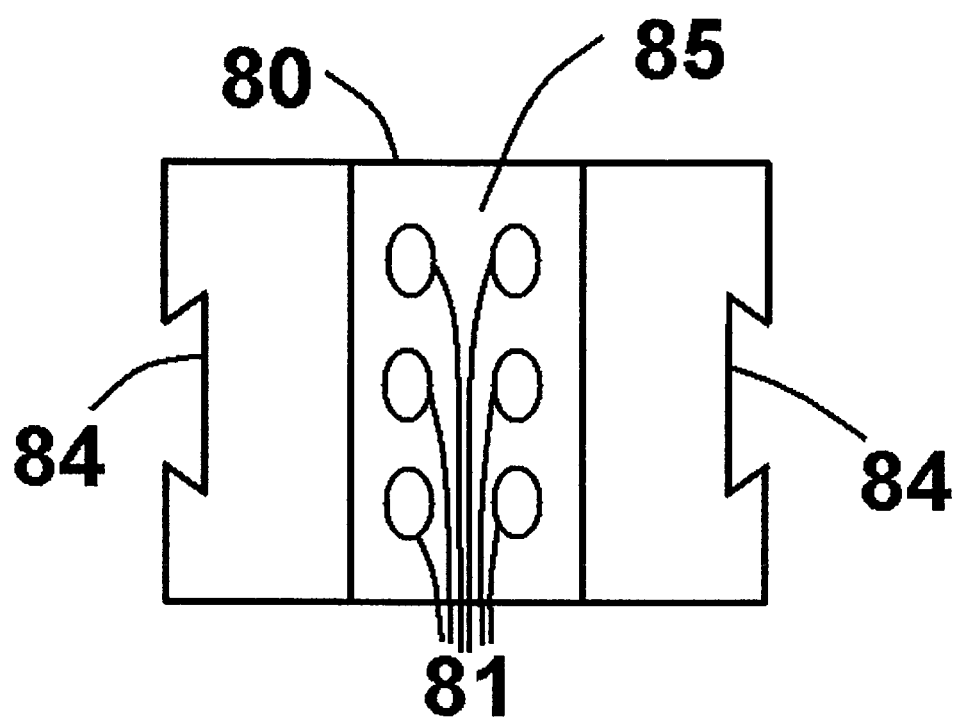

FIG. 49 is an end view of one component of the embodiment of FIG. 47.

Figure 50:
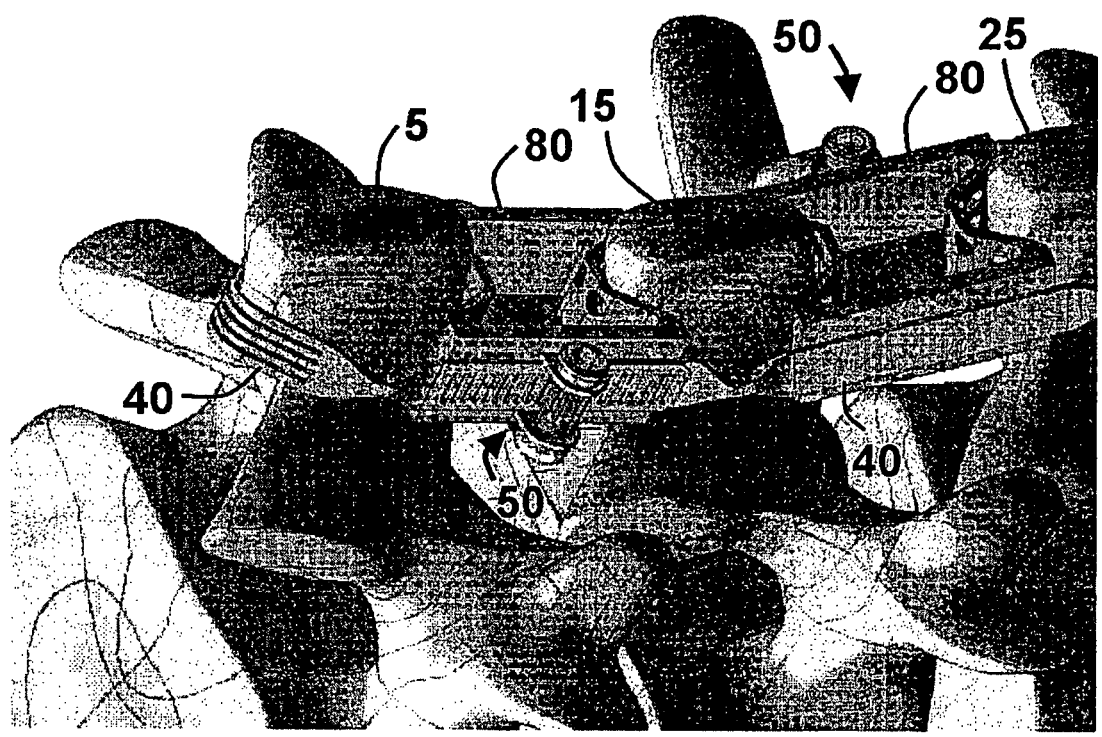

FIG. 50 is a perspective view of one embodiment of a system for fixation of spinous processes.

Figure 51:
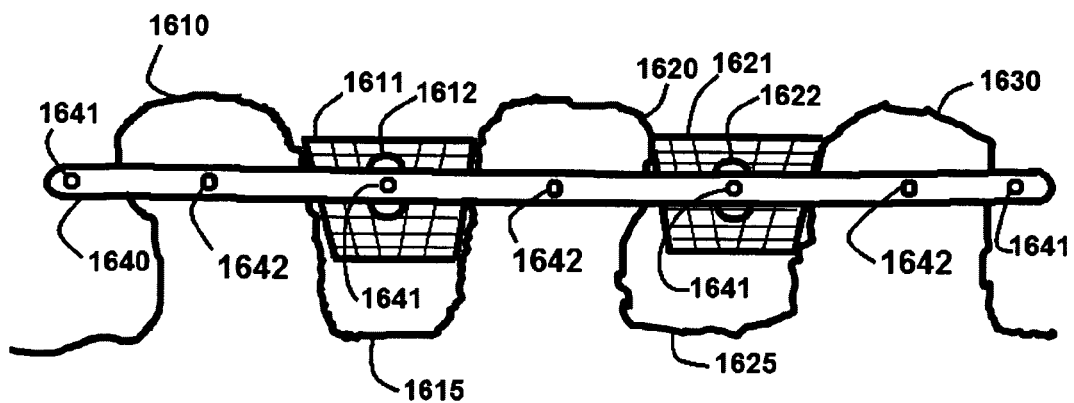

FIG. 51 is a side view of a system for fixation of spinous processes.

Figure 52:
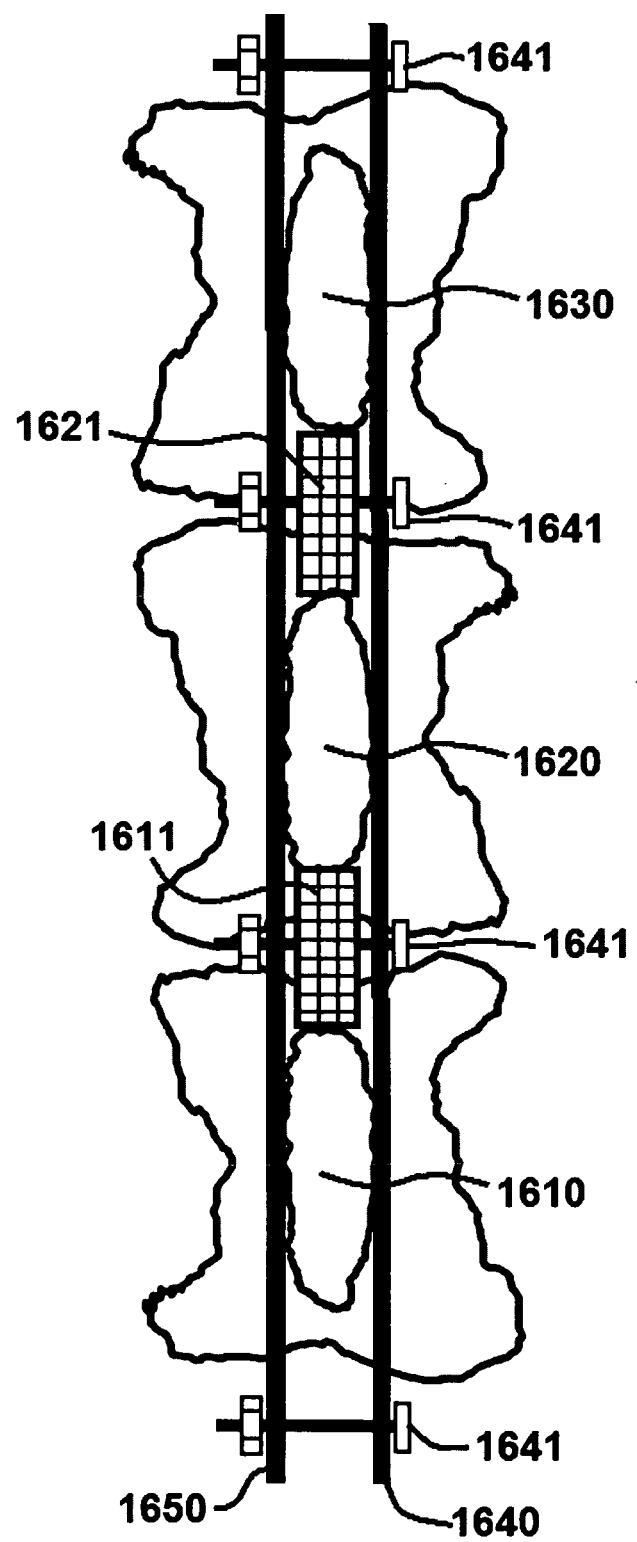

FIG. 52 is a top view of the embodiment of FIG. 51.

Figure 53:
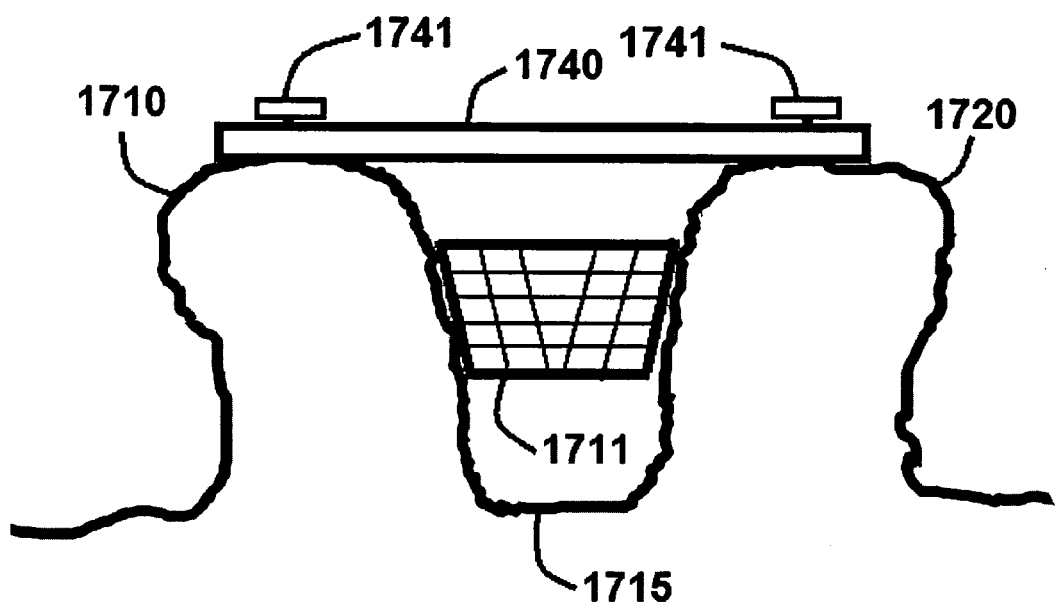

FIG. 53 is a side view of a system for fixation of spinous processes

Figure 54:
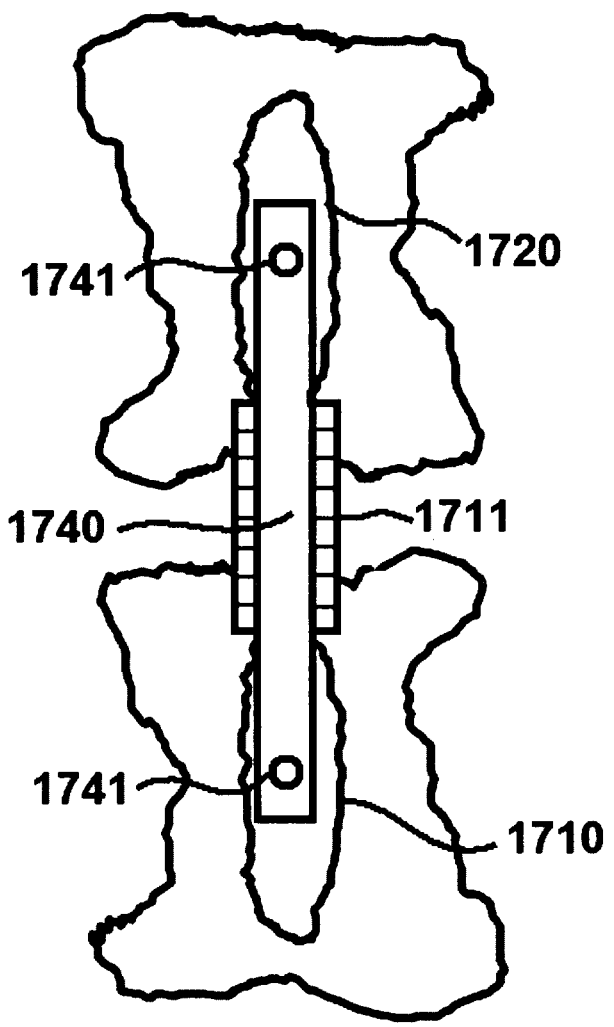

FIG. 54 is a top view of the embodiment of FIG. 53.

Figure 55:
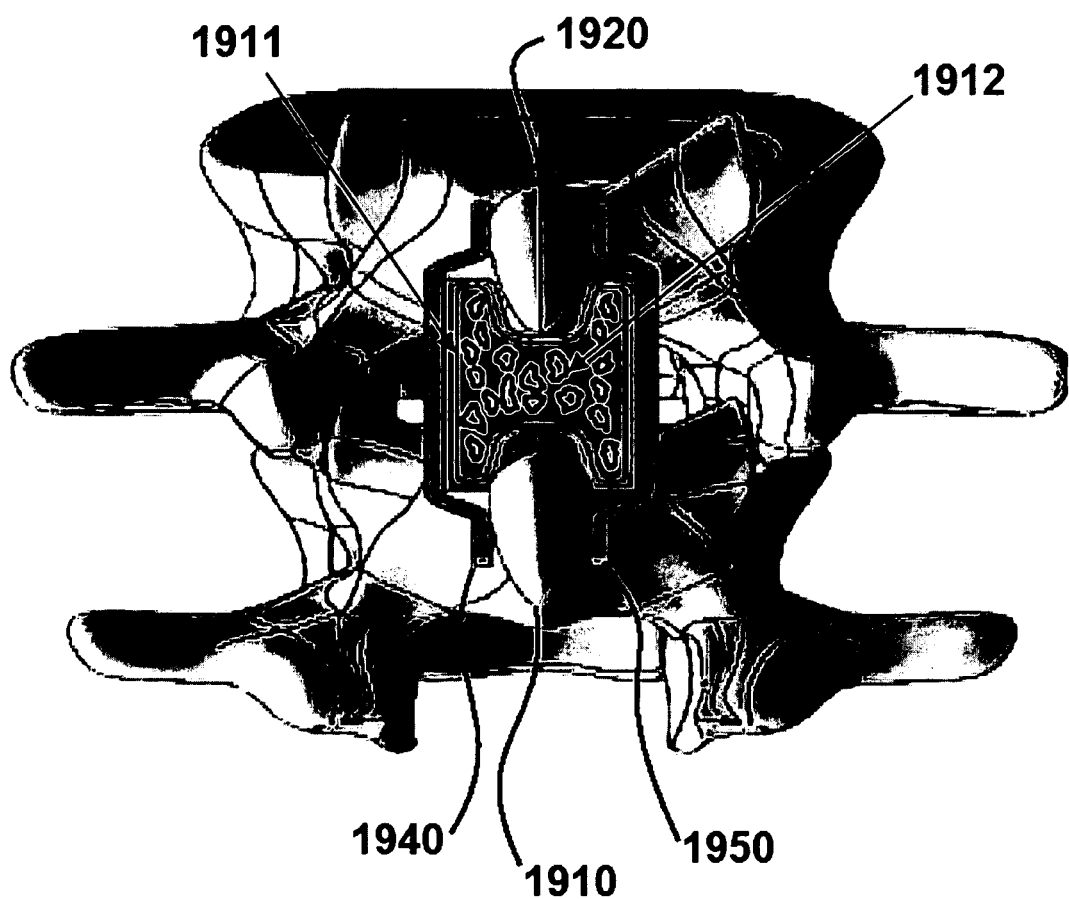

FIG. 55 is a top view of a system for fixation of spinous processes.

Figure 56:
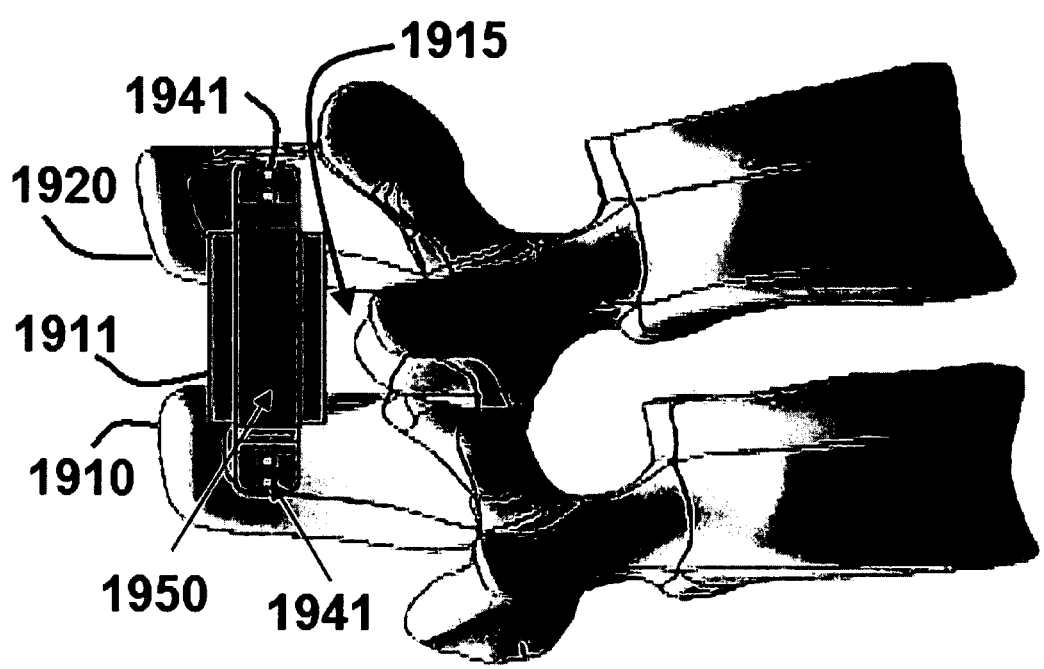

FIG. 56 is a side view of the embodiment of FIG. 55.

Figure 57:
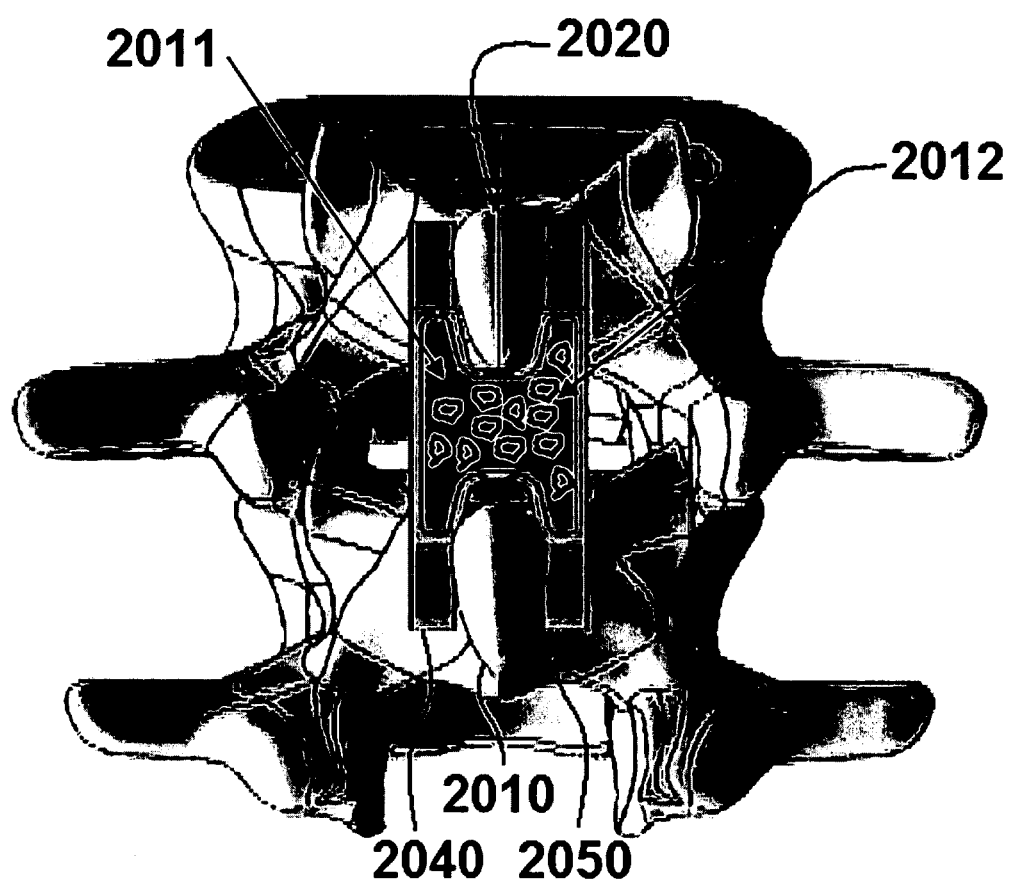

FIG. 57 is a top view of a system for fixation of spinous processes.

Figure 58:
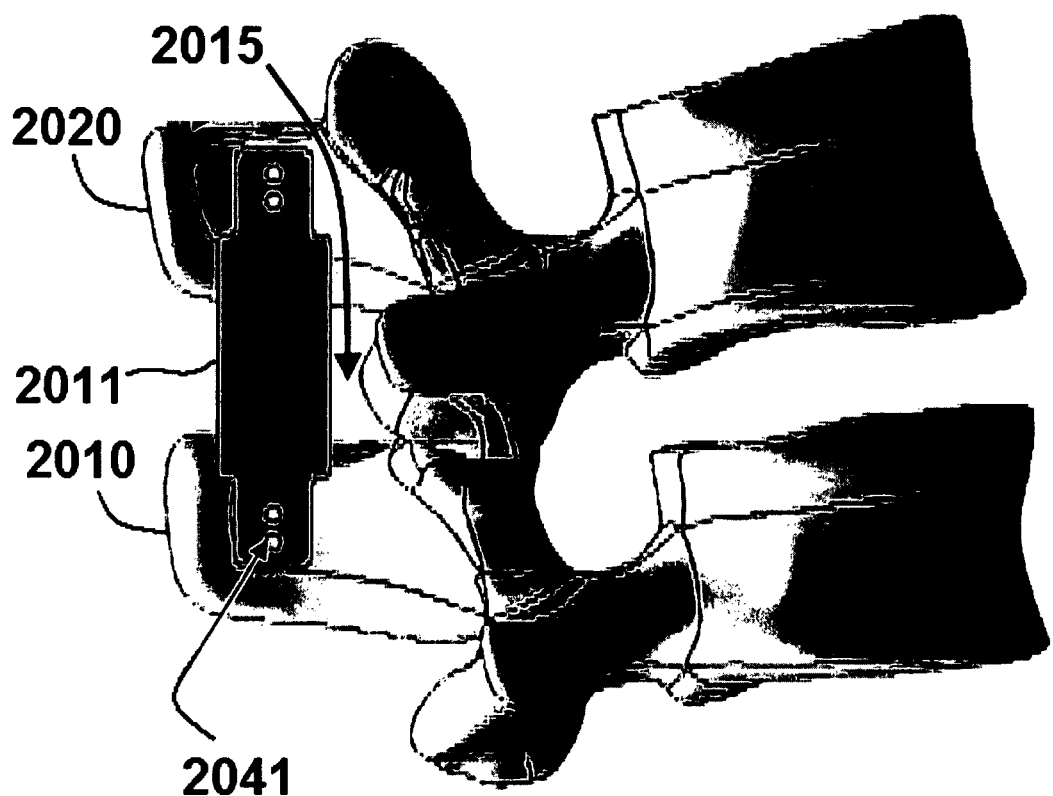

FIG. 58 is a side view of the embodiment of FIG. 57.

DETAILED DESCRIPTION OF EXEMPLARY EMBODIMENTS

FIGS. 1A, 1B and 2, illustrate end views and a side view of exemplary embodiments of a clamp 100. Clamp 100 comprises a first side 105, a second side 110, and a coupling portion 115 that couples first side 105 to second side 110. First side 105 and second side 110 comprise end portions 160 and 165, respectively, that are distal from coupling portion 110. Clamp 100 further comprises an open space 120 between first side 105 and second side 110. In the exemplary embodiment shown, first side 105 and second side 110 comprise gripping members 125 and receiving members 130. As shown in FIG. 2, clamp 100 also comprises a first end 145 and a second end 150.

In certain embodiments, gripping members 125 may be small projections, prongs, tines, tabs, barbs or spikes directed toward open space 120. Gripping members 125 may also be used in combination with cement, epoxy, banding, or small screws in exemplary embodiments. In certain embodiments, gripping members 125 may be formed by deforming a portion of first side 105 or second side 110 (for example, by using a punch to press a portion of the material towards open space 120).

In the embodiments shown in FIG. 1B, clamp 100 is configured so that end portions 160 and 165 are closer together than the remaining portions of first side 105 and second side 110 (i.e., the side portions that are closer to connecting portion 115). As described further below, such a configuration can allow clamp 100 to exert a compressive force on an object placed within open space 120. In certain embodiments, a tool (not shown) can be used to force end portions 160 and 165 farther apart so that they can be placed over an object to which clamp 100 will be clamped. Connecting portion 115 can then bias end portions 160 and 165 towards each other and provide a compression force on the object placed in open space 120. In certain embodiments, an installation tool can be used to grip a pair of tool engagement members or tabs 132 to assist in the installation of clamp 100. For example, a plier-type device can be used to grip and squeeze tabs 132 towards each other. This action will cause end portions 160 and 165 to move away from each other and allow clamp 100 to be placed over an object to be clamped. In certain embodiments, tabs 132 can also be used to assist in removal of clamp 100. In other embodiments, clamp 100 can be installed and permanently left in place. Although it is understood that the figures are not drawn to scale, FIG. 1C illustrates another embodiment similar to FIG. 1A. In this embodiment, however, gripping members 125 are shorter than those illustrated in FIG. 1A.

Referring now to FIG. 3, clamp 100 is shown installed on a spinous process 135 of a vertebra 140. As shown in this exemplary embodiment, gripping members 125 can penetrate into the periosteum of spinous process 135 to assist in securing clamp 100 to vertebra 140. In certain exemplary embodiments, gripping members 125 are distributed across first side 105 and second side (from top to bottom and end to end) to provide a broad attachment area. By utilizing a relatively large interface area between clamp 100 and spinous process 135, the resistance to shear forces is increased. Therefore, clamp 100 may be securely fastened to spinous process 135 of vertebra 140 without the use of screws. In the exemplary embodiment shown, clamp 100 encases the sides as well as the cephalad/caudad portions of spinous process 135.

Referring now to FIG. 4A, a system 101 of multiple clamps 100 is shown coupled to a series of vertebrae 140. In this embodiment, clamps 100 are shown coupled to the spinous process 135 of each vertebra 140. As illustrated, coupling members 155 extend between receiving members of each clamp 100. In this exemplary embodiment, each clamp 100 comprises a different type of receiving member. The rightmost clamp 100 comprises receiving members 131 that comprise threaded portions and receive threaded portions 156 of coupling members 155. The middle clamp 100 comprises receiving members 133 that serve as guides and allow coupling members 155 to slide laterally relative to them. The leftmost clamp 100 comprises receiving members 133 that allows coupling members 155 to rotate within coupling members 133, but restricts coupling members 155 from sliding laterally relative to them. In certain embodiments, a spacer 153 can be placed between vertebrae 140 to assist in placing the vertebrae 140 under distraction. After clamps 100 and coupling members 155 have been installed, spacer 153 can be removed.

In certain embodiments, system 101 can be used to provide segmental fixation of vertebrae 140 and provide either distraction or compression of the vertebrae. In certain exemplary embodiments, system 101 can be used to provide fixative support, while in other embodiments, system 101 can be used to provide dynamic support. In the embodiment shown, after clamps 100 have been attached to the spinous processes 135 of vertebrae 140, coupling members 155 can be rotated so that the threaded portions 156 are threaded into or out of receiving members 131. Threaded portions 156 may be threaded into receiving members 131 (so that the right clamp and left clamp are pulled towards each other) to cause a compressive force to be placed on vertebrae 140. Threaded portions 156 may also be rotated to that coupling members 155 are threaded out of receiving members 131. Such manipulation would cause the right and left clamp to be pushed away from each other and place vertebrae 140 under distraction or tension.

It is understood that only one exemplary embodiment is shown in FIG. 4A. Other exemplary embodiments (not shown) may comprise coupling members and receiving members with different configurations that allow compression or distraction forces to be placed on vertebrae 140. For example, system 101 may comprise coupling members that comprise turn-buckles to decrease or increase the length of the coupling members and place compression or distraction forces on the vertebrae. In other exemplary embodiments, coupling members may comprise other configurations. For example, a coupling member may comprise a spring or other biasing member to exert a force on a clamp 100. Still other embodiments may comprise a coupling member that includes a dampener. The ends of coupling members may utilize any number of configurations to secure the coupling member to a clamp receiving member. For example, coupling members and receiving members may comprise a ball-and-socket or spherical arrangement, a recess with a spring-clip retainer, a tongue-and-groove arrangement, or any other suitable mechanism that can be used to secure a coupling member to a clamp. Other examples of securement mechanisms include a tab system suitable for crimping the coupling member to the clamp, a hole (in either the coupling member or the clamp) and a screw, or a nut and a threaded rod end.

Certain exemplary embodiments may comprise a kit comprising multiple configurations of clamps and coupling members. For example, a kit may comprise several clamps 100, as well as coupling members 155 that comprise different configurations to allow compression or distraction forces to be placed on vertebrae. In such embodiments, only a portion of the items in the kit may be needed and utilized for a particular procedure. Those components that are not needed may be disposed of after the procedure is completed.

Referring now to FIG. 4B, a second exemplary embodiment is similar to the embodiment shown in FIG. 4A, but comprises a single clamp 300 that spans two vertebrae 340. As shown, clamp 300 comprises an first end portion 305 that clamps to the spinous process of a vertebra 340 and a second end portion 310 that couples to a spinous process 335 of an adjacent vertebra 340. A central portion 315 of clamp 300 couples end portions 305 and 310. Gripping members 325 (similar to those previously described) are used to secure clamp 310 to spinous processes 335. A spacer (not shown) may be used to provide distraction forces to vertebrae 340 before clamp 300 is installed.

Exemplary embodiments also comprise other methods of using disclosed systems as an intraspine stabilization device. Clamps according to the present disclosure may be coupled to cervical vertebrae (particularly C5-C7), as well as thoracic vertebrae (i.e., T1-T12), lumbar vertebrae (L1-L5), and sacral vertebrae (S1-S5). In one particular embodiment, a surgeon may expose the spinous process and lamina of a patient. Then, any desired decompression can be formed via techniques known in the art (with care taken to preserve the spinous process). Clamps can be placed and secured on the spinous processes above and below the diseased level. A separate device can then be used to achieve the desired level of distraction or compression. Once the desired amount of distraction or compression is achieved, the clamps may be linked together rigidly with coupling members. At that point, posterior fusion may be performed if desired and the surgical opening closed. In one particular exemplary embodiment, the system can be used to provide treatment for scoliosis to assist in straightening a patient's spine.

In other exemplary embodiments, clamps may be secured to locations other than the spine. For example, a clamp according to exemplary embodiments may be used as a calvarial clamp in intracranial surgery to aid in securing bone. Referring now to FIGS. 5 and 6, a clamp 200 is shown affixed to a calvarial flap 235 in a patient's cranium 240. FIG. 5 represents a top view looking down at cranium 240, while FIG. 6 illustrates a section view taken along line 6-6 in FIG. 5. As shown in FIGS. 5 and 6, clamp 200 comprises gripping members 225 that grip calvarial flap 235. Clamp 200 also comprises an extension 230 that extends over the portion of cranium 240 that is proximal to calvarial clamp 235. Extension 230 can be secured to cranium 240 via screws 231 (shown) or other securement device. For example, other embodiments may comprise a clamp that clamps to the cranium and uses a pin or other mechanism (such as a quarter-turn quick connect device) to couple the flap clamp and the cranial clamp together. Clamp 200 can therefore reduce the need to secure a calvarial flap to the cranium with plates and screws in the calvarial flap. The use of clamp 200 may therefore allow a calvarial flap to be more easily removed should the need arise. In specific embodiments, clamp 200 may be comprised of a material that is rigid and deformable, such as a metallic alloy.

Clamps such as clamp 100 may also be used to set small bone fractures, such as or for the repair of sternotomy incisions. Clamp 100 may also be used to secure soft tissue (such as a tendon) to bone. For example, as shown in FIG. 7, clamp 100 can be configured to include an eyelet 139 that can be used to secure a tendon 138. Clamp 100 can also be particularly suited for setting facial fractures or other areas where screws are not desired, such as applications in close proximity to high concentrations of nerve tissue.

Referring now to FIGS. 8 and 9, an exemplary embodiment of a clamp 400 is shown. Clamp 400 is similar to previously-described clamps, but includes a set of gripping members 425 in the form of crimp tabs. In the view shown in FIG. 8, one side of clamp 400 comprises a gripping member 425 at each end of clamp 400 and near the top of clamp 400. The opposite side (not shown) is equivalent to the side illustrated. In the end view shown in FIG. 9, clamp 400 is shown installed on a spinous process 435 of a vertebra 440. As shown in this view, gripping members 425 located near the top of clamp 400 have been deformed or crimped so that they engage the top of spinous process 435. In addition, gripping members 425 near the ends of clamp 400 have been crimped to wrap around the ends of spinous process 435. In exemplary embodiments, gripping members 425 are plastically deformed to engage spinous process 435. In certain exemplary embodiments, a band 426 can be installed around clamp 400 and spinous process 435 to assist in securing clamp 400 in place.

Referring now to FIG. 10, a system 401 of clamps 400 have been installed on spinous processes 435-438 of vertebrae 440-443. As shown in FIG. 10, gripping members 425 have been crimped around spinous processes 435-438. In this exemplary embodiment, a coupling member 455 is placed between clamps 400 on spinous processes 435 and 436 of vertebrae 440 and 441, a coupling member 456 is placed between clamps 400 on spinous processes 436 and 437 of vertebrae 441 and 442, and a coupling member 457 is placed between clamps 400 on spinous processes 437 and 438 of vertebrae 442 and 443. In this particular configuration, coupling member 457 is a semi-rigid member that essentially fuses the spinous processes 436 and 437 of vertebrae 441 and 442 together. Coupling member 457, however, comprises a flexible member 458 that allows for movement between spinous processes 437 and 438 of vertebrae 442 and 443. In addition, coupling member 455 comprises a dampener 459 that allows for dampened movement between spinous processes 435 and 436 of vertebrae 440 and 441. Such a configuration relieves the stresses in the spinous processes and vertebrae above and below the fused spinous processes 435 and 436 of vertebrae 440 and 441.

In still other exemplary embodiments, a clamp may be secured to another securement device rather than an additional clamp. One example of another securement device is a screw that is implanted into a vertebra. Other examples include a wire, a plate, or a band. One specific example of a screw is a pedicle screw, but a clamp may be secured to any suitable screw in any suitable area. A clamp may be secured to an existing screw or one that is installed in the same procedure as the clamp. Such configurations may be desirable, for example, when a spinous process has been damaged or removed from a particular vertebra of a patient. Referring to the embodiment shown in FIG. 11, clamp 400 is shown coupled to spinous process 435 of vertebra 440. Vertebra 444, located adjacent to vertebra 440, has had its spinous process removed. As shown in this embodiment, a pedicle screw 461 has been inserted into vertebra 444. In this embodiment, a coupling member 460 couples clamp 400 to pedicle screw 461.

Another exemplary embodiment is shown in FIG. 12. In this embodiment, a series of clamps 800 are coupled to spinous processes 840-842 via gripping members 425. A sacral clamp 810 is also shown that is specifically configured to clamp to a sacral vertebra (i.e. S1-S5). Clamps 800 are coupled to each other via coupling members 800. Clamps 800 are also coupled to approximately half of a spinous process, rather than the majority (or entire) spinous process. Such a configuration may reduce the number of different sizes of clamps that may be needed to accommodate different sizes of spinous processes. This configuration may be particularly suited to applications where coupling member 800 is exposed to compression forces, which allows the opposing faces of adjacent spinous processes to bear some of the load. In the exemplary embodiment shown in FIG. 12, there is a gap 805 between clamps 800 affixed to a spinous process. In the exemplary embodiment shown in FIG. 13, clamps 800 overlap approximately one-quarter of their width when installed on a single spinous process.

Embodiments may comprise coupling members and receiving members of many different configurations. Referring now to FIGS. 14 and 15, a coupling member 500 may comprise an elongated central portion 505 and a pair of ends 510, 515 that comprise attachment holes 520, 525 that can be connected to a pair of receiving members (not shown).

Another exemplary embodiment of a coupling member is shown in FIG. 16. In this embodiment, coupling member 550 comprises a central portion 565, a recess 555 at one end, and a recess 560 at the opposite end. Recesses 555 and 560 are configured so that a vertebra may be engaged within each recess. Central portion 565 may then serve as a spacer between the vertebrae engaged in the recesses 555 and 560. Central portion 565 comprises a distance S between recess 555 and recess 560. In certain embodiments distance S may be 8, 9, 10, 11, 12, 13, 14, 15, or 16 millimeters. In other embodiments, distance S may be different distances. Recesses 555 and 560 are also a certain width W. In certain embodiments, width W may be 8, 9, 10, 11, 12, 13, 14, 15, 16, 17, 18, 19 or 20 millimeters. In other embodiments, distance W may be different distances.

In still another exemplary embodiment shown in FIG. 17, a clamp 600 may be used as a sacral iliac crest bridge after a bone graft has been removed. In this embodiment, clamp 600 comprises a first gripping member 605 and a second gripping member 610. In the embodiment shown, gripping members 605 and 610 are shown as crimped portions. Clamp 600 covers the graft portion 615 of a sacral iliac crest 620. In certain embodiments, the graft portion 615 can be filled bone growth media 625 to promote bone growth in the area where the graft was removed.

In still other embodiments, a clamp may be used across a joint that needs to be fused, for example a metatarsophalangeal articulation. In other embodiments, a clamp may be placed across a long bone that needs to be stabilized, such as a humeral fracture. In still other embodiments, a clamp may be placed across a small bone in the hand or foot.

Referring now to FIGS. 18-23B, an exemplary embodiment of a spinous process clamp system 1800 comprises one or more clamps 1801 and coupling members 1850. In the embodiment shown, clamp 1801 is comprised of a unitary piece of material, while in other embodiments clamp 1801 may be comprised of multiple pieces coupled together. In specific embodiments, clamp 1801 may be formed from a single flat sheet of material that is formed into the configuration shown in FIGS. 18-23. For example, various dies or punches may be used to remove material and create features such as apertures and gripping members (described in more detail below). The sheet may then be bent to form the configuration shown, or other configurations.

In the embodiment shown, clamp 1801 comprises a central portion 1805 with a pair of side portions 1810, which are formed into a U-shape when viewed from above clamp 1801. The open ends of the U-shape of side portion 1810 may be closer together than the base of the U-shape. Such a configuration allows side portion 1810 to place a compressive force on a coupling member 1850 or other member inserted into side portion 1810. In addition, side portions 1810 may comprise inner and outer apertures 1820 and 1825. In the embodiment shown, inner and outer apertures 1820, 1825 are multifaceted, specifically ten-sided. In other embodiments, the apertures may be different configurations. For example, the number of sides for the apertures may range from six sides to twenty sides, inclusive.

Side portions 1810 also comprise a pair of gripping members 1815 proximal to the space between side portions 1810. In the embodiment shown, gripping members 1815 comprise a series of teeth directed towards the space between side portions 1810. In other embodiments, gripping members may comprise a different configuration. In certain embodiments, side portions 1810 may also comprise flanged portions 1830 proximal to the one end of the U-shaped channel formed by each side portion 1810.

In the embodiment shown, central portion 1805 comprises a top portion 1806 that is bent to fill in the space between side portions 1810. As shown in FIGS. 18 and 19, when clamp 1801 is installed on a spinous process 1870, top portion 1806 covers a portion of the top of one end of spinous process 1870. A pair of clamps 1801 can be installed on a single spinous process 1871 and the configuration of clamp 1801 allows it to be placed on either end of the spinous process. Furthermore, the configuration allows a pair of clamps 1801 to be placed on a spinous process regardless of the length L of the spinous process. In the embodiment shown, the clamps 1801 installed on the same spinous process (such as spinous process 1871) are not coupled to each other. Therefore, the distance from one end of a spinous process to the opposite end of the spinous process does not affect the ability of clamps 1801 to fit onto the spinous process.

Also shown in FIGS. 18 and 19, gripping members 1815 may be used to grip spinous processes 1870 and 1871 in order to secure clamp 1801 to the spinous process. In addition, the inner walls 1812 of side portions may be angled towards each other so that they must be slightly spread apart in order to fit over spinous process 1870 or 1871. Such a configuration may place a compressive force on spinous process 1870 or 1871 and further assist in retaining clamp 1801 onto spinous process 1870 or 1871.

As shown in FIGS. 18 and 19, a pair of clamps 1801 may be coupled to adjacent spinous processes. The clamps 1801 may then be coupled to each other by coupling members 1850, which comprise an elongate body 1855 comprising a pair of extensions 1860 proximal to each end. In certain embodiments, extensions 1860 may surround apertures 1861. In exemplary embodiments, extensions 1860 are configured to engage inner and outer apertures 1820 and 1825 (for example, extensions 1860 may comprise the same number of facets as apertures 1820 and 1825). As shown in FIGS. 18 and 19, even if adjacent clamps 1801 are not at equivalent elevations, coupling members 1850 can be positioned within inner and outer apertures 1820 and 1825 so that the coupling members couple the adjacent clamps 1801. As the number of sides or facets is increased for apertures 1820, 1825 and extensions 1860, the number of positions in which coupling member 1850 can be arranged is also increased. However, increasing the number of sides or facets also reduces the ability of coupling member 1850 to be positively engaged with clamp 1801.

In specific embodiments, a coupling member 1850 is inserted into the open end of each U-shaped side portion 1810. Similar to previously-described embodiments, side portion 1810 may be configured so that it must be expanded slightly in order to insert coupling member 1850. Therefore, side portion 1810 will create a compressive force on coupling member 1850 after it is inserted. This compressive force, along with the faceted engagement of extensions 1860 and apertures 1820 and 1825, can serve to provide a secure coupling between coupling members 1850 and clamp 1801. In certain exemplary embodiments, extensions 1860 may be elastically deformed after insertion into apertures 1820 and 1825. In specific embodiments, extensions 1860 may be mechanically upset or swaged after insertion. This can also assist in maintaining the integrity of the coupling between coupling member 1850 and clamp 1801.

Referring now to FIGS. 24-25, a clamp 940 may be used to secure a bone 951 in a foot 950. Clamp 940 comprises a coupling portion or central member 942, first extensions 944 and second extensions 946. First extensions 944 comprise gripping members 945, while second end extensions comprise gripping members 947. Central member 942 may comprise a pair of recesses or indentations 943 on each side that reduce the width of central member 942. Similar to clamp 1801 described above, clamp 940 may be formed from a single piece of material in certain embodiments.

First extensions 944 may be angled toward each other so that gripping members 945 are closer to each other than are the portions of first extensions 944 which are proximal to central member 942. Similarly, second extensions 946 may be angled toward each other so that gripping members 947 are closer to each other than are the portions of second extensions 946 which are proximal to central member 942. Such a configuration allows first and second extensions 944 and 946 to place a compressive force on bone 951. In certain embodiments, first and second extensions members 944 and 946 may be placed on bone 951 such that a fracture (not visible in FIG. 24) is between first and second extensions 944 and 946. Clamp 940 can therefore be used to secure or stabilize bone 950.

Referring now to FIGS. 26-27, a clamp 970 may be placed on a hip bone 971. In certain embodiments, clamp 970 may be placed on hip bone 971 in a location where a hip graft 979 has been removed. Clamp 970 comprises a coupling portion 976 that couples a first side 972 to a second side 974. In the embodiment shown, first and second sides 972, 974 each comprise gripping members 978 at an end distal from coupling portion 976. In the embodiment shown, gripping members 978 comprise a series of teeth, but other embodiments may comprise gripping members with different configurations.

Similar to previously-described embodiments, first and second sides 972, 974 may be angled toward each other so that they provide a compressive force on hip bone 971 and aid in securing clamp 970 to bone 971. In the embodiment shown, coupling portion 976 may also comprise a pair of apertures 973 that allow a tool (not shown) to be inserted for spreading first and second sides 972 and 974 away from each other. The use of a tool to spread clamp 970 farther open can make it easier to install. In addition, apertures 973 may be used to provide access to the bone underneath clamp 970 and allow for the application of bone growth hormone or bone cement to the area where a graft has been removed.

Referring now to FIGS. 28-29, a clamp 960 may be used to secure a calvarial or cranial flap 961. As shown in FIG. 29, when viewed from one end, clamp 960 has a shape that resembles a lower-case "h". Clamp 960 comprises a coupling portion 966 that couples a first side 962 to a second side 964. In the embodiment shown, first side 962 and second side 964 comprise gripping members 968 similar to previously-described embodiments. First side 962 and second side 964 may also be angled towards each other to provide a compressive force on cranial flap 961. First side 962 may also comprise an extension 963 with apertures 965 that can allow screws or other attachment mechanisms (not shown) to secure clamp 960 to a portion of the cranium that is proximal to calvarial flap 961. It is understood that other embodiments of clamp 960 may comprise different configurations. For example, clamp 960 may comprise a single aperture rather than the pair of apertures shown in FIGS. 28-29.

Referring now to FIGS. 30-33, an exemplary embodiment of a spinous process clamp system 1000 comprises one or more clamps 1001 and coupling members 1050. In this embodiment, clamps 1001 are similar to clamps 1801 described in FIGS. 18A-18B. Clamp 1001 comprises a central portion 1005 with a pair of side portions 1010, which are formed into a U-shape when viewed from one end of clamp 1001. The open ends of the U-shape of side portion 1010 may be closer together than the base of the U-shape. Such a configuration allows a side portion 1010 to place a compressive force on a coupling member 1050 or other member inserted into side portion 1010. In addition, side portions 1010 may comprise inner and outer apertures 1020 and 1025. In the embodiment shown, inner and outer apertures 1020, 1025 are multi-ed, specifically ten-sided. In other embodiments, the apertures may be different configurations. For example, the number of sides for the apertures may range from six sides to twenty sides, inclusive.

Side portions 1010 also comprise a pair of gripping members 1015 proximal to the space between side portions 1010. In the embodiment shown, gripping members 1015 comprise a series of teeth directed towards the space between side portions 1010. In other embodiments, gripping members may comprise a different configuration.

Clamp 1001 does not comprise a top portion and flanged portions coupled to central portion 1005 in a manner similar to clamp 1801. Instead, clamp 1001 comprises a pair of end portions 1006 and 1007 that fit over each end of a spinous process 1070. Such configuration may be useful when the spinous process is not large enough to accommodate a clamp at each end. Clamp 1001 comprises a pair of inner and outer apertures 1020 and 1025 on each side portion 1010. Having a pair of inner and outer apertures 1020 and 1025 allows a clamp 1001 to be coupled to additional clamps 1001 on adjacent spinous processes. Such couplings can be facilitated with coupling members 1050 in a manner similar to that disclosed for clamps 1801 and coupling members 1850. In the embodiment shown, coupling members 1050 are substantially similar to the previously-described coupling members 1850.

In addition, the inner walls 1012 of side portions 1010 may be angled towards each other so that they must be slightly spread apart in order to fit over spinous process 1070. Such a configuration may place a compressive force on spinous process 1070 and further assist in retaining clamp 1801 onto spinous process 1070.

Referring now to FIG. 34, a tool 1100 may be used to assist in spreading apart side portions 962 and 964 of clamp 960. Tool 960 comprises handles 1101 and 1102 which are coupled to arms 1103 and 1104 and rotate about pivot point 1105. Arms 1103 and 1104 comprise end members 1106 and 1107 which hook onto side portions 964 and 962. As handles 1101 and 1102 are squeezed together, arms 1103 and 1104 are spread apart, which in turn spread apart side portions 962 and 964. This can assist in installing clamp 960 onto a bone or other surface. It is understood that tool 1100 may be used with other configurations of clamps in addition to clamp 960.

FIG. 35 illustrates one embodiment of a system for fixation of spinous processes. In the depicted embodiment, the system includes a first anchor structure 1201, a second anchor structure 1202, and a fusion member 1203 configured to promote fusion of the spinous processes. As used herein, the term "fusion member" is defined as a member configured to promote fusion of spinous processes when placed between two spinous processes. A fusion member includes a device that is substantially porous to allow for bone growth into the fusion member. In certain embodiments, a fusion member may include a cage-like structure with bone or bone substitute material contained within the structure.

In the embodiment shown, the fusion member 1203 may be disposed between the first anchor structure 1201 and the second anchor structure 1202. In a further embodiment, the system may include a tension member 1204. In specific embodiments, the interspinous ligament (not shown) can be removed prior to insertion of fusion member 1203.

In one embodiment, the first anchor structure 1201 and the second anchor structure 1202 may include a cap configured to engage a bone structure. Specifically, the bone structure may be a spinous process. For example, the first anchor structure 1201 may include a cap configured to engage a first spinous process and the second anchor structure 1202 may include a cap configured to engage a second spinous process. In a further embodiment, the first anchor structure 1201 and the second anchor structure 1202 may be positioned in opposing directions. For example, the first anchor structure 1201 may be positioned to engage a top side of a spinous process and the second anchor structure may be positioned to engage a bottom side of a spinous process. The first and second anchor structures 1201-02 may be manufactured from metal. Alternatively, a polymer based substance, such as plastic or nylon may be used to manufacture the first and second anchor structures.

In a further embodiment, the first anchor structure 1201 may include a first alignment member 1206. Additionally, the first anchor structure 1201 may include a second alignment member 1211. The first alignment member 1206 and the second alignment member 1211 may be positioned on opposing sides of the first anchor structure 1201. Similarly, the second anchor structure may include a first alignment member 1208 and a second alignment member (shown, but not numbered). The alignment members 1206, 1208, 1211 may include a guide, a hole, a channel, a slot, a groove, or the like. Indeed, the alignment members 1206, 1208, 1211 may include many alternative embodiments. A combination of embodiments may also be used for alignment.

In the embodiment shown, fusion member 1203 includes a cage that defines a volume. The fusion member 1203 may include an interior surface and an exterior surface. In a further embodiment, one or more bone fragments 1213 may be disposed within the volume of the fusion member 1203. For example, the fusion member 1203 may include a cage or mesh sack containing multiple bone fragments. The bone fragments may be of various sizes. The fusion member may promote fusion of a first spinous process to a second spinous process and fusion of the facet joints. In a further embodiment, the fusion member 1203 may include a wire or polymer mesh. The mesh may form a sack. In certain embodiments, fusion member 1203 may be comprise a bone allograft or be configured as a bone allograft.

In certain embodiments, the spinous processes are smoothed down with a tool such as a high speed burr prior to insertion of fusion member 1203. Care should be taken by the surgeon not to violate the cortex unnecessarily. After the spinous processes have been prepared, the tool can be used to make several cortical perforations in the midline of the spinous processes on the faces to be fused. Care should also be taken not to violate the cortex upon which the cage walls (of fusion member 1203) will rest. The surgeon is encouraged to use the trial fusion members 1203 and mark the exposed bone prior to placement of the final fusion member 1203 that will be installed.

In one embodiment, the tension member 1204 may include a cable. Alternatively, the tension member 1204 may include a wire, a plate, a rod, or the like. The tension member 1204 may include a first end and a second end. The first end may couple to the first anchor structure 1201 and the second end may couple to the second anchor structure 1202. In a further embodiment, the tension member 1204 may be further coupled to the fusion member 1203. The tension member 1204 may also engage or fall in alignment with one or more of the alignment members 1206, 1208, 1211. In a further embodiment, the tension member 1204 may substantially comprise the coupling member 500 as described above with reference to FIGS. 12 and 13.

In one embodiment, the system may also include one or more fasteners 1209, 1210, 1212. The fasteners may fasten the tension member 1204 to the first anchor structure 1201 and to the second anchor structure 1202. For example, a first fastener 1209 may fasten the first end of the tension member 1204 to the first anchor structure 1201. In a further embodiment, the first fastener 1209 may be positioned adjacent to the first alignment member 1206. Indeed, the first fastener 1209 may be retained against a surface of the first alignment member 1206 when the tension member 1204 is installed. In one embodiment, the fastener 1209 includes a clamp or a crimp. Alternatively, the fastener 1209 may include a nut, a flange, a hook, a nodule configured to engage a groove or depression in the first anchor structure 1201, or the like.

In the depicted embodiment, the first anchor structure 1201 includes a cap configured to engage a top side of a first spinous process, and the second anchor structure includes a cap configured to engage a bottom side of a second spinous process. The fusion member 1203 is positioned between the first spinous process and the second spinous process. The alignment members 1206, 1207, and 1208 are each depicted as channels configured to receive the tension member 1204. In the depicted embodiment, a first tension member 1204 is a cable configured to be threaded through the alignment members 1206, 1207, 1208 on one side of the first anchor structure 1201, the fusion member 1203, and the second anchor structure 1202. A second tension member 1205 is also threaded through corresponding alignment members 1211 on the opposite side of the first anchor structure 1201, the fusion member 1203, and the second anchor structure 1202. In the depicted embodiment, the first tension member 1204 and the second tension member 1205 may run in substantially parallel directions. Both tension members 1204, 1205 are then fastened with fasteners 1209, 1210, 1212 so that the tension members 1204, 1205 provide tension between the first anchor structure 1201 and the second anchor structure 1202. The first anchor structure 1201 and the second anchor structure 1202 in turn draw the first spinous process and the second spinous process into closer proximity which compresses the fusion member 1203 between them.

FIG. 36 is a side view of the system described in FIG. 35. Additionally, the embodiment depicted in FIG. 36 includes one or more gripping members 1214, 1215. In one embodiment, the gripping members 1214, 1215 may be integrated portions of the first anchor structure 1201 and the second anchor structure 1202. Alternatively, the gripping members 1214, 1215 may be formed on or coupled to the first anchor structure 1201 and the second anchor structure 1202. In the depicted embodiment, the gripping member includes a first tab 1214 and a second tab 1215. The tabs 1214, 1215 may be cut out of the anchor structure on three sides to provide for flexion of the tab, but remain integrated with the anchor structure on the fourth side.

In a further embodiment, the tabs 1214, 1215 may further comprise one or more teeth 1216 configured to engage the surface of the bone structure. For example, the teeth 1216 may be formed on the tabs 1214, 1215 by punching the tab material through, wherein punching the material forms a burr or tooth 1216. The teeth 1216 may grip the surface of the bone structure.

The gripping members 1214, 1215 may attach the first anchor structure 1201 and the second anchor structure 1202 to the bone structure. For example, the first anchor structure 1201 may be positioned on the top surface of a first spinous process. Similarly, the second anchor structure 1202 may be positioned on the bottom surface of a second spinous process. The first anchor structure 1201, and the second anchor structure 1202 may then be aligned. Once the anchor structures 1201, 1202 have been aligned, the gripping members 1214, 1215 may be clamped or crimped to the surface of the spinous process. In such an embodiment, the teeth 1216 may engage the surface of the spinous process, thereby affixing the anchor structure to the spinous process.

FIGS. 37 and 38 illustrate a further embodiment of the system. In the depicted embodiment, multiple fusion members 1217, 1218 are compressed between multiple spinous processes (shown, but not numbered) and retained by the first anchor structure 1201, the second anchor structure 1202, and the tension members 1204, 1205. The depicted embodiment operates in substantially the same manner as the system described above with relation to FIGS. 35 and 36, but additional fusion members 1217, 1218 are required. Additionally, the dimensions and configurations of the tension members 1204, 1205 and the anchor structures 1201, 1202 may be adapted to accommodate the additional fusion members 1217, 1218 and any additional load that may need to be placed on the system by the tension member to compress the additional fusion members 1217, 1218.

FIG. 39 depicts the various tension loads and compression forces that may occur in the system described in FIGS. 35 and 36. In the depicted embodiment, a tension load is applied normal to the surface of the first alignment guide 1206 that is positioned adjacent to the first fastener 1209. This tension load results in an opposing force normal to the interface between the first anchor structure 1201 and the bone structure. In such an embodiment, the tension loads at the second anchor structure 1202 are substantially equal in magnitude, but in the opposing direction. Similarly, the normal force on the interface between the second anchor structure and the bone structure are in opposing directions as well. This results in opposing compression forces on the interface between the bone structures and the fusion member 1203.

In such an embodiment, the forces in the system are balanced and contained within the system. The tension members 1204, 1205 may be preloaded to ensure that the fusion member 1203 is always loaded in compression, under any skeletal position. This geometry does not rely on the gripping members 1214, 1215 to carry any load and eliminates to possibility of bone tear-out and device slippage.

A procedure for installing the described system may be minimally invasive because it may only require access to the affected spinous processes and facet joints. In a particular embodiment, the system may not require screws for fixation or attachment to the spinous process. For example, a surgeon may expose the spinous process and lamina. The surgeon may then perform any desired decompression, taking care to preserve the spinous process. The anchor members 1201, 1202 are then placed on the spinous process. Once the anchor members 1201, 1202 are positioned and aligned, the gripping members 1214, 1215 may affix the anchor members 1201, 1202 to the spinous processes. In a certain embodiment, a device may be used to facilitate compression or distraction of the space between the spinous processes. The fusion member 1203 may then be positioned between the spinous processes and aligned. The anchor members 1201, 1202 may then be coupled together by the tension members 1204, 1205. If desired, the surgeon may then perform a facet joint fusion. The incision is then closed.

FIG. 40 illustrates a further embodiment of the system. This embodiment comprises a first anchor structure 1301 and second anchor structure 1302, along with a fusion member 1303. First anchor member 1301 comprises a groove 1306 and a pair of guide members 1305, while second anchor member 1302 comprises a groove 1307 and a pair of guide members 1308. In certain embodiments, guide members 1304 and 1305 may be configured as eyelets, rings, or other suitable devices configured to allow a tension member (not shown) to pass through them.

Fusion member 1303 may comprise an interior volume 1312 and apertures 1311 extending from the interior volume 1312 to the external environment. Similar to previously-described embodiments, bone fragments (not shown) may be placed in interior volume 1312, and holes 1311 may assist in promoting the fusion of fusion member 1303 to a spinous process after installation. Fusion member 1303 may also comprise a series of projections 1312 that extend from the sides of fusion member 1303 Projections 1312 are spaced along fusion member 1303 at various locations so that a tension member (not shown) can be coupled to (e.g. wrapped around) a projection 1312 to provide the desired amount of tension on anchor member 1301 and/or anchor member 1307.

In addition, a tension member (not shown) may extend around first and second anchor members 1301, 1302 during installation. The tension member may fit into grooves 1306, 1307 and pass through guide members 1308, 1305.

FIG. 41 illustrates a further embodiment comprising a first anchor member 1401, a second anchor member 1402, a tension member 1404 and a fusion member 1403. In this view, first and second anchor members 1401 and 1402 are coupled together via tension member 1404. This embodiment also incorporates a groove 1406 and guide members 1405 in first anchor member 1401, as well as a groove 1407 and guide members 1408 in second anchor member 1402.

In the view shown in FIG. 41, tension member 1404 has been placed around first anchor member 1401 and second anchor member 1402 such that tension member 1404 fits into grooves 1406 and 1407. In addition, tension member 1404 passes through guide members 1405 and 1408. As explained in FIGS. 42-45, this embodiment can be used to fuse adjacent vertebrae.

Referring now to FIG. 42, a pair of adjacent spinous processes 1470, 1471 are shown. In preparation for the placement of an anchor structure, each spinous process has been modified to include a notch 1451 on the surface distal from where a fusion member will be inserted between the spinous processes. As shown in FIG. 43, fusion member 1403 has been placed between spinous processes 1470, 1471. Referring now to FIG. 44, first and second anchor structures 1401 and 1402 have been mounted to spinous processes 1470 and 1471, respectively. Fusion member 1403 remains inserted between spinous processes 1470 and 1471, while tension member 1404 has been placed around anchor members 1401, 1402. In the embodiment shown, tension member 1404 can place a tensile force on spinous process 1401 and 1402 so that they are directed towards fusion member 1403. Spinous processes 1470, 1471 can eventually be fused to fusion member 1403.

In further embodiments, adjacent spinous processes may be distracted prior to the insertion of a fusion member between the spinous processes. Referring now to FIG. 45, a first leverage member 1580 can be coupled to a first spinous process 1560. A second leverage member 1570 can also be coupled to a second spinous process 1570 that is adjacent to first spinous process 1560. Leverage members 1580 and 1590 may be any configuration that allows a user to exert a force to spinous processes 1560 and 1570 so that spinous processes 1560 and 1570 can be moved away from each other. In specific embodiments, leverage members 1580 and 1590 are threaded rods or screws that can be inserted into spinous processes 1560 and 1570 or other members configured to attach to spinous processes 1560 and 1570. In even more specific embodiments, leverage members 1580 and 1590 may be Caspar distractors. In other embodiments, spinous processes 1560 and 1570 may be distracted through the use of pins, clamps, tongs, or other devices suitable to impart a force to the spinous processes.

Leverage members 1580 and 1590 can be used to distract spinous processes 1560, 1570 and interspinous space 1585 by applying a force to leverage member 1580 in the direction of arrow 1581 and by applying a force to leverage member 1590 in the direction of arrow 1591. While the assembled system is shown in FIG. 45, it is understood that interspinous space 1585 can be distracted prior to the insertion of a fusion member or spacer 1503 between spinous processes 1560 and 1570. For example, leverage member 1580 can be coupled to first spinous process 1560 (in this example, by threading leverage member 1580 into spinous process 1560). In addition, leverage member 1590 can be coupled to spinous process 1570. A surgeon may then apply forces to leverage members 1580 and 1590 (in the directions of arrows 1581 and 1591, respectively). While the forces are applied to leverage members 1580 and 1590, a fusion member 1503 can be inserted between spinous processes 1560 and 1570.

In other embodiments, leverage members 1580 and 1590 may be used to exert a compression force on spinous processes 1560, 1570 (e.g. by applying a force on leverage members 1580, 1590 in a direction opposite of directions 1581, 1591 respectively).

A method for treating spinal disorders is therefore provided wherein a first leverage member (e.g., a screw or other attaching member) is placed into a spinous process and a second leverage member is placed into an adjoining process. Distraction or compression can then be exerted onto these leverage members to allow for spinal manipulation intraoperatively. Once the spine has been positioned to the surgeon's satisfaction, an interposition cage or bone graft or clamping apparatus can be placed to hold the desired spinal alignment. This cage (or bone graft or clamping apparatus) can then be secured in place according to techniques described in this disclosure.

Still other embodiments may use a different mechanism to distract spinous processes 1560 and 1570 prior to insertion of fusion member 1503. For example, a distraction member 1592 may be used (either separate from or in conjunction with leverage members 1580 and 1590) to distract spinous processes 1560 and 1570. Distraction member 1592 may comprise a threaded rod, compressed spring or other device that can be manipulated to apply a force to spinous processes 1560 and/or 1570. Fusion member 1503 may be inserted between spinous processes 1560 and 1570 while they are spread apart by distraction member 1592. After fusion member 1503 has been inserted between spinous processes 1560 and 1570, distraction member 1592 may be removed or may be left in place. If distraction member 1592 is left in place it may be manipulated so that it is no longer exerting a distracting force against spinous process 1560 and/or 1570. For example, distraction member 1592 can be shortened by rotating threaded components, or by compressing a spring. Once installed, fusion member 1503 can be held in place between spinous processes 1560 and 1570 in any number of the ways as provided in the description of the embodiments in this disclosure. It is understood that in other embodiments, fusion member 1503 may be secured between spinous processes 1560 and 1570 without anchor members 1501 and 1502 or tension member 1504 shown in FIG. 45.

In certain embodiments, fusion member 1503 can be selected with a size sufficient to maintain distraction of interspinous space 1585 after the force is no longer applied to leverage members 1580, 1590. For example, fusion member 1503 can have a length that is greater than the distance between spinous processes 1560 and 1570 before forces are applied to leverage members 1580 and 1590. When leverage members 1580 and 1590 are used to increase the distance between spinous members 1560 and 1570, fusion member 1503 can be inserted between the two spinous members. After the force is removed from leverage members 1580 and 1590, fusion member 1503 can maintain a greater distance between spinous processes 1560 and 1570 than previously existed (e.g., before a force was applied to leverage members 1580, 1590). In certain embodiments, leverage members 1580 and 1590 may then be removed from spinous processes 1560 and 1580, and if necessary, any bone bleeding can be controlled by applying bone wax to the affected area. It is understood that fusion member 1503 may be equivalent to any of the previously described fusion members or other members inserted between two spinous processes.

In still other embodiments, the method of distracting the interspinous space can be accomplished without the use of leverage members coupled to the adjacent spinous processes. For example, as shown in FIG. 46, a spacer or fusion member 1533 is shown to have one or more tapered surfaces 1531 and 1532. In the embodiment shown, tapered surfaces 1531 and 1532 extend away from each other so that the distance between them varies. In this embodiment, the distance between tapered surfaces 1531 and 1532 proximal to interior surface 1535 is less than the distance W between spinous processes 1560 and 1570. However, the distance between tapered surfaces 1531 and 1532 proximal to exterior surface 1536 is greater than the distance W.

Fusion member 1533 can be forced between spinous members 1560 and 1570 (e.g. by applying a force on exterior surface 1536 in the direction of arrow 1539). As fusion member 1535 is forced between spinous members 1560 and 1570, the distance W will increase and interspinous space 1585 will become distracted. Anchor structures and tension members (for example, those similar to previously-described embodiments) could then be installed to complete the system.

FIG. 47 illustrates a system 10 comprising a securement device, e.g. a band 40 and a fusion member 80 installed so that fusion member 80 is located between spinous processes 5 and 15. In addition, band 40 forms a loop 41 that extends around spinous process 5 and 15. Other exemplary embodiments may comprise a first band that extends around spinous process 5 and a second band that extends around spinous process 15.

FIG. 48 provides a perspective view of band 40 in isolation so that various features of band 40 may be more readily seen. As explained in more detail below, system 10 also comprises an adjustment member 50 that can be used to adjust the circumference of loop 41 and secure band 40 around spinous processes 5 and 15.

In this embodiment, band 40 also comprises a pair of alignment members 47 (only one of which is visible in FIG. 48) which may be used to align band 40 with fusion member 80. Referring now to FIG. 49 (an end view of one embodiment of fusion member 80), a slot 84 is formed on each side of fusion member 80. Each alignment member 47 is configured to engage a slot 84 in fusion member 80. In the particular embodiment shown, alignment member 47 and slot 84 form a dovetail joint that allows band 40 to slide longitudinally (e.g., parallel to an axis extending between spinous processes 5 and 15) relative to fusion member 80. The engagement of alignment member 47 and slot 84 restricts vertical movement (e.g., perpendicular to an axis between spinous processes 5 and 15) of band 40 relative to fusion member 80.

In the embodiment shown in FIG. 47, fusion member 80 forms a cage 87 defining an inner volume 86. Fusion member 80 also comprises a plurality of apertures 81 and an indentation, concavity or recess 85 on each end. Recess 85 is configured to receive a spinous process and aid in aligning fusion member 80 between spinous processes 5 and 15. As shown in FIG. 47, fusion member 80 generally forms an "H" shape when viewed from above. A plurality of bone fragments 83 (only a portion of which are shown in FIG. 47) may also be disposed within inner volume 86 to assist in fusing fusion member 80 to spinous processes 5 and 15. Apertures 81 can be concentrated in the areas where each recess 85 contacts a spinous process, and also promote fusion of fusion member 80 to spinous processes 5 and 15.

As shown in FIGS. 47 and 48, band 40 comprises a first end 42 and a second end 43. In this embodiment, band 40 comprises a plurality of openings 45 and a plurality of engagement members 44 proximal to first end 42. In the embodiment shown, engagement members 44 and openings 45 are arranged to form a series of alternating engagement members and openings so that an engagement member 44 is located between a pair of openings 45.

In this embodiment, band 40 also comprises a retention member 46 configured to retain adjustment member 50. In the illustrated embodiment, retention member 46 is proximal to second end 43 of band 40. In the embodiment shown, retention member 46 comprises a pair of extensions protruding from each side of band 40. The protrusions each comprise an aperture through which adjustment member 50 may extend.

As shown in FIG. 47, adjustment member 50 comprises a plurality of projections 51 configured to engage the plurality of engagement members 44 of band 40. Projections 51 can extend into openings 45 and exert a force on engagement members 44 as adjustment member 50 is rotated. In certain embodiments, adjustment member 50 may comprise a receiving portion 55 configured to receive a tool (such as an hex wrench, not shown) to provide leverage for the rotation of adjustment member 50.

Upon rotation of adjustment member 50 in a first direction (in this embodiment, clockwise when viewed from the top), first end 42 will be translated away from adjustment member 50 (e.g., towards spinous process 15). The circumference of loop 41 will therefore be reduced, and band 40 tightened around spinous processes 5 and 15. Fusion member 80 will also be secured between the spinous process 5 and 15.

In this embodiment, adjustment member 50 also comprises a biasing member 52 configured to bias adjustment member 50 to a locked position by engaging a ratchet mechanism 54. When ratchet mechanism 54 is engaged, adjustment member 50 is prevented from being rotated in a direction (e.g. counterclockwise when viewed from the top in this embodiment) that would increase the circumference of loop 41 formed by band 40. When ratchet mechanism 54 is engaged, adjustment member 50 can be rotated to reduce circumference 41 and tighten band 40 around spinous process 5 and 15, allowing band 40 to remain secure in place.

Adjustment member 50 can be moved from the locked position shown in FIG. 47 to an unlocked position (not shown) by exerting a force to overcome the force exerted by biasing member 52. For example a tool may be inserted into receiving portion 55 and pushed towards biasing member 52, so that biasing member 52 is compressed and ratchet mechanism 54 is disengaged. With ratchet mechanism 54 disengaged, adjustment member 50 can be rotated (in this embodiment, counterclockwise when viewed from the top) to increase the circumference of loop 41.

During a typical installation procedure, it may not be necessary to disengage ratchet mechanism 54 to increase the circumference of loop 41. For example, band 40 can be positioned so that alignment members 47 are engaged in a sliding fixation with slots 84 of fusion member 80. This can allow fusion member 80 and band 40 to be installed together as a unit. Band 40 can positioned to form a loop 41 with a circumference that is large enough to pass over spinous processes 5 and 15, and fusion member 80 can be placed between spinous process 5 and spinous process 15. In other embodiments, fusion member 80 can be installed initially between spinous processes 5 and 15, and band 40 can be subsequently placed around the spinous processes.

When fusion member 80 is located between spinous processes 5 and 15 and band 40 is extended around spinous processes 5 and 15, adjustment member 50 can be manipulated to reduce the circumference of loop 41. As the circumference of loop 41 is reduced, band 40 is tightened around spinous processes 5 and 15 to secure fusion member 80 and band 40 in place. When the circumference of loop 41 is reduced sufficiently, fusion member 80 can be compressed between spinous process 5 and spinous process 15.

As shown in FIGS. 47 and 48, band 40 comprises several features that increase the flexibility of band 40. For example, band 40 comprises a plurality of openings that promote flexibility. In the embodiment shown, band 40 comprises a first and second plurality of openings 48 and 49 configured as parallel slots that extend partially around the circumference of loop 41 formed by band 40. In the illustrated embodiment, first and second plurality of openings 48 and 49 are located where band 40 is configured to engage spinous processes 5 and 15 during use.

Exemplary embodiments may also comprise one or more narrowed portions of band 40 to increase flexibility. The illustrated embodiment comprises a first and second narrowed portion 51 and 52 on either side of the first plurality of openings 48 so that first plurality of openings 48 are between first and second narrowed portion 51 and 52. In addition, the illustrated embodiment comprises a second and third narrowed portion 53 and 54 on either side of the second plurality of openings 49. Together, first and second plurality of openings 48 and 49, along with first, second, third and fourth narrowed portions 51, 52, 53, and 54 make it easier for band 40 to tighten around spinous processes 5 and 15. In certain embodiments, band 40 may comprise molded polymer or other flexible material.

Referring now to FIG. 50, certain embodiments may comprise a first fusion member 80 inserted between first spinous process 5 and second spinous process 15 and a second fusion member 80 inserted between second spinous process 15 and third spinous process 20. In this embodiment a first band 40 is coupled to a second band 40 to form a loop around first spinous process 5 and third spinous process 25. In the embodiment shown, first and second bands 40 are coupled together via a pair of adjustment members 50 in the manner equivalent to that previously described in the discussion of FIGS. 1-3. One or more of the adjustment members can be manipulated to adjust the circumference of the loop.

In other embodiments, fusion member 80 (or a similar fusion member) may be secured to spinous processes 5 and 15 without the use of band 40. For example, fusion member 80 may be secured to spinous processes 5 and 15 via one or more screws (not shown) or by incorporating tapered surfaces similar to that shown in FIG. 46.

Referring now to FIGS. 51 and 52, certain exemplary embodiments may also comprise one or more stabilizing members or plates that extend between spinous processes of vertebrae. In the embodiment shown, a first plate 1640 and a second plate 1650 extends between spinous processes 1610, 1620 and 1630. First and second plates 1640 and 1650 may be configured from a suitable material, including a polyetheretherketone material (PEEK) or a metallic alloy, including for example stainless steel or titanium.

In specific embodiments, interspinous spaces 1615 and 1625 may be distracted prior to the installation of first and second plates 1640, 1650. In the embodiment shown in FIGS. 51 and 52, interspinous spaces 1615 is distracted by inserting a spacer or fusion member 1611 between spinous processes 1610 and 1620. Similarly, interspinous space 1625 is distracted by inserting fusion member 1621 between spinous processes 1620 and 1630.

It is understood that in other embodiments, interspinous space 1615 and/or interspinous space 1625 may be distracted by other embodiments or systems. For example, the interspinous spaces may be distracted by the use of leverage members similar to leverage members 1580 and 1590, as described in previous embodiments. It is also understood that fusion members 1611 and 1621 may be comprise other configurations, including those shown in previously-described embodiments. For example, fusion members 1611 and 1621 may be configured similar to fusion member 1503. Other embodiments may include a bone graft inserted between the spinous processes.

In the embodiment shown in FIGS. 51 and 52, first and second plates 1640 and 1650 are coupled together by a plurality of coupling members 1641. In certain embodiments, coupling members 1641 may comprise one or more threaded components, including for example, screws or bolts. First and second plates 1640, 1650 may also comprise a plurality of apertures 1642 that allow the plates to be coupled directly to the spinous processes 1610, 1620 and 1630. As shown in FIG. 51, fusion members 1611, 1621 each comprise an aperture 1612, 1622 configured to allow a coupling member 1641 to pass through the fusion member. This configuration allows coupling members 1641 to couple plates 1640 and 1650 on each side of spinous process 1610, 1620 and 1630. Fusion members 1611, 1621 can still be configured to retain bone fragments or bone substitute (not shown) in order to promote fusion with spinous processes 1610, 1620 and 1630.

Other embodiments may comprise one or more stabilization members that are coupled to the spinous processes in other manners besides that shown in FIGS. 51 and 52. In addition, a stabilization member may be coupled to a different number of spinous processes than the embodiment shown in FIGS. 51 and 52. Referring now to FIGS. 53 and 54, a stabilization member or plate 1740 extends between spinous processes 1710 and 1720. Similar to the embodiment shown in FIGS. 51 and 52, interspinous space 1715 is distracted prior to the installation of plate 1740 by inserting fusion member 1711 between spinous processes 1710 and 1720.

In this embodiment, plate 1740 is coupled to spinous processes 1710 and 1720 via coupling members 1741 (e.g., screws) that thread directly into the spinous processes. It is understood that other embodiments may comprise different methods or configurations to couple plate 1740 to spinous processes 1710 and 1720. It is also understood that plate 1740 may be coupled to spinous processes 1710 and 1720 in a location different from that illustrated in FIGS. 53 and 54. For example, plate 1740 may be coupled to spinous processes 1710 and 1720 in an area on the side, rather than the top of spinous processes 1710 and 1720.

Referring now to FIGS. 55 and 56, a fusion member 1911 is inserted between spinous processes 1910, 1920 of vertebrae 1901, 1902. In this embodiment, fusion member 1911 is configured similar to fusion member 80 shown in FIG. 47, and comprises an inner volume containing fusion particles 1812. In certain embodiments, fusion particles 1812 may comprise bone fragments or bone substitute material. The embodiment shown in FIGS. 55 and 56 also comprises a pair of stabilization members 1940, 1950 that are configured to extend around fusion member 1911 and couple to spinous processes 1910, 1920. As shown in FIG. 56, in this embodiment stabilization members 1940, 1950 are coupled to spinous processes 1910, 1920 via one or more coupling members 1941. In specific embodiments, coupling members 1941 may be threaded components (e.g., screws or bolts). In certain embodiments, interspinous space 1815 may be distracted prior to insertion of fusion member 1811 between spinous processes 1810 and 1820.

Referring now to FIGS. 57 and 58, a fusion member 2011 is configured to be inserted between spinous processes 2010 and 2020. Fusion member 2011 is similar to previously-described fusion member 1911, but comprises integral stabilization members 2040, 2050 rather than separate stabilization members. Fusion member 2011 also comprises an inner volume containing fusion particles 2012.

The plates described in FIGS. 51-58 can be coupled to the spinous processes to provide additional stabilization of the vertebrae. The plates can serve to keep the adjacent vertebrae in the desired alignment. In certain configurations, the plates can also retain a fusion member between the adjacent processes.

In certain exemplary embodiments, the tools used to set the clamps can be sterilized and re-used. In other exemplary embodiments, the tools used to set the clamps will be designed for one-time use. Clamps according to exemplary embodiments may be manufactured from suitable medical-grade materials, including titanium and stainless steel.

It should be understood that the present system, kits, apparatuses and methods are not intended to be limited to the particular forms disclosed. Rather, they are to cover all modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description of Exemplary Embodiments, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description of Exemplary Embodiments, with each claim standing on its own as a separate embodiment.

The invention claimed is:

1. A system comprising:
   a fusion member configured for insertion between a first spinous process and a second spinous process;
   where the fusion member is H-shaped having two upper and two lower extensions and is secured to the first spinous process between the two upper extensions and the second spinous process between the two lower extensions by one or more protrusions disposed on the inner surface of the upper and lower extensions and oriented inward with respect to each other configured to partially penetrate the first spinous process and the second spinous process; and
   where the fusion member further comprises a cage defining a volume for receiving fusion material, said cage defining an opening on a top surface which is configured to be disposed outward with respect to a spine when inserted to receive fusion material, said cage further comprising a plurality of apertures adapted to provide contact area between fusion material and the first and second spinous processes;
   a securement device wherein the securement device is selected from the group consisting of: a band, a plate, a pedicle screw, a pedicle screw system, a clamp, a bracket, a wire, a cable, and a prong; and
   an adjustment member configured to adjust the circumference of a loop, and wherein the securement device comprises a band that can be configured to form a loop around a first spinous process and a second spinous process.

2. The system of claim 1, wherein the fusion material comprises bone tissue.

3. The system of claim 1 wherein the band comprises a polymer.

4. The system of claim 3 wherein the polymer is a molded polymer.

5. The system of claim 1 wherein the band comprises an alignment member configured to engage a slot in the fusion member.

6. The system of claim 5 wherein the alignment member and the slot are engaged in a sliding fixation.

7. The system of claim 5 wherein the alignment member and the slot form a dovetail joint.

8. The system of claim 1 wherein the band comprises a plurality of openings configured to increase the flexibility of the band.

9. The system of claim 8 wherein the plurality of openings comprises parallel slots configured to extend partially around the circumference of the loop.

10. The system of claim 8 wherein the plurality of openings are located where the band is configured to engage a spinous process during use.

11. The system of claim 1 wherein the band comprises a narrowed portion configured to increase the flexibility of the band.

12. The system of claim 1 wherein the band comprises:
    a first plurality of openings;
    a second plurality of openings; and
    a first narrowed portion, a second narrowed portion, a third narrowed portion and a fourth narrowed portion, wherein the first plurality of openings are located between the first and second narrowed portions and wherein the second plurality of openings are located between the third and fourth narrowed portions.

13. The system of claim 1 wherein the band comprises:
    a first end;
    a second end; and
    a plurality of engagement members proximal to the first end.

14. The system of claim 13 further comprising a plurality of openings, wherein an engagement member is located between a pair of openings.

15. The system of claim 14 wherein the plurality of openings and the plurality of engagement members are arranged such that the openings and engagement members form a series of alternating openings and engagement members.

16. The system of claim 13 wherein the band comprises a retention member configured to retain the adjustment member.

17. The system of claim 16 wherein the adjustment member is configured to rotate within the retention member and adjust the circumference of the loop.

18. The system of claim 13 wherein the adjustment member is configured to engage the plurality of engagement members proximal to the end of the band.

19. The system of claim 13 wherein the adjustment member comprises a plurality of projections configured to engage the plurality of engagement members proximal to the end of the band.

20. The system of claim 13 further comprising a biasing member configured to bias the adjustment member to a locked position.

21. The system of claim 20 further comprising a ratchet mechanism, wherein the ratchet mechanism is configured to allow the adjustment member to reduce the circumference of the loop when the adjustment member is in the locked position.

22. The system of claim 20 wherein the adjustment member can be moved from the locked position to an unlocked position by overcoming a force exerted on the adjustment member by the biasing member.

23. The system of claim 22 wherein the adjustment member can be manipulated to increase the circumference of the loop when the adjustment member is in the unlocked position.

24. The system of claim 1 wherein the fusion member is configured to be compressed between a first spinous process and a second spinous process during use.

25. A fusion member comprising:
a body comprising a first end and a second end;
a first concave portion proximal to the first end, wherein the first concave portion is configured to engage a first spinous process; and
a second concave portion proximal to the second end, wherein the second concave portion is configured to engage a second spinous process;
where the fusion member is secured to the first spinous process and the second spinous process by one or more protrusions disposed on the inner surfaces of the first and second concave portions which are configured to partially penetrate the first spinous process and the second spinous process to provide for attachment to the first and second spinous process and to facilitate stabilization of the fusion member when inserted;
where the fusion member further comprises a cage defining a volume for receiving fusion material, said cage defining an opening on a top surface which is configured to be disposed outward with respect to a spine when inserted to receive fusion material, said cage further comprising a plurality of apertures adapted to provide contact area between fusion material and the first and second spinous processes.

26. The fusion member of claim 25, wherein the body of the fusion member comprises an "H" shape when viewed from above in an installed position.

27. The fusion member of claim 25, wherein the plurality of apertures are in the first concave portion and in the second concave portion.

28. An interspinous member wherein the interspinous member is configured to engage adjacent spinous processes and comprises:
a first concave portion configured to engage a first spinous process; and
a second concave portion configured to engage a second spinous process;
where the interspinous member is secured to the first spinous process and the second spinous process by one or more protrusions configured to partially penetrate the first spinous process and the second spinous process;
where the interspinous member is configured to promote fusion of the first spinous process and the second spinous process; and
where the fusion member further comprises a cage defining a volume for receiving fusion material, said cage defining an opening on a top surface which is configured to be disposed outward with respect to a spine when inserted to receive fusion material, said cage further comprising a plurality of apertures adapted to provide contact area between fusion material and the first and second spinous processes.

* * * * *